US007582429B2

(12) United States Patent
Wittwer et al.

(10) Patent No.: US 7,582,429 B2
(45) Date of Patent: Sep. 1, 2009

(54) AMPLICON MELTING ANALYSIS WITH SATURATION DYES

(75) Inventors: Carl T. Wittwer, Salt Lake City, UT (US); Gudrun Reed, Salt Lake City, UT (US); Virginie Dujols, Sandy, UT (US); Luming Zhou, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 427 days.

(21) Appl. No.: 10/531,966

(22) PCT Filed: Oct. 22, 2003

(86) PCT No.: PCT/US03/33429

§ 371 (c)(1),
(2), (4) Date: Apr. 20, 2005

(87) PCT Pub. No.: WO2004/038038

PCT Pub. Date: May 6, 2004

(65) Prior Publication Data

US 2006/0019253 A1    Jan. 26, 2006

Related U.S. Application Data

(60) Provisional application No. 60/420,717, filed on Oct. 23, 2002, provisional application No. 60/439,978, filed on Jan. 14, 2003.

(51) Int. Cl.
  *C12Q 1/68*   (2006.01)
  *C12P 19/34*  (2006.01)
  *C07H 21/04*  (2006.01)
(52) U.S. Cl. .................. 435/6; 435/91.2; 536/24.33
(58) Field of Classification Search ............ 435/6, 435/91.2; 536/24.31, 24.33, 24.32
  See application file for complete search history.

(56) References Cited

U.S. PATENT DOCUMENTS

| 5,321,130 | A  |   | 6/1994  | Yue et al.              |       |
|-----------|----|---|---------|-------------------------|-------|
| 5,436,134 | A  |   | 7/1995  | Haugland et al.         |       |
| 5,491,063 | A  |   | 2/1996  | Fisher et al.           |       |
| 5,563,037 | A  | * | 10/1996 | Sutherland et al.       | 435/6 |
| 5,658,751 | A  |   | 8/1997  | Yue et al.              |       |
| 5,871,908 | A  |   | 2/1999  | Henco et al.            |       |
| 6,174,670 | B1 | * | 1/2001  | Wittwer et al.          | 435/6 |
| 6,346,386 | B1 | * | 2/2002  | Elenitoba-Johnson       | 435/6 |
| 6,437,141 | B2 |   | 8/2002  | Randall et al.          |       |
| 6,506,568 | B2 |   | 1/2003  | Shriver et al.          |       |
| 6,927,027 | B2 | * | 8/2005  | Erikson et al.          | 435/6 |
| 7,387,887 | B2 | * | 6/2008  | Wittwer et al.          | 435/91.2 |
| 2001/0046670 | A1 |   | 11/2001 | Brookes              |       |
| 2003/0157507 | A1 |   | 8/2003  | Lipsky et al.         |       |

FOREIGN PATENT DOCUMENTS

| WO | WO 00/66664 | 11/2000 |
| WO | WO 0066664 A1 * | 11/2000 |
| WO | WO 01/48237 | 5/2001 |
| WO | WO 02/26891 | 4/2002 |

OTHER PUBLICATIONS

Higuchi R. , et al. Simultaneous amplification and detection of specific DNA sequences. Biotechnology, vol. 10, pp. 413-417, 1992.*
Nurmi J., et al. High-throughput genetic analysis using time-resolved flurometry and closed-tube detection. Anal Biochem., vol. 299, pp. 211-217, 2001.*
Nurmi J., et al. High-throughput genetic analysis using time-resolved fluorometry and closed-tube detection. Anal Biochem., vol. 299, pp. 211-217, 2001.*
Abrams, E.S., et al., Genomics 1990; 7:463-75.
Aktipis, S., et al., Biochemistry 1975; 14:326-31.
Aoshima, T., et al., Clin Chem 2000; 46:119-22.
Crockett, A.O. and C. T. Wittwer, Anal. Biochem. 2001; 290:89-97.
Deichmeister, M.V., et al., Khim. Geteroltiski. Soedin., Sb. 1: Azotsoderzhashchie Geterotsikly (1967). SciFinder Abstract.
Douthart, R.J., et al., Biochemistry 1973; 12:214-20.
Germer, S., et al., Genome Research 2000; 10:258-266.
Germer, S., et al., Genome Research 1999; 9:72-79.
Gundry, C.N., et al., Genetic Testing, 1999; 3:365-70.
Herrmann, M., et al., Clin Chem 2000; 46:425-8.
Highsmith, W.E., et al., Electrophoresis 1999; 20:1186-94.
Higuchi, R., et al., Biotechnology, 1992; 10:413-17.
Ishiguro, T., et al., Anal Biochem 1995; 229:207-13.
Lay, M.J., et al., Clin Chem 1997; 43:2262-7.
Lipski, R.H., et al., Clin Chem 2001; 47:635-44.
Marziliano, N., et al., Clin Chem 2000; 46:423-5.
Nataraj, A.J., et al., Electrophoresis 1999; 20:1177-85.
Orita, O., et al., Proc Natl Acad Sci USA 1989; 86:2766-70.
Pirulli, D., et al., Clin Chem 2000; 46:1842-4.
Press, W.H., et al., eds. Numerical recipes in C, 2nd ed. New York; Cambridge University Press, 1992:650-5.
Ririe, K.M., et al., Anal. Biochem 1997; 245:154-60.
Santalucia, J., Jr., Biochemistry 1996; 35:3555-62.
Taylor, G.R., et al., Genet Anal 1999; 14:181-6.
Tseng, B.Y., et al., Anal. Biochem 1997; 245:207-12.
Venter, J.C., et al., Science 2001; 291:1304-51.
Von Ahsen, N., et al., Clin Chem 2001; 47:1331-1332.
Von Ahsen, N., et al., Clin Chem 2001; 47:1956-61.
Wartell, R.M., et al., J Chromatogr A 1998;806:169-8.
Wetmur, J.G., Crit Rev Biochem Mol Biol 1991; 26:227-59.
Wittwer, C.T., et al., BioTechniques 1997; 22:130-8.
Xiao, W., et al. Hum Mutat 2001; 17:439-74.

* cited by examiner

*Primary Examiner*—Suryaprabha Chunduru
(74) *Attorney, Agent, or Firm*—Ice Miller LLP; Homer W. Faucett, III

(57) ABSTRACT

Methods are provided for nucleic acid analysis wherein a target nucleic acid that is at least partially double stranded is mixed with a dsDNA binding dye having a percent saturation of at least 50% to form a mixture. In one embodiment, the nucleic acid is amplified in the presence of the dsDNA binding dye, and in another embodiment a melting curve is generated for the target nucleic acid by measuring fluorescence from the dsDNA binding dye as the mixture is heated. Dyes for use in nucleic acid analysis and methods for making dyes are also provided.

18 Claims, 23 Drawing Sheets

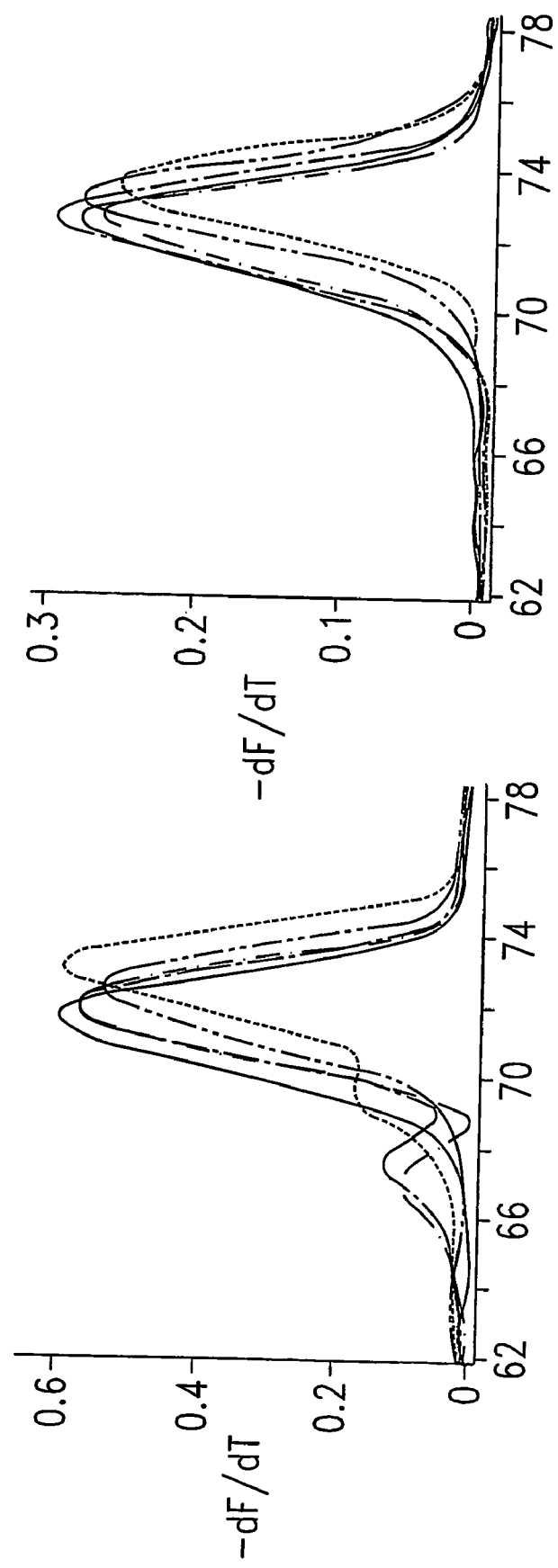

AMPLICON MELTING ANALYSIS WITH SATURATION DYES

The present application is a U.S. National Application of PCT/US2003/033429, filed Oct. 22, 2003, which claims priority to U.S. Provisional Ser. No. 60/439,978, filed Jan. 14, 2003, and U.S. Provisional Ser. No. 60/420,717, filed Oct. 23, 2002, the contents of which are herein incorporated by reference.

This invention was made with government support under Grant #GM58983, awarded by the National Institutes of Health. The Government has certain rights to this invention.

FIELD OF THE INVENTION

The present invention relates to methods of performing nucleic acid analysis in the presence of a double-stranded nucleic acid binding dye.

BACKGROUND OF THE INVENTION

Methods for analyzing DNA sequence variation can be divided into two general categories: 1) genotyping for known sequence variants and 2) scanning for unknown variants. There are many methods for genotyping known sequence variants, and single step, homogeneous, closed tube methods that use fluorescent probes are available (Lay M J, et al., Clin. Chem 1997;43:2262-7). In contrast, most scanning techniques for unknown variants require gel electrophoresis or column separation after PCR. These include single-strand conformation polymorphism (Orita O, et al., Proc Natl Acad Sci USA 1989; 86:2766-70), heteroduplex migration (Nataraj A J, et al., Electrophoresis 1999;20:1177-85), denaturing gradient gel electrophoresis (Abrams E S, et al., Genomics 1990;7:463-75), temperature gradient gel electrophoresis (Wartell R M, et al., J Chromatogr A 1998;806:169-85), enzyme or chemical cleavage methods (Taylor G R, et al., Genet Anal 1999;14:181-6), as well as DNA sequencing. Identifying new mutations by sequencing also requires multiple steps after PCR, namely cycle sequencing and gel electrophoresis. Denaturing high-performance liquid chromatography (Xiao W, et al., Hum Mutat 2001;17:439-74) involves injecting the PCR product into a column.

Recently, homogeneous fluorescent methods have been reported for mutation scanning. SYBR® Green I (Molecular Probes, Eugene, Oreg.) is a double strand-specific DNA dye often used to monitor product formation (Wittwer C T, et al., BioTechniques 1997;22:130-8) and melting temperature (Ririe K M, et al., Anal. Biochem 1997;245:154-60) in real-time PCR. The presence of heterozygous single base changes have been detected in products up to 167 bp by melting curve analysis with SYBR® Green I (Lipslcy R H, et al., Clin Chem 2001;47:635-44). However, subsequent to amplification and prior to melting analysis, the PCR product was purified and high concentrations of SYBR® Green I were added. The concentration of SYBR® Green I used for detection in this method inhibits PCR (Wittwer C T, et al., BioTechniques 1997;22:130-1, 134-8); thus, the dye was added after amplification. A dye that could be used to detect the presence of heterozygous single base changes and could be added prior to PCR would be desirable.

Single nucleotide polymorphisms (SNPs) are by far the most common genetic variations observed in man and other species. In these polymorphisms, only a single base varies between individuals. The alteration may cause an amino acid change in a protein, alter rates of transcription, affect mRNA splicing, or have no apparent effect on cellular processes. Sometimes when the change is silent (e.g., when the amino acid it codes for does not change), SNP genotyping may still be valuable if the alteration is linked to (associated with) a unique phenotype caused by another genetic alteration.

There are many methods for genotyping SNPs. Most use PCR or other amplification techniques to amplify the template of interest. Contemporaneous or subsequent analytical techniques may be employed, including gel electrophoresis, mass spectrometry, and fluorescence. Fluorescence techniques that are homogeneous and do not require the addition of reagents after commencement of amplification or physical sampling of the reactions for analysis are attractive. Exemplary homogeneous techniques use oligonucleotide primers to locate the region of interest and fluorescent labels or dyes for signal generation. Illustrative PCR-based methods are completely closed-tubed, using a thermostable enzyme that is stable to DNA denaturation temperature, so that after heating begins, no additions are necessary.

Several closed-tube, homogeneous, fluorescent PCR methods are available to genotype SNPs. These include systems that use FRET oligonucleotide probes with two interacting chromophores (adjacent hybridization probes, TaqMan probes, Molecular Beacons, Scorpions), single oligonucleotide probes with only one fluorophore (G-quenching probes, Crockett, A. O. and C. T. Wittwer, Anal. Biochem. 2001;290: 89-97 and SimpleProbes, Idaho Technology), and techniques that use a dsDNA dye instead of covalent, fluorescently-labeled oligonucleotide probes. The dye techniques are attractive because labeled oligonucleotide probes are not required, allowing for reduced design time and cost of the assays.

Two techniques for SNP typing using dsDNA dyes have been published. Allele-specific amplification in the presence of dsDNA dyes can be used to genotype with real-time PCR (Germer S, et al., Genome Research 2000;10:258-266). In the method of the Germer reference, two allele-specific primers differ at their 3'-base and differentially amplify one or the other allele in the presence of a common reverse primer. While no fluorescently-labeled oligonucleotides are needed, genotyping requires three primers and two wells for each SNP genotype. In addition, a real-time PCR instrument that monitors fluorescence each cycle is necessary.

The other dye-based method does not require real-time monitoring, needs only one well per SNP genotype, and uses melting analysis (Germer, S, et. al., Genome Research 1999; 9:72-79). In this method, allele-specific amplification is also used, requiring three primers, as with the previous Germer method. In addition, one of the primers includes a GC-clamp tail to raise the melting temperature of one amplicon, allowing differentiation by melting temperature in one well. Fluorescence is monitored after PCR amplification, and real-time acquisition is not required.

SUMMARY OF THE INVENTION

In one aspect of the present invention, a method is provided that requires only standard PCR reagents, primers, and the simple addition of a "saturating" double-stranded (ds) DNA binding dye prior to PCR. For purposes of this invention, a "saturating" dye is a dye that does not significantly inhibit PCR when present at concentrations that provide maximum fluorescence signal for an amount of dsDNA typically generated by PCR in the absence of dye, illustratively about 10 ng/µL. Although the dyes are identified by their compatibility with PCR at near saturating concentrations, it is understood that the dyes can be used at much lower concentrations.

During or subsequent to amplification, the dyes may be used to distinguish heteroduplexes and homoduplexes by melting curve analysis in a similar fashion to when labeled primers are used. The identification of heteroduplexes and homoduplexes may be used for a variety of analyses, including mutation scanning and SNP genotyping. The term "scanning" refers to the process in which a nucleic acid fragment is compared to a reference nucleic acid fragment to detect the presence of any difference in sequence. A positive answer indicating the presence of a sequence difference may not necessarily reflect the exact nature of the sequence variance or its position on the nucleic acid fragment. The term "genotyping" includes the detection and determination of known nucleic acid sequence variances, including but not limited to, SNPs, base deletions, base insertions, sequence duplications, rearrangements, inversions, base methylations, the number of short tandem repeats; and in the case of a diploid genome, whether the genome is a homozygote or a heterozygote of the sequence variance, as well as the cis/trans positional relationship of two or more sequence variances on a DNA strand (haplotyping).

In another aspect of this invention, various dsDNA binding dyes are identified. The dsDNA binding dyes of the present invention are capable of existing at sufficiently saturating conditions with respect to the DNA during or after amplification, while minimizing the inhibition of PCR. For example, at maximum PCR-compatible concentrations, the dsDNA binding dye has a percent saturation of at least 50%. In other embodiments, the percent saturation is at least 80%, and more particularly, at least 90%. In yet other embodiments, the percent saturation is at least 99%. It is understood that the percent saturation is the percent fluorescence compared to fluorescence of the same dye at saturating concentrations, i.e., the concentration that provides the highest fluorescence intensity possible in the presence of a predetermined amount of dsDNA. Illustratively, the predetermined amount of dsDNA is 100 ng/10 µL which is the amount of DNA produced at the end of a typical PCR at plateau. It is further understood that dye preparations may contain impurities that inhibit amplification. Such impurities should be removed prior to a determination of the percent saturation. It is also understood that the measurement of fluorescence intensity for percent saturation is performed at the wavelength that is well matched for the detection of dye bound to dsDNA, and if possible, not at wavelengths that will detect high background fluorescence from free dye or secondary forms of dye binding which may occur at high dye-to-bp ratio (e.g., binding of dye to the dsDNA-dye complex or to single-stranded nucleic acids).

In yet another aspect of the present invention, the dsDNA binding dye has greater than 50% saturation at maximum PCR-compatible concentrations, and has excitation/emission spectra that would not suggest compatibility with standard real-time PCR instruments. "Standard" instruments for real-time PCR analysis have an excitation range of about 450-490 nm and an emission detection range of about 510-530 nm. It has been found that certain "blue" dyes are compatible with these systems, although their excitation/emission spectra would suggest otherwise. Thus, in this aspect of the invention a method is provided for analysis during or subsequent to PCR using a standard real-time PCR instrument and a dsDNA binding dye having an excitation maximum in the range of 410-465 nm, more particularly in the range of 430-460 nm, and having an emission maximum in the range of 450-500 nm, more particularly in the range of 455-485 nm, as measured in PCR buffer in the presence of dsDNA. Suitable instrumentation may use the excitation/detection ranges above, or may be modified according to the excitation/emission maxima of the dyes. Suitable ranges for detection of the "blue" dyes of this invention as well as for detection of traditional dyes such as fluorescein and SYBR® Green I may include 440-470 nm for excitation and 500-560 for detection.

In one embodiment, the dye is a dye identified as LightCycler Green (or interchangeably, LC Green). Synthesis of LC Green is taught below, and the excitation/emission spectra of LC Green are shown in FIG. 11. Additional properties of LC Green are shown in Table 1. Similarly, other dyes identified as operative in Table 1 may be used within the scope of this invention. While the exact structure of some of these dyes is unknown as of yet, they are believed to be asymmetrical cyanines, and various properties of these fluorescent nucleic acid dyes are shown in Table 1.

While the examples provided herein are directed to melting curve analysis, it is understood that the dyes of the present invention can be used for a variety of real-time quantitative PCR analyses, including quantification of the nucleic acid, determination of initial concentration, testing for the presence of a nucleic acid, multiplexing with labeled probes, and other PCR-based methods.

Furthermore, while reference is made to PCR, other methods of amplification may be compatible with the dyes of this invention. Such suitable procedures include strand displacement amplification (SDA); nucleic acid sequence-based amplification (NASBA); cascade rolling circle amplification (CRCA), Q beta replicase mediated amplification; isothermal and chimeric primer-initiated amplification of nucleic acids (ICAN); transcription-mediated amplification (TMA), and the like. Therefore, when the term PCR is used, it should be understood to include other alternative amplification methods.

Additionally, it is understood that the dsDNA binding dyes include intercalators, as well as other dyes that bind to nucleic acids, as long as the dye differentially binds to double-stranded and single-stranded nucleic acids, or otherwise produces a differential signal based on the quantity of double-stranded nucleic acid.

Thus, the present invention includes one or more of the herein-described double-stranded binding dyes for use in quantitative or qualitative amplification analysis. In one aspect of this invention, a PCR reaction mixture is provided, comprising a target nucleic acid, PCR reagents, oligonucleotide primers configured for amplifying the target nucleic acid, and a dsDNA binding dye having a percent saturation of at least 50%.

In another aspect of this invention, methods are provided for nucleic acid analysis. In one embodiment, a method of genotyping is provided comprising the steps of amplifying the target nucleic acid in the presence of a dsDNA binding dye having a percent saturation of at least 50%, melting the amplified target nucleic acid to generate a melting curve, and identifying the genotype from the melting curve. In another embodiment, a method of mutation scanning is provided comprising the steps of adding a dsDNA binding dye having a percent saturation of at least 50% to a sample comprising a target nucleic acid, amplifying the target nucleic acid in the presence of the dsDNA binding dye, melting the amplified target nucleic acid to generate a melting curve, repeating steps (b) and (c) on second sample to obtain a second melting curve, and comparing the melting curves. In yet another embodiment, a method of PCR analysis is provided comprising the steps of mixing a dsDNA binding dye having a percent saturation of at least 50% with a sample comprising a target nucleic acid and primers configured for amplifying the target nucleic acid, amplifying the target nucleic acid in the presence of the dsDNA binding dye, and monitoring fluorescence of the dsDNA binding dye. Monitoring may occur during amplification, subsequent to amplification, or both.

In yet another aspect of this invention a method is provided comprising the steps of a method of PCR analysis comprising the steps of mixing a dsDNA binding dye with a sample comprising a target nucleic acid and primers configured for amplifying the target nucleic acid, amplifying the target nucleic acid in the presence of the dsDNA binding dye, monitoring fluorescence of the dsDNA binding dye, generating a melting curve for the target nucleic acid, normalizing the melting curve, repeating the mixing, amplifying, normalizing, and generating steps with at least one additional target nucleic acid, and comparing the normalized melting curves.

In an additional aspect of this invention a method is provided for nucleic acid analysis comprising the steps of mixing a target nucleic acid that is at least partially double stranded with a dsDNA binding dye having a percent saturation of at least 50% to form a mixture, and generating a melting curve for the target nucleic acid by measuring fluorescence from the dsDNA binding dye as the mixture is heated.

In a further aspect, kits are provided comprising amplification reagents, oligonucleotide primers configured for amplifying the target nucleic acid, and a dsDNA binding dye having a percent saturation of at least 50%. Any of the dyes discussed herein may be used in the kits.

Various dsDNA binding dyes may be used in the embodiments of this invention, as described herein.

Additional features of the present invention will become apparent to those skilled in the art upon consideration of the following detailed description of illustrative embodiments.

BRIEF DESCRIPTION OF THE DRAWINGS

FIGS. 5A-D show a comparison of genotyping methods; FIG. 5A shows the cystic fibrosis map in which the position of an optional label on a primer is marked (star), FIG. 5B shows genotyping using a labeled primer, FIG. 5C shows genotyping using LightCycler Green, and FIG. 5D shows an attempt to genotype using SYBR® Green I (Homozygotes: --- wt, — F508del, Heterozygotes: --- F508del, --- I507del, ---- F508C).

FIG. 12A shows raw data obtained from high resolution melting of quadruplicate samples of each genotype; FIG. 12B shows normalized high resolution melting curves of the quadruplicate samples of the six genotypes; FIG. 12C shows temperature-shifted, normalized, high resolution melting curves of the quadruplicate samples of the six genotypes. The samples were temperature shifted to overlay the curves between 5 and 10% fluorescence; FIG. 12D shows fluorescence difference curves obtained from the data of FIG. 12C. Each difference curve was obtained by subtracting each sample from the normal (AA) curve to obtain the difference data. While quadruplicate samples were run, due to overlap, fewer than four samples appear in some instances.

Genotype of HLA-A of Utah family 1331 are as follows: A:02011; B:3101; C:2402101; D:03011; E:01011. Each individual is numbered. Female (circle); male (square).

Figure 16A:
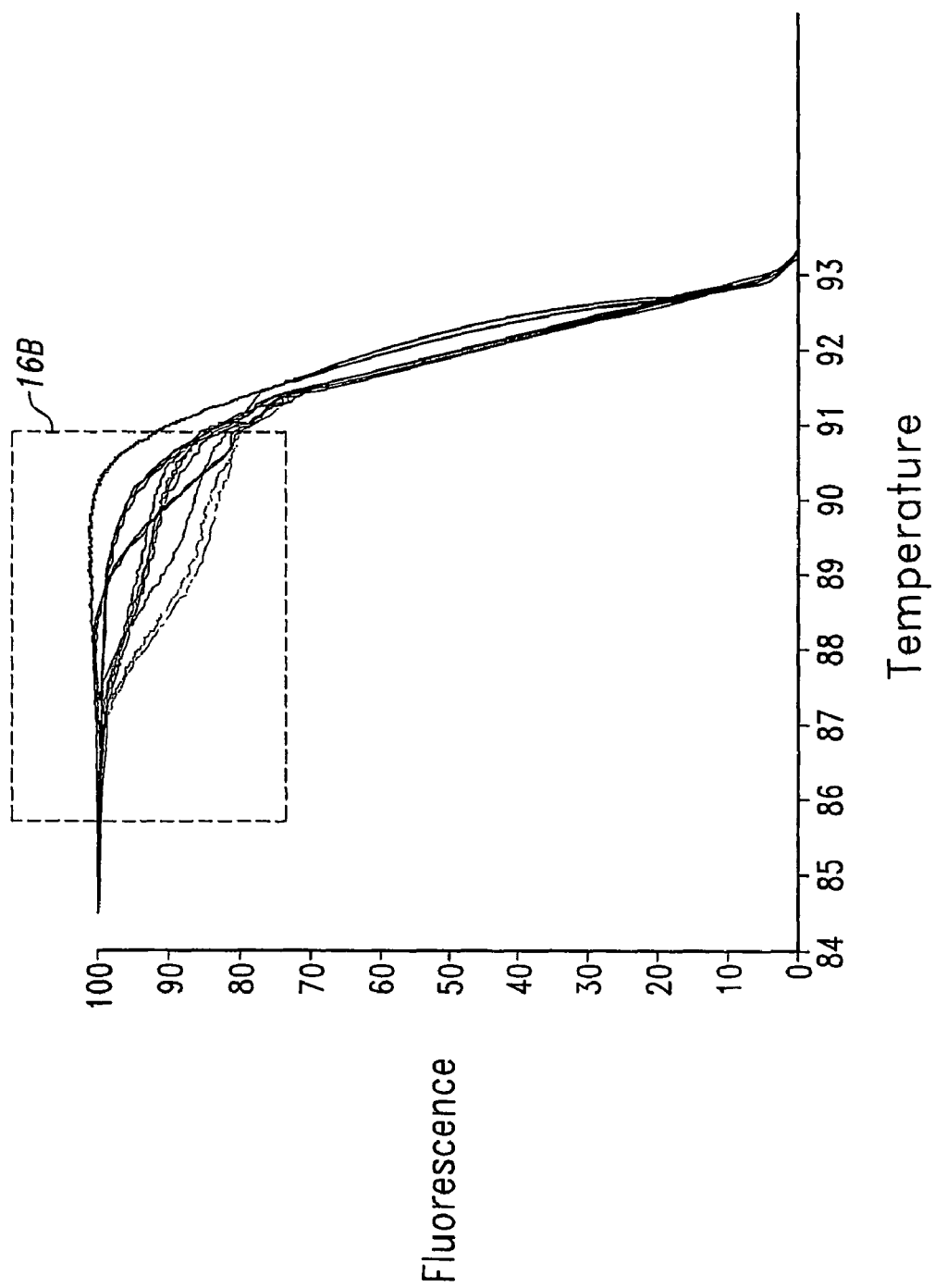
Figure 16B:
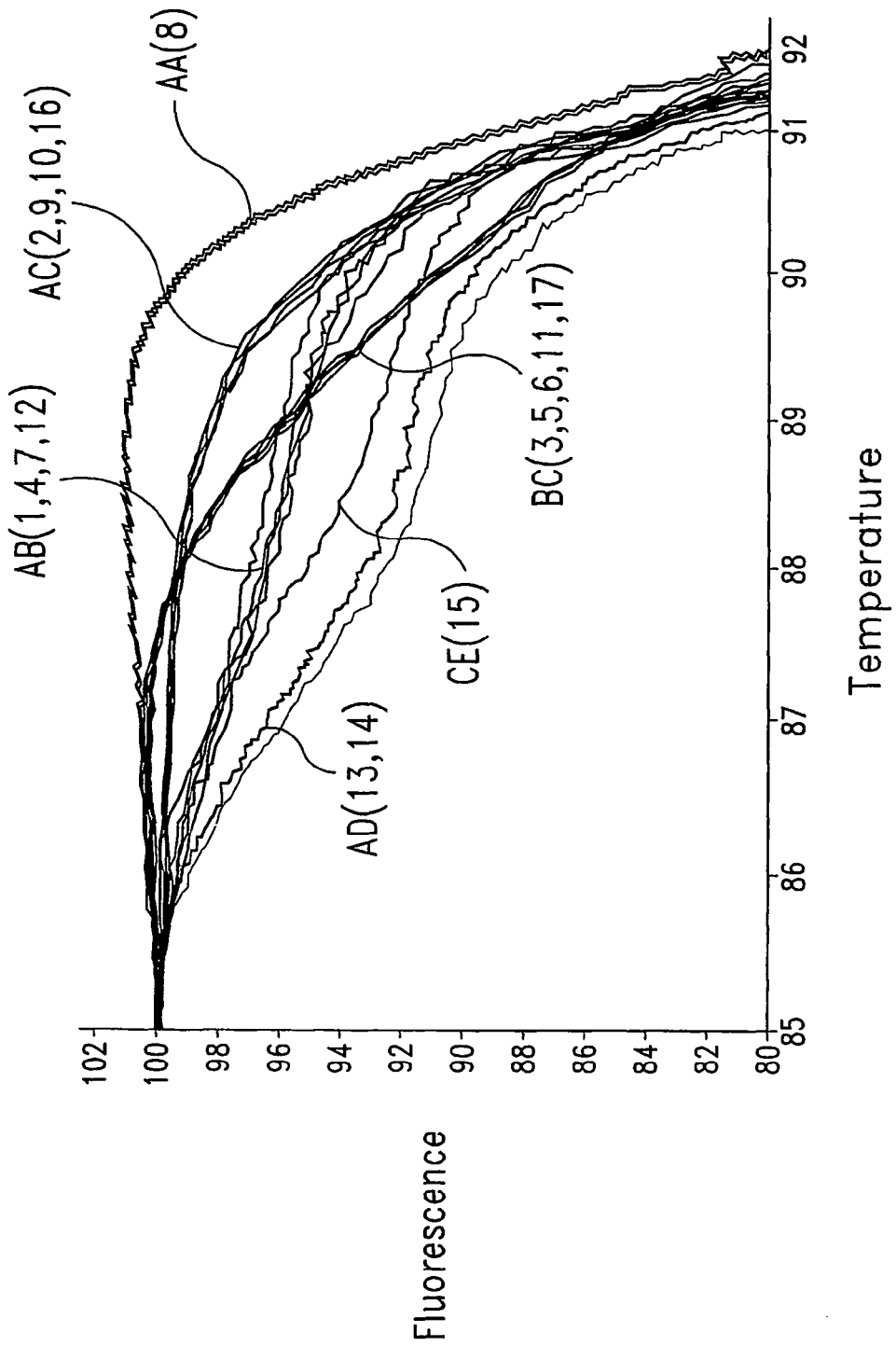

FIGS. 16A and B show the melting curve of Utah family 1331 members. Six different melting curves representing six genotypes in IILA-A exon 2 exist among 17 family members. FIG. 16A shows the full melting curve and FIG. 16B shows an enlarged portion (shown in square in 16A) with the designation of genotype, and designation of individuals in parentheses.

Figure 17:
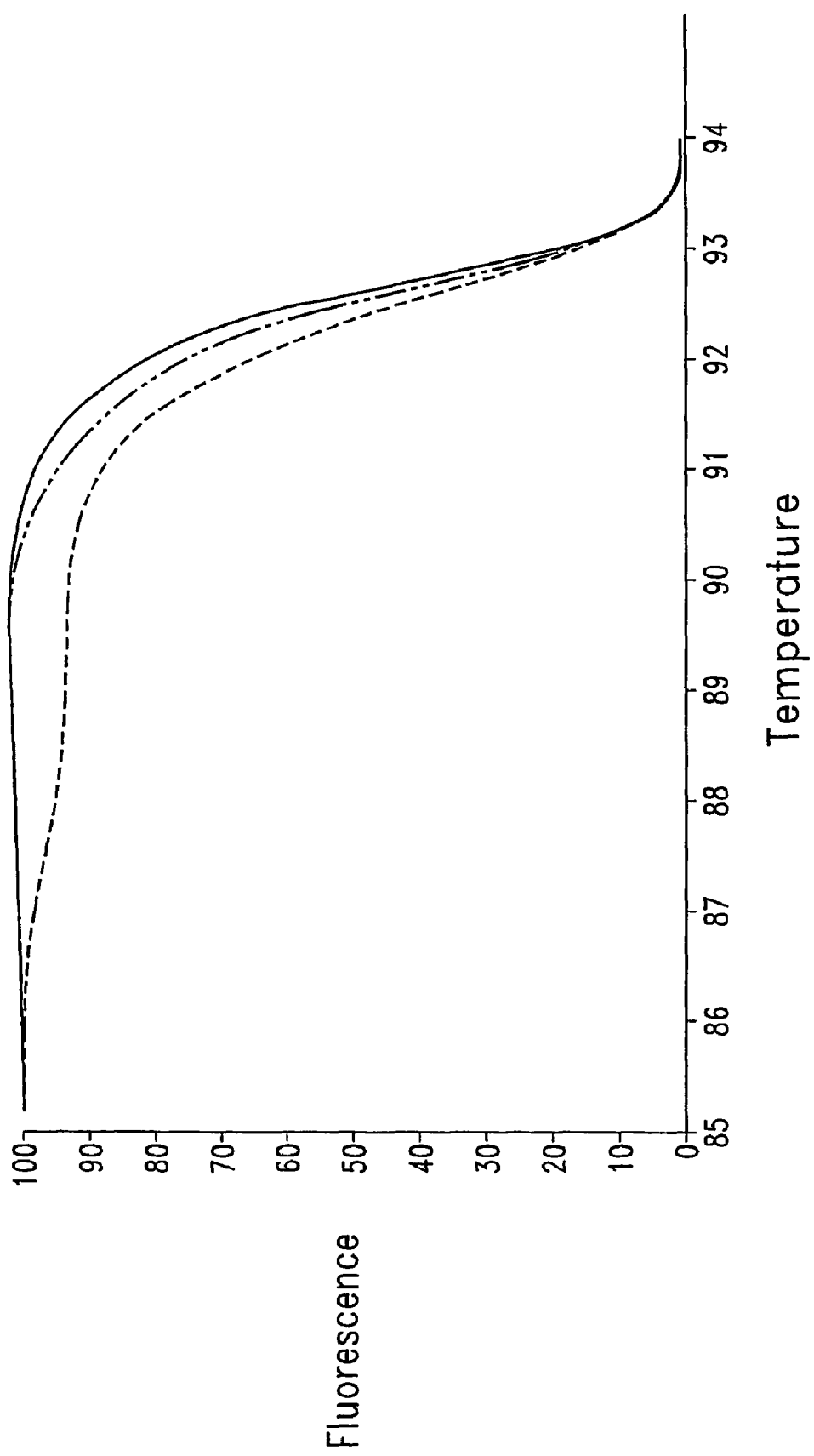

FIG. 17 shows the determination of genotypes of two samples by mixing (— BM15, --- BM16, ---- BM15+ BM16). Two homozygous samples BM15(0101) and BM16 (0201) have a 15-bp difference on the HLA-A exon 2. The melting curve of BM15 and BM16 are similar when taken separately, but when mixed, the 15-bp mismatch shifts the melting curve.

DETAILED DESCRIPTION

SYBR® Green I is a dye extensively used for melting analysis as it shows a large change in fluorescence during PCR (Wittwer C T, et al., Biotechniques 1997;22:130-1, 134-8; Wittwer C T, et al., Real-Time PCR. In: Persing D, et al., eds. Diagnostic Molecular Microbiology: Principles and Applications. ASM Press, 2004: in press). Conceivably, such dyes could be used for both homozygous genotyping and scanning for heterozygous sequence alterations. SYBR® Green I was first used in melting analysis to distinguish different PCR products that differed in Tm by 2° C. or more (Ririe K M, et al., Anal Biochem 1997;245:154-160). Subsequently, SYBR® Green I was used to identify deletions ma T, et al., Clin Chem 2000;46: 119-22), genotype dinucleotide repeats (Marziliano N, et al., Clin Chem 2000;46:423-5), and identify various sequence alterations (Lipsky R H, et al., Clin Chem 2001;47:635-44; Pirulli D, et al., Clin Chem 2000;46: 1842-4; Tanriverdi S, et al., J Clin Microbiol. 2002;40:3237-44; Hladnik U, Clin Exp Med. 2002;2:105-8). However, the Tm difference between genotypes can be small and may challenge the resolution of current instruments. Indeed, it has been suggested that SYBR® Green I, "should not be used for routine genotyping applications" (von Ahsen N, et al., Clin Chem 2001;47:1331-1332). Melting curve genotyping with commonly used double-strand-specific DNA dyes can include an increased Tm with broadening of the melting transition (Douthart R J, et al., Biochemistry 1973;12:214-20), and compression of the Tm difference between genotypes (FIG. 5D). These factors lower the potential of SYBR® Green I for genotype discrimination.

Amplification of heterozygous DNA produces four different single strands that create two homoduplex and two heteroduplex products when denatured and cooled. Theoretically, all four products have different Tms and the melting curve should be a composite of all four double-stranded to single-stranded transitions. However, double-strand-specific DNA dyes may redistribute during melting (Aktipis S, et al., Biochemistry 1975;14:326-31), causing release of the dye from low melting heteroduplexes and redistribution to higher melting homoduplexes. Because SYBR® Green I is not saturating at concentrations compatible with PCR (Wittwer C T, et al., Biotechniques 1997;22:130-1, 134-8; FIG. 9), such redistribution is plausible and consistent with the absence of a heteroduplex transition (FIG. 5D).

LightCycler Green and other dyes of the present invention can be used for genotyping and scanning applications. When only one PCR product is amplified and the sequence is homozygous, only homoduplexes are formed. With the dyes of the present invention, Tm differences between different homoduplex genotypes are not compressed (FIG. 5C), and clear differentiation between genotypes is possible. The dyes of the present invention can also identify and distinguish multiple products present in a reaction, illustratively homoduplexes generated from amplification of multiple loci or multiple targets that are homozygous. In contrast, most of the time only a few products can be observed with SYBR® Green I, presumably due to dye redistribution (see FIG. 7A).

When one or more heterozygous targets are amplified, heteroduplex products are readily observable with the dyes of the present invention. The ability to detect and identify heteroduplexes is particularly useful for detecting heterozygous genotypes as well as for scanning unknown mutations. This is not possible with conventional dsDNA dyes used in real-time PCR, such as SYBR® Green I, SYBR® Gold, and ethidium bromide, where heteroduplex products are not observable.

Figure 2:
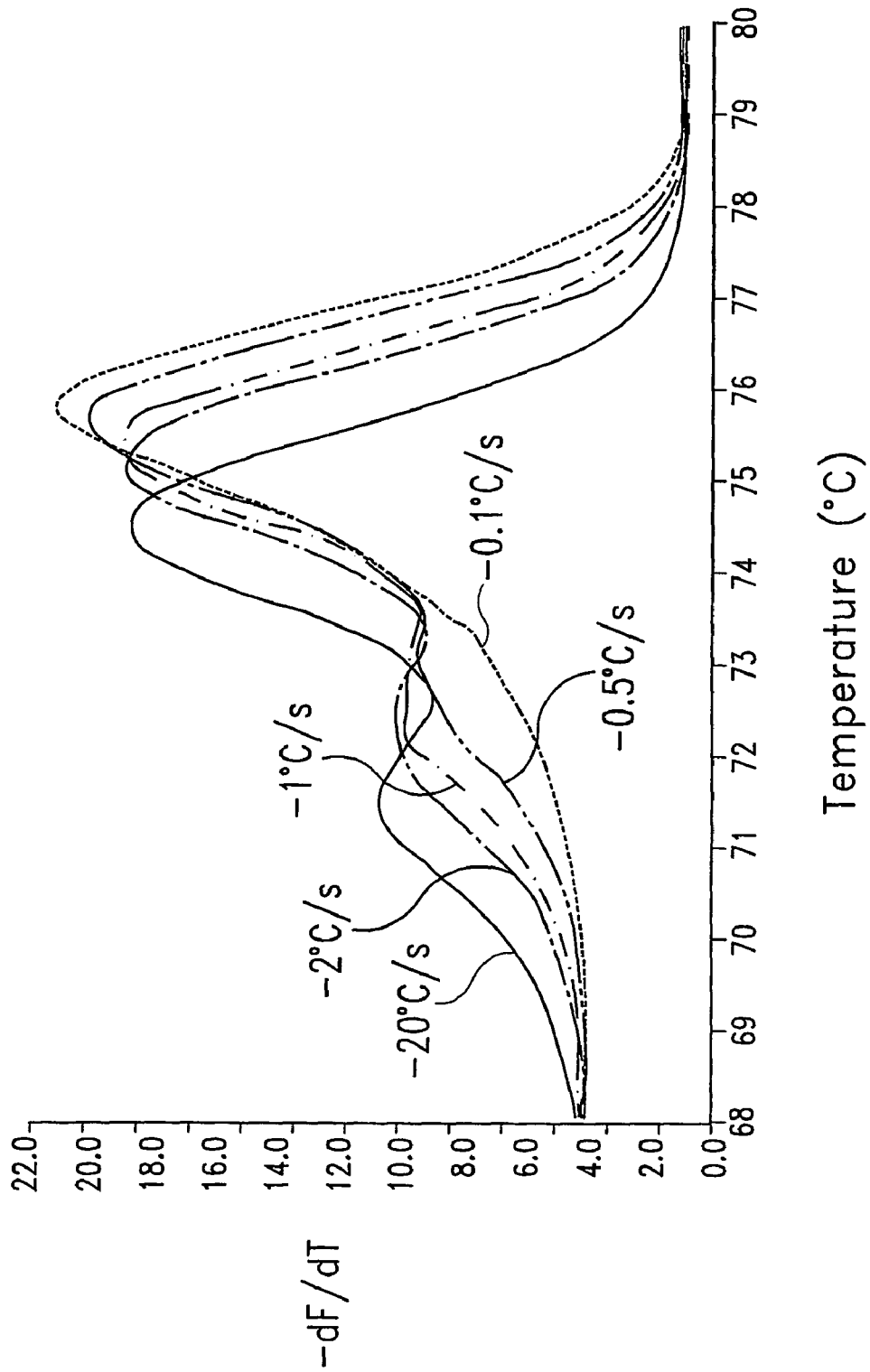
FIG. 2 shows the effect of cooling rates prior to melting analysis on the detection of heteroduplexes.

Heteroduplex strands may re-associate with their perfect complement and form homoduplexes during melting. Because the concentration of products at the end of PCR is high, this re-association happens rapidly. Re-association can be minimized by limiting the time the products are near their melting temperatures, particularly between the Tms of the heteroduplex and homoduplex products. In addition to strand re-association during melting, the selective hybridization of a strand to either its perfect match, or to its mismatched complementary strand, is influenced by cooling rates. Under conditions presented herein, heteroduplex formation is most favored by rapid cooling and often disappears at rates slower than −0.1° C./s (FIG. 2). This is in contrast to denaturing HPLC techniques, where cooling rates are much slower (−0.01 to about −0.02° C./s), yet heteroduplexes are efficiently formed (Xiao W, et al., Hum Mutat 2001;17:439-74). Perhaps the relative rates of homoduplex and heteroduplex formation are strongly dependent on product size, and the results obtained using small amplicons may not be typical for the larger products more commonly used in dHPLC.

The discrimination between homozygous genotypes can be improved by melting at slower rates, at the expense of greater analysis time. One source of potential error in melting curve genotyping is the effect of DNA concentration on Tm. Using a random 100 bp amplicon of 50% GC content under PCR conditions, the difference in Tm between products at 0.05 μM and 0.5 μM is about 0.7° C. (von Ahsen N, et al., Clin Chem 2001;47:1956-61; Wetmur J G, Crit Rev Biochem Mol Biol 1991;26:227-59). This change can be important when the Tms of different homozygous genotypes are very close. However, different PCR samples tend to plateau at the same product concentration, so post-amplification concentration differences are usually minimal. Also, it may be possible to estimate amplicon concentrations by real-time fluorescence and adjust the Tms for even greater genotyping precision. Alternatively, asymmetric PCR may be used to limit automatically the final concentration of PCR product.

With LightCycler Green, it is possible to distinguish all single base heterozygotes from homozygotes. In the detection of heterozygotes, the absolute melting temperature and the influence of DNA concentration are not as important as with methods involving differentiation between homozygous genotypes. Heteroduplexes affect the shape of the melting curve, particularly at the "early," low temperature portion of the transition. Different melting curves can be temperature matched by translating the X-axis to superimpose the "late," high temperature portion of the transition. The presence or absence of heteroduplexes can then be inferred with greater accuracy.

Whatever the precision of the instrument, some genotypes will be nearly identical in Tm. One way to detect homozygous variants with the same Tm is to mix the variants together. The resulting heteroduplexes will melt at lower temperatures than the homoduplexes, displayed as a drop in the normalized melting curves before the major melting transition.

Figure 7A:
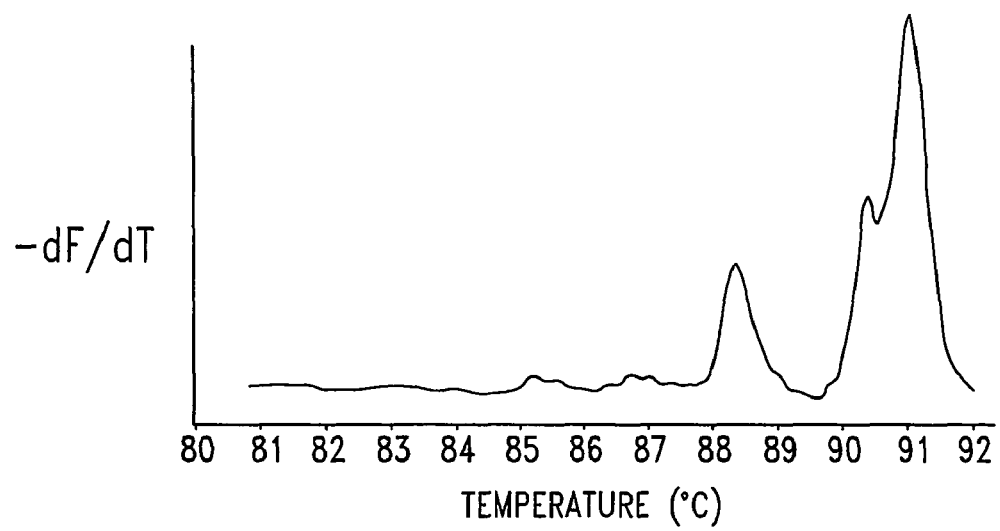
FIGS. 7A-B shows derivative melting curves of DNA mixtures using SYBR® Green I (FIG. 7A) and LightCycler Green (FIG. 7B).
Figure 7B:
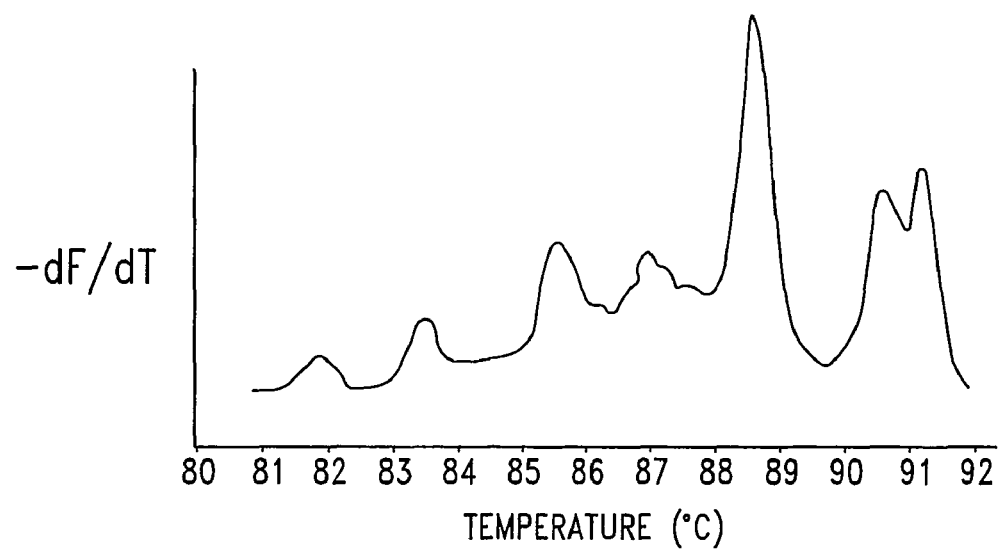

Thus, using presently available PCR amplification devices, LightCycler Green can identify heteroduplexes in melting curve transitions that cannot currently be identified using SYBR® Green I. One possible reason why SYBR® Green I cannot easily identify low melting transitions is shown in FIG. 7A. When several DNA fragments of increasing stability are present, the low temperature peaks are very small with SYBR® Green I compared to LightCycler Green. During melting, SYBR® Green I may be released from low temperature duplexes, only to attach to duplexes that melt at higher temperatures. This causes each successive peak to be higher than the last, with the lowest temperature peaks being very small, if observable at all. As seen in FIG. 7B, Low temperature melting products are easily detected with LightCycler Green, but not by SYBR® Green I.

The advantages of using LC Green have led to identification of other dsDNA dyes that are compatible with PCR and are suited for genotyping at PCR-compatible concentrations. Many of the dyes useful in the method of the present invention belong to a family of cyanines. Cyanine dyes are those dyes containing one or more divalent moieties "—C(R)=" arranged in a chain that link two nitrogen containing heterocycles. The group "R" may be hydrogen or any carbon substituent, and is illustratively hydrogen or alkyl, including $C_{1-6}$ alkyl, which may be optionally substituted. It is understood that in cyanine dyes where there is more than one divalent moiety "—C(R)=" each "R" may be selected independently. Such cyanine dyes may be monomers or dimers, as further defined by the illustrative general formulae herein described. In addition to cyanine dyes, it is contemplated herein that other families of dsDNA binding dyes are also useful in the PCR reaction mixtures, methods, and compositions described herein, including but not limited to phenanthridinium intercalators and phenanthroline-based metallointercalators.

Illustrative dyes useful in the present PCR reaction mixtures, methods, and compositions include, PO-PRO™-1, BO-PRO™-1, SYTO® 43, SYTO® 44, SYTO® 45, SYTOX® Blue, POPO™-1, POPO™-3, BOBO™-1, BOBO™-3, LO-PRO™-1, JO-PRO™-1, YO-PRO®-1, TO-PRO®-1, SYTO® 11, SYTO® 13, SYTO® 15, SYTO® 16, SYTO® 20, SYTO® 23, TOTO™-3, YOYO®-3 (Molecular Probes, Inc., Eugene, Oreg.), GelStar® (Cambrex Bio Science Rockland Inc., Rockland, Me.), thiazole orange (Aldrich Chemical Co., Milwaukee, Wis.) and novel dyes G5, H5, D6, E6, P6, R6, Y6, Z6, and D8 described herein.

Illustrative cyanine dyes for use in the PCR reaction mixtures, methods, and compositions described herein also include monomers or dimers of unsymmetrical cyanines having pyridinium, pyrimidinium, quinolinium, isoquinolinium, or purinium core structures, and those generally described by Formula I:

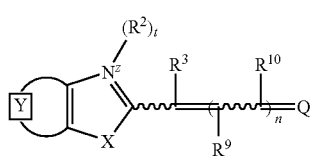

Formula I wherein the moiety ⊡ represents an optionally-substituted fused mono or polycyclic aromatic or nitrogen-containing heteroaromatic ring;

X is oxygen, sulfur, selenium, tellurium, or a group selected from $C(CH_3)_2$ and $NR^1$, where $R^1$ is hydrogen or alkyl, including $C_{1-6}$ alkyl and $C_{2-6}$ alkyl;

$R^2$ is alkyl, including $C_{1-6}$ alkyl and C2-6 alkyl, cycloalkyl, including $C_{3-8}$ cycloalkyl, aryl, arylalkyl, including aryl($C_{1-2}$ alkyl), hydroxyalkyl, alkoxyalkyl, aminoalkyl, mono and dialkylaminoalkyl, trialkylammoniumalkyl, alkyl and arylcarbonyl, alkyl and arylcarboxamide, alkyl and arylsulfonyl, alkylenecarboxylate, alkylenecarboxamide, alkylenesulfonate, alkylenesulfonic acid, and the like, a cyclic heteroatom-containing moiety, or an acyclic heteroatom-containing moiety, each of which may be optionally substituted; illustrative heteroatom-containing moieties include optionally substituted heteroalkyl, including methoxymethyl, ethoxyethyl, and the like, heterocyclyl, including piperidinyl, and the like, alkyl and arylsulfonates, including methylsulfonate, 4-chlorophenylsulfonate, and the like, alkoxy, including methoxy, ethoxy, and the like, amino, including methylamino, dimethylamino, and the like, carbonyl derivatives, including alkyl and aryl carbonyl, alkylaminocarbonyl, alkoxycarbonyl, and the like, heteroalkenyl, including alkenylaminoalkyl, alkenyloxyalkyl, alkylaminoalkenyl, alkyloxyalkenyl, alkylideneaminoalkyl, and the like, heteroallyl, esters, amines, amides, phosphorus-oxygen, and phosphorus-sulfur bonds; and including heteroatom-containing moieties as described in U.S. Pat. No. 5,658,751 and PCT Publication No. WO 00/66664; the disclosures of each are herein incorporated in their entirety by reference;

t=0 or 1;

Z is a charge selected from 0 or 1;

$R^3$, $R^9$, and $R^{10}$ are each independently selected from hydrogen and alkyl, including $C_{1-6}$ alkyl and C2-6 alkyl;

n=0, 1, or 2; and

Q is a heterocycle, such as a pyridinium, a pyrimidinium, a quinolinium, or a purinium, each of which may be optionally substituted.

The term "alkyl" as used herein generally refers to a linear or optionally branched hydrocarbon moiety comprising from 1 to about 12 carbon atoms, illustratively including but not limited to methyl (Me), ethyl, propyl, butyl, dodecyl, 4-ethylpentyl, and the like.

The term "cycloalkyl" as used herein generally refers to a linear or optionally branched hydrocarbon moiety, at least a portion of which forms one or two rings, comprising from 3 to about 14 carbon atoms, illustratively including but not limited to cyclopropyl, cyclopentyl, cyclohexyl, 4-methylcyclohexyl, 2,3-dimethylcyclopentyl, 3,5-dimethylcyclohexylethyl, and the like.

The term "aryl" as used herein generally refers to a cyclic aromatic moiety, illustratively including but not limited to phenyl (Ph), naphthyl, furyl, thienyl, pyrrolo, pyrazolo, isoxazolyl, isothiazolyl, oxazolyl, thiazolyl, pyridinyl, pyridazinyl, pyrimidinyl, pyrazinyl, quinolinyl, isoquinolinyl, quinoxalinyl, quinazalinyl, and the like.

The term "optionally substituted" as used herein generally refers to the optional replacement of one or more hydrogen atoms present on the parent group, including those present on carbon, nitrogen, oxygen, or sulfur atoms, with a substituent, such as halo; hydroxy; amino; thio; alkyl, cycloalkyl, haloalkyl, halocycloalkyl; alkoxy, cycloalkoxy, haloalkoxy; monoalkyl and dialkylamino; aminoalkyl; monoalkyl and dialkylaminoalkyl; alkylthio; alkyl, haloalkyl, cycloalkyl, and arylcarbonyl; alkyl, haloalkyl, cycloalkyl, and arylcarbonyloxy; alkyl, haloalkyl, cycloalkyl, and arylsulfonyl; and carboxyl derivatives, such as carboxylic acids, esters, and amides. It is appreciated that the replacement of proximal hydrogen atoms, including geminal and vicinal hydrogens, may be such that the substituents replacing those proximal hydrogens are taken together to form a spiro ring or a fused ring, respectively.

It is appreciated that each of the above described terms may be used in combination in chemically relevant ways to refer to other moieties, such as arylalkyl referring to an aryl group as defined herein linked to an alkyl group as defined herein to form structures including, but not limited to, benzyl, phenethyl, picolinyl, 3,5-dimethoxypicolinyl-4-yl, and the like.

It is appreciated that the cyanine dye structures described herein may contain chiral centers. In those cases, all stereoisomers are understood to be included in the description of these cyanine dye structures, unless otherwise indicated. Such stereoisomers include pure optically active isomers, racemic mixtures, and mixtures of diastereomers containing any relative amount of one or more stereoisomeric configurations.

It is also appreciated that the cyanine dye structures described herein may contain geometric centers. In those cases, all geometric isomers are understood to be included in the description of the cyanine dye structures, unless otherwise indicated. Such geometric isomers include cis, trans, E and Z isomers, either in pure in various mixtures of geometric configurations. It is also understood that depending upon the nature of the double bond contained in the cyanine dye structures, such double bond isomers may interconvert between cis and trans, or between E and configurations depending upon the conditions, such as solvent composition, solvent polarity, ionic strength, and the like.

It is further appreciated that when the charge Z is greater than 0, several tautomers of the compounds of Formula I may exist, including mixtures of such tautomers. Illustratively, the charge Z may be formally localized on the nitrogen atom as depicted in Formula I, or on one of the carbon atoms forming the polyene linker that connects the two heterocycles, or alternatively, the charge may be localized on the heterocycle Q. Tautomers of the charged compounds of Formula I may be depicted by rearranging the double bond-single bond configuration of compounds of Formula I, such as the illustrative structures:

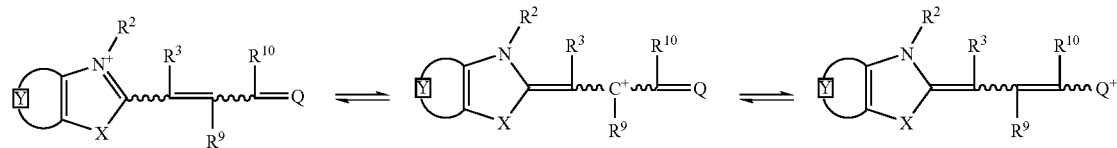

wherein ⊠, X, $R^2$, $R^3$, $R^9$, $R^{10}$, and Q, are as defined for Formula I, and t=1, Z=1, and n=1. The cyanine dye compounds described herein include any of the several possible tautomers, or various equilibrium mixtures of those tautomers. It is understood that the location of the formal charge is influenced by the nature of the moieties ⊠, X, $R^2$, $R^3$, $R^9$, $R^{10}$, and Q. It is further understood that the favored tautomer or equilibrium mixture of tautomers may depend upon conditions, such as solvent composition, solvent polarity, ionic strength, formulation, and the like. It is understood that the term "resonance structures" also refers to these various charge localizations and is equally descriptive of formulae illustrated above.

It is also understood that when compounds of Formula I carry a net charge, such as where Z is 1, or where there is present on the compounds of Formula I a charged substituent, such as an ammonium group, or a sulfonic acid group, these compounds of Formula I are accompanied by a counter ion. Any monovalent, divalent, or polyvalent counter ion is included in the description of the cyanine dye structures contained herein. Illustrative counter-ions include negatively charged counter ions such as iodide, chloride, bromide, hydroxide, oxide, acetate, trifluoroacetate, monophosphate, diphosphate, triphosphate, and the like, and positively charged counter ions such as lithium, sodium, potassium, cesium, ammonium, polyalkylammonium, and the like. Such counter ions may arise from the synthetic methods used, the purification protocol, or other ion exchange processes.

It is believed that the nature or type of counter ion does not appear to influence the functionality of the cyanine dyes described herein. It is appreciated that when the dyes described herein are dissolved in solvents or other media used to practice the PCR reaction mixtures, methods, and compositions described herein, the accompanying counter ion may exchange with other counter ions that are present in the solvents or other media. Such additional counter ions may be solvent ions, salts, buffers, and/or metals.

It is appreciated that the group $R^2$ may be virtually any group that arises from the nucleophilic reaction between the parent compound of Formula I, where t=Z=0:

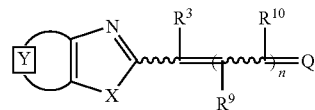

and a compound having the formula $R^2$-L, wherein L is a suitable leaving group, and $R^2$ is as defined above. Illustratively, $R^2$ is an optionally substituted alkyl, acyl, aryl, sulfonic acid, or sulfonyl group, each of which may be optionally substituted. Illustrative leaving groups L include, but are not limited to halides, such as chloride and bromide, acylates, such as acetate, formate, and trifluoroacetate, sulfonates, such as methylsulfonate, trifluoromethylsulfonate, and tolylsulfonate, sulfates, such as methylsulfate, and the like.

In one illustrative embodiment, Q is an heterocycle such as, but not limited to:

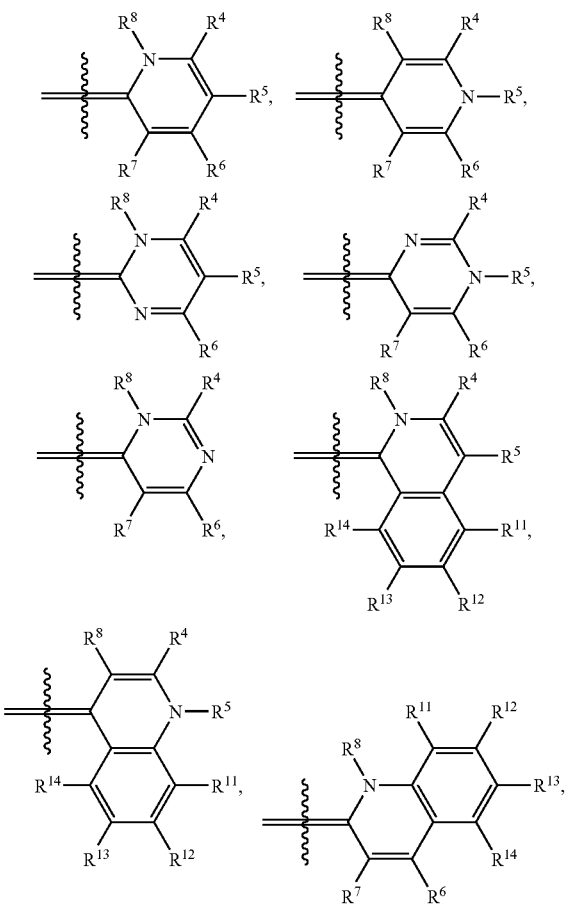

-continued

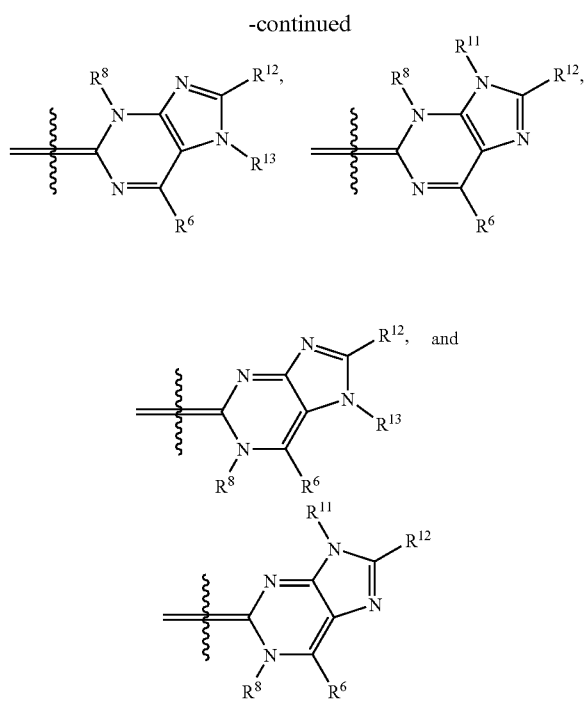

wherein $R^4$, $R^5$, $R^6$, $R^7$, $R^8$, $R^{11}$, $R^{12}$, $R^{13}$, and $R^{14}$ are each independently selected from the group consisting of hydrogen, halogen, alkyl, cycloalkyl, heteroalkyl, heterocycloalkyl, alkenyl, polyalkenyl, alkynyl, polyalkynyl, alkenylalkynyl, aryl, heteroaryl, alkoxy, alkylthio, and dialkylamino, each of which may be optionally substituted.

In another illustrative embodiment, one of $R^4$, $R^5$, $R^6$, $R^7$, $R^8$, $R^{11}$, $R^{12}$, $R^{13}$, and $R^{14}$ is an heteroatom-containing moiety, as described in U.S. Pat. No. 5,658,751. In another illustrative embodiment, one of $R^4$, $R^5$, $R^6$, $R^7$, $R^8$, $R^{11}$, $R^{12}$, $R^{13}$, and $R^{14}$ is a reactive group, including but not limited to halogens, hydroxy, alkoxides, amines, carboxylic acids, halides, alcohols, aldehydes, thiols, alkyl, and arylthiols, alkyl and arylsulfonyls, succinimidyl esters, ketones, and isothiocyanates that may be used to attach moieties to the dye core structure, illustratively through the formation of carbon-carbon bonds, amines, amides, ethers, thioethers, disulfides, ketones, thioureas, and Schiff bases. In another illustrative embodiment, one of $R^4$, $R^5$, $R^6$, $R^7$, $R^8$, $R^{11}$, $R^{12}$, $R^{13}$, and $R^{14}$ is a BRIDGE-DYE having the formula:

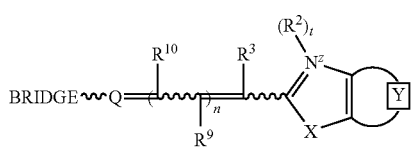

wherein a ⊠, X, $R^2$, t, Z, $R^3$, $R^9$, $R^{10}$, Q, and n are as defined for Formula I, and BRIDGE is a single covalent bond, or a covalent linkage that is linear or branched, cyclic or heterocyclic, saturated or unsaturated, having 1-16 non-hydrogen atoms such as carbon, nitrogen, phosphate, oxygen, and sulfur, such that the linkage contains any combination of akyl, ether, thioether, amine, ester, or amide bonds; single, double, triple, or aromatic carbon-carbon bonds; phosphorus-oxygen, phosphorus-sulfur, nitrogen-nitrogen, or nitrogen-oxygen bonds; or aromatic or heteroaromatic bonds. It is appreciated that in some embodiments, this dimeric structure is symmetrical about BRIDGE, and in other embodiments, this dimeric structure is unsymmetrical about BRIDGE, wherein for example, any of ⊠, X, $R^2$, t, Z, $R^3$, $R^9$, $R^{10}$, and n are each independently selected in each occurrence on each side of BRIDGE.

Illustrative dyes for use in the present invention also include cyanine dyes of Formula I having a pyridinium or pyrimidinium core structure wherein X is oxygen or sulfur; the moiety ⊠ represents an optionally-substituted fused benzo, optionally-substituted fused naphthaleno, optionally-substituted fused pyridino, optionally-substituted fused pyrimidino, optionally-substituted fused quinolino, and the like; n=0 or 1; t=0 or 1; $R^2$ is alkyl, such as methyl and ethyl, optionally substituted aryl, such as phenyl or tolyl, an alkylenesulfonate, such as propylenesulfonic acid, or alkylsulfonyl, such as $CH_3(CH_2)_mSO_2$, where m is 0, 1, 2, or 3; and Q is an heterocycle selected from the group of structures consisting of:

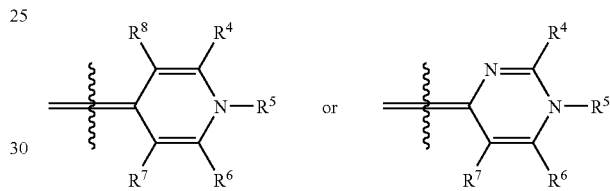

wherein $R^4$ is hydrogen, alkoxy, including methoxy, ethoxy, propyloxy, and the like; alkylthio, including methylthio, ethylthio, and the like; heterocyclylalkyl, including optionally substituted piperidinyl, pyrrolidinyl, piperazinyl, and the like; or heterocyclylalkyl including a charged group, including 4,4-dimethylpiperazinium-1-yl, and the like; or a reactive group, including halo, hydroxy, alkoxy, thio, alkyl and arylthio, alkyl and arylsulfonyl, amino, formyl, alkyl and arylcarbonyl, carboxyl derivatives, and the like;

$R^5$ is $C_{1-6}$ alkyl, including methyl, ethyl, butyl, sec-butyl, isobutyl, and the like; optionally substituted phenyl; or $(CH_2)_3{}^+(Me)_3$; and $R^6$, $R^7$, and $R^8$ are each independently hydrogen or methyl.

Illustrative dyes for use herein also include cyanine dyes of Formula I having a pyridinium or pyrimidinium core structure wherein X is oxygen or sulfur; the moiety ⊠ represents an optionally-substituted fused benzo, forming an optionally substituted benzoxazolium or benzthiazolium ring, or an optionally-substituted fused naphtho, forming an optionally substituted naphthoxazolium or naphthothiazolium ring; n=0 or 1; t=0 or 1; $R^2$ is alkyl, such as methyl, aryl, such as phenyl or tolyl, an alkylenesulfonate, such as propylenesulfonic acid, or alkylsulfonyl, such as $CH_3(CH_2)_mSO_2$, where m is 0, 1, 2, or 3; and Q is a 4-pyridinium or 4-pyrimidinium heterocycle.

Illustrative dyes for use herein also include cyanine dyes useful in the PCR reaction mixtures, methods, and compositions described herein with quinolinium core structures, and generally described by Formula II:

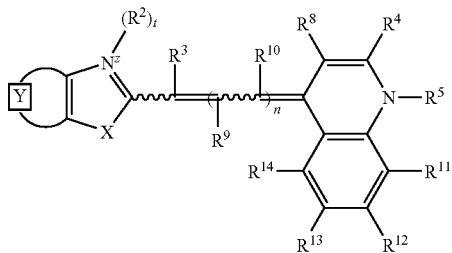

Formula II wherein the moiety ⊡ represents an optionally-substituted fused mono or polycyclic aromatic or nitrogen-containing heteroaromatic ring;

X is oxygen, sulfur, or a group selected from $C(CH_3)_2$, and $NR^1$, where $R^1$ is hydrogen or $C_{1-6}$ alkyl;

$R^2$ is alkyl, including $C_{1-6}$ alkyl and C2-6 alkyl, cycloalkyl, including $C_{3-8}$ cycloalkyl, aryl, arylalkyl, an alkylenesulfonate, a cyclic heteroatom-containing moiety, or an acyclic heteroatom-containing moiety, each of which may be optionally substituted;

t=0 or 1;

Z is a charge selected from 0 or 1;

$R^3$, $R^9$, and $R^{10}$ are each independently selected from hydrogen and alkyl, including $C_{1-6}$ alkyl;

n=0, 1, or 2; and $R^4$, $R^5$, $R^8$, $R^{11}$, $R^{12}$, $R^{13}$, and $R^{14}$ are as described herein for Formula I, providing that $R^4$ is a moiety with a molecular weight of less than about 115, or illustratively a molecular weight of less than about 105.

Illustrative dyes for use in the present invention also include cyanine dyes of Formula II wherein the moiety ⊡ represents an optionally-substituted fused benzo, thereby forming a benzoxazolium or benzthiazolium ring; X is oxygen or sulfur; n=0 or 1; t=0 or 1; $R^2$ is methyl;

$R^4$ is hydrogen, $C_{1-6}$ alkyl, including methyl, or optionally-substituted phenyl;

$R^5$ is $C_{1-6}$ alkyl, including methyl, or optionally-substituted phenyl;

$R^8$ is hydrogen, and $R^{11}$, $R^{12}$, $R^{13}$, and $R^{14}$ are hydrogen or alkoxy, including methoxy.

In other embodiments, dyes for use in the present invention also illustratively include cyanine dyes of Formula II wherein the moiety ⊡ represents an optionally-substituted heterocycle, including 1-methylpyrido and 3-bromo-1-methylpyrido; X is oxygen or sulfur; n=0 or 1; t=z=0;

$R^4$ is hydrogen or $C_{1-6}$ alkyl, including methyl;

$R^5$ is $C_{1-6}$ alkyl, including methyl, optionally-substituted phenyl or heteroalkyl, including heteroalkyl having a charged group such as the group —$(CH_2)_3N(Me)_3$;

$R^8$ is hydrogen; and $R^{11}$, $R^{12}$, $R^{13}$, and $R^{14}$ are hydrogen, alkyl, including methyl, or alkoxy, including methoxy.

In another embodiment, two compounds of Formula I are taken together to form a dimer. The two compounds are linked to each other by replacing one of the substituents $R^4$, $R^5$, $R^6$, $R^7$, $R^8$, $R^{11}$, $R^{12}$, $R^{13}$, and $R^{14}$, as defined above, present on each of the compounds of Formula I with a single divalent linker. Illustratively, two compounds of Formula I are taken together to form a dimer, where the two $R^5$ substituents present on the two compounds of Formula I are replaced with a single divalent linker. It is appreciated that both symmetrical and unsymmetrical dimers of Formula I compounds are contemplated herein. In the case of unsymmetrical dimers of compounds of Formula I, it is understood that such asymmetry may arise by forming dimers from compounds of Formula I having different substitution patterns, or having different heterocycles Q. Further, such asymmetry may arise by forming dimers from compounds of Formula I where different substituents are replaced with the divalent linker, such as illustratively replacing $R^5$ on a first compound of Formula I and replacing $R^8$ on a second compound of Formula I with the divalent linker.

In another embodiment, two compounds of Formula II are taken together to form a dimer. The two compounds are linked to each other by replacing one of the substituents $R^4$, $R^5$, $R^8$, $R^{11}$, $R^{12}$, $R^{13}$, and $R^{14}$, as defined above, present on each of the compounds of Formula II with a single divalent linker. Illustratively, two compounds of Formula II are taken together to form a dimer, where the two $R^5$ ituents present on the two compounds of Formula II are replaced with a single divalent linker. It is appreciated that both symmetrical and unsymmetrical dimers of Formula II compounds are contemplated herein. In the case of unsymmetrical dimers of compounds of Formula II, it is understood that such asymmetry may arise by forming dimers from compounds of Formula II having different substitution patterns, or having different heterocycles Q. Further, such asymmetry may arise by forming dimers from compounds of Formula II where different substituents are replaced with the divalent linker, such as illustratively replacing $R^5$ on a first compound of Formula II and replacing $R^8$ on a second compound of Formula II with the divalent linker.

The dimeric cyanine dye structures formed by compounds of Formula I may also be represented by Formula III:

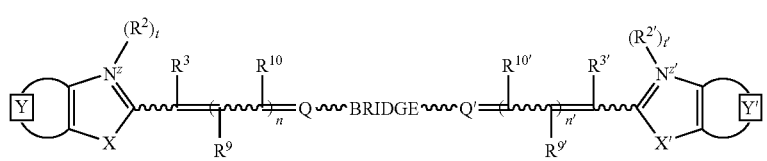

Formula III wherein the moieties ⊡ and ⊡ each represent an independently selected optionally-substituted fused mono or polycyclic aromatic or nitrogen-containing heteroaromatic ring;

X and X' are each independently selected from oxygen, sulfur, selenium, tellurium, or a group selected from $C(CH_3)_2$, $NR^1$, or $NR^{1'}$, where $R^1$ and $R^{1'}$ are each independently hydrogen or $C_{1-6}$ alkyl;

$R^2$ and $R^{2'}$ are each independently selected from alkyl, including $C_{1-6}$ alkyl, cycloalkyl, including $C_{3-8}$ cycloalkyl, aryl, arylalkyl, including aryl($C_{1-2}$ alkyl), a cyclic heteroatom-containing moiety, or an acyclic heteroatom-containing moiety, each of which may be optionally substituted;

t=0 or 1;

t'=0 or 1;

Z and Z' are each a charge independently selected from 0 or 1;

$R^3$, $R^9$, $R^{10}$, $R^{3'}$, $R^{9'}$, and $R^{10'}$ are each independently selected from hydrogen and alkyl, including $C_{1-6}$ alkyl;

n=0, 1, or 2;

n'=0, 1, or 2;

BRIDGE is a divalent linker comprising 2 to about 30 divalent units selected from alkylene, heteroalkylene, alkylamindiyl, alkylalkylammoniumdiyl, and the like, such as $(CH_2)_p$, $(CH_2)_pN^+Me_2(CH_2)_q$, $(CH_2)_pN^+Me_2(CH_2)_qN^+Me_2(CH_2)_r$, and the like, where p, q, and r are each independently selected from 1, 2, and 3; and Q and Q' are heterocycles, each independently selected from the group of structures consisting of:

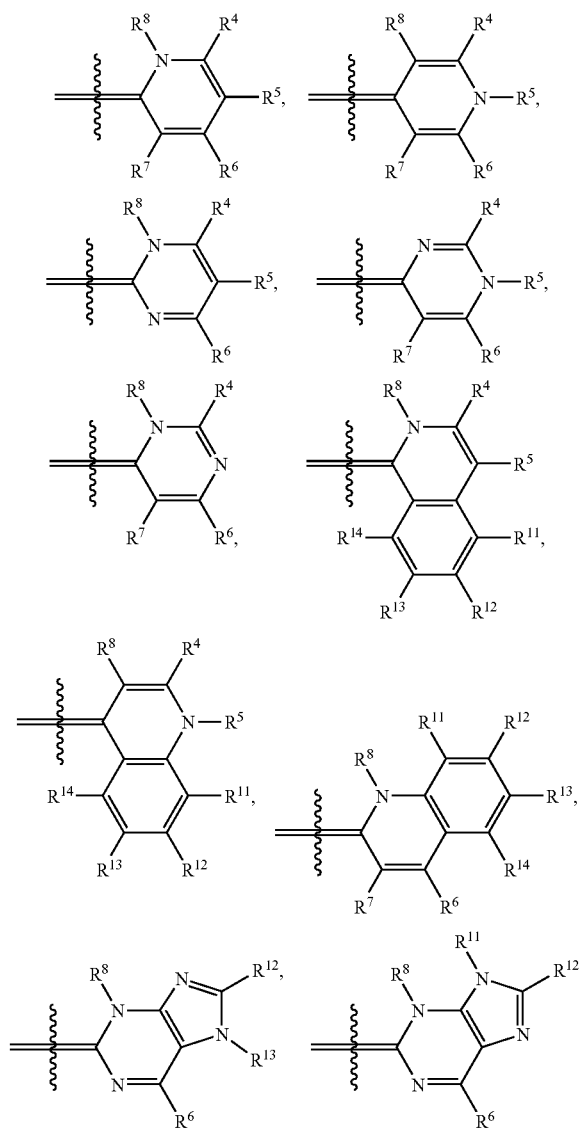

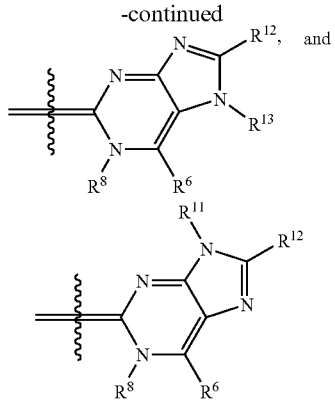

wherein $R^4$, $R^5$, $R^6$, $R^7$, $R^8$, $R^{11}$, $R^{12}$, $R^{13}$, and $R^{14}$ are in each occurrence in compounds of Formula III independently selected from the group consisting of hydrogen, halogen, alkyl, cycloalkyl, heteroalkyl, heterocycloalkyl, alkenyl, polyalkenyl, alkynyl, polyalkynyl, alkenylalkynyl, aryl, heteroaryl, and cycloalkyl, each of which may be optionally substituted.

Illustrative cyanine dyes useful in the present PCR reaction mixtures, methods, and compositions also include, but are not limited to, LightCycler Green, PO-PRO™-1, BO-PRO™-1, SYTO® 43, SYTO® 44, SYTO® 45, SYTOX® Blue, POPO™-1, POPO™-3, BOBO™-1, BOBO™-3, and other dyes having the general Formulae IV:

Formula IVa

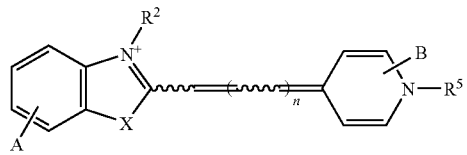

and

Formula IVb

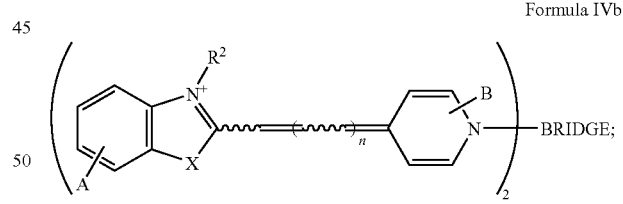

and the dyes G5, H5, D6, E6, P6, R6, Y6, Z6, and D8 presented in Example 14, and other dyes having the general Formulae V:

Formula Va

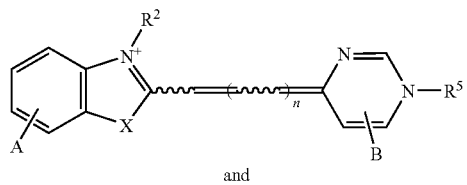

and

Formula Vb

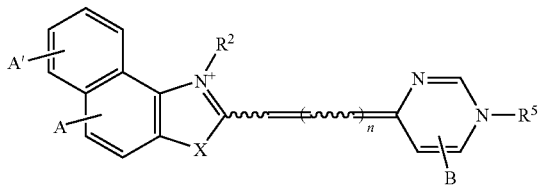

wherein ñ is 0, 1, or 2; $R^2$ is alkyl, hydroxyalkyl, alkoxyalkyl, aminoalkyl, mono and dialkylaminoalkyl, trialkylammoniumalkyl, alkylenecarboxylate, alkylenecarboxamide, alkylenesulfonate, and the like; $R^5$ is alkyl, hydroxyalkyl, alkoxyalkyl, aminoalkyl, mono or dialkylaminoalkyl, trialkylammoniumalkyl, alkylenecarboxylate, alkylenecarboxamide, alkylenesulfonate, optionally substituted phenyl, and the like; X is oxygen or sulfur; A, A', and B each represent one or more independently selected optional substituents, such as alkyl, halo, amino, haloalkyl, alkoxy, haloalkoxy, alkyl and arylsulfonyl, haloalkylsulfonyl, alkyl and arylthio, formyl, alkyl and arylcarbonyl, carboxyl derivatives, mono and dialkylamino, trialkylammonium, dialkylaminoalkyl, trialkylammoniumalkyl, or a heterocycle including pyrrolidino, piperidino, piperazino, each of which may be optionally substituted with alkyl, amino, mono or dialkylaminoalkyl, trialkylammoniumalkyl, or may be optionally quaternized on the nitrogen with an alkyl group, and the like; and BRIDGE is a divalent linker having the formula $(CH_2)_p N^+ Me_2 (CH_2)_q$, where p and q are independently 2 or 3, which includes the divalent linker $(CH_2)_3 N^+ Me_2 (CH_2)_3$. It is understood that when these dyes have a net charge, they are accompanied by one or more counter ions, such as counter anions including halide, alkanoate, phosphate, and the like, and counter cations including lithium, sodium, potassium, cesium, ammonium, and the like.

Other illustrative dyes for use herein include, but are not limited to YO-PRO®-1, TO-PRO®-1, SYTO® 11, SYTO® 13, SYTO® 15, SYTO® 16, SYTO® 20, SYTO® 23, TOTO™-3, YOYO®-3 (Molecular Probes, Inc.), GelStar® (Cambrex Bio Science Rockland Inc., Rockland, Me.), thiazole orange (Aldrich), and other dyes having the general Formulae VI:

Formula VIa

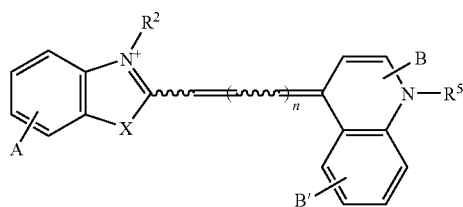

and

Formula VIb

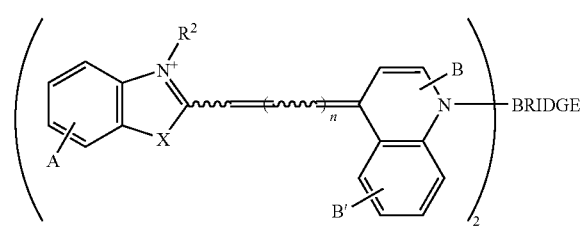

wherein n is 0, 1, or 2; $R^2$ is alkyl, hydroxyalkyl, alkoxyalkyl, aminoalkyl, mono and dialkylaminoalkyl, trialkylammoniumalkyl, alkylenecarboxylate, alkylenecarboxamide, alkylenesulfonate, and the like; $R^5$ is alkyl, hydroxyalkyl, alkoxyalkyl, aminoalkyl, mono or dialkylaminoalkyl, trialkylammoniumalkyl, alkylenecarboxylate, alkylenecarboxamide, alkylenesulfonate, optionally substituted phenyl, and the like; X is oxygen or sulfur; A, B, and B' each represent one or more independently selected optional substituents, such as alkyl, halo, amino, mono and dialkylamino, pyrrolidino, piperidino, piperazino, phenyl, hydroxy, alkoxy, thio, and alkylthio, each of which may be optionally substituted with alkyl, amino, mono or dialkylaminoalkyl, trialkylammoniumalkyl, and the like; and BRIDGE is a divalent linker having the formula $(CH_2)_p N^+ Me_2 (CH_2)_q$, where p and q are independently 2 or 3, which includes the divalent linker $(CH_2)_3 N^+ Me_2 (CH_2)_3$. It is understood that when these dyes have a net charge, they are accompanied by one or more counter ions, such as counter anions including halide, alkanoate, phosphate, and the like, and counter cations including lithium, sodium, potassium, cesium, ammonium, and the like.

Further, Table 1 (provided in Example 13 below) shows a comparison of several dsDNA dyes that are commonly used during or after PCR, as well as various dyes that have not previously been used for PCR analysis. Initial results have indicated that LC Green, PO-PRO™-1, JO-PRO™-1, BO-PRO™-1, G5, H5, D6, P6, Y6 and D8 are quite promising dyes for heteroduplex detection. There are several surprising characteristics of these dyes. First, they do not significantly inhibit PCR at 50% saturation. In fact, saturation levels fairly close to 100% are compatible with PCR with three of these dyes. Secondly, although some of the dyes emit in the blue range, they are compatible with use in the fluorescein channel of a variety of currently available instruments. Adjustment of the optics to better match the excitation/emission spectra of these dyes may further improve their sensitivity for use in quantitative or qualitative amplification analysis.

It is understood that the above cyanine dyes are illustrative, and other cyanine dyes may be useful in the presently-described methods.

Some quinolinium-based unsymmetrical cyanines such as, but not limited to, SYBR® Green I, SYTOX® Green, SYTO® 14, SYTO® 21, SYTO® 24, SYT® 25, TOTO™-1 and YOYO®-1 have not proven useful for heteroduplex detection or for the detection of multiple products in a closed-tube system. When the dye is a monomer of a quinolinium-based cyanine, it is possible that bulky substitutions on the carbon next to the nitrogen of the quinolonium ring (position equivalent to $R^4$) interfere with the dye's ability to function in the methods of the present invention. Bulky substitutions are, for example, long-chain branched hetero-atom-containing aliphatic or aromatic moieties substituted with branched-chain aliphatic moieties that are larger than MW of about 105. This restriction, however, does not apply to any of the pyridinium or pyrimidinium cyanines mentioned earlier. In the case of quinolinium-based cyanine dimers, the distance between the left and right ring systems, as defined by the divalent fragment:

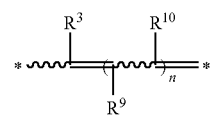

also appears to determine functionality. Functionality may be determined by heteroduplex detection, as taught herein in Examples 13-14. Other dyes previously described as useful in real-time monitoring of PCR, such as SYBR® Gold, Pico Green, and ethidium bromide have also been shown to be ineffective in heteroduplex detection in a closed-tube PCR system.

The dyes for use in the present invention may be used in a dye-based method for SNP genotyping, requiring only two unlabeled oligonucleotide primers and one well for each SNP genotype, and not requiring real-time PCR. A dsDNA dye is used such that heterozygotes are identified by the presence of heteroduplexes that alter the shape of the post-amplification melting curve. Different homozygous genotypes are differentiated by their Tm difference, or alternately by mixing a known homozygous DNA sample with the unknown and looking for heteroduplexes. Illustratively, PCR primer design is greatly simplified because very short amplicons can be used, preferably immediately flanking the SNP. Such short amplicons also amplify very efficiently, reduce the risk of amplifying alternate targets, and allow very rapid thermal cycling.

The design of PCR primers is not an exact science, and often trial and error is necessary. Although some rules for PCR primer design are generally accepted, the validity of these rules has not been tested. Because the effect of different genotypes on melting curves is greater with short amplicons, short amplicons are preferred ($\leq 100$ bp), and the shortest possible amplicons are often best ($\leq 50$ bp). Therefore, to design primers for genotyping with dsDNA dyes, one illustratively starts with each flanking primer right next to the SNP position. That is, the amplicon length will be the length of primer 1, plus the length of primer 2, plus the length of the region that needs to be tested (the length of an SNP is 1). For efficient amplification, the melting temperature (Tm) of the two primers should be nearly the same. Convenient Tms for primers may be 50 to 70 degrees C. Primers with the highest Tm illustratively will allow the fastest thermal cycling, while primers with lower Tm are generally less expensive and produce the shortest amplicons, resulting in greater genotyping differences. Primer lengths between 12 and 30 bases are usually used. Illustratively, each primer is built away from the SNP until the calculated Tm is closest to the desired Tm. Methods for Tm calculation are well known in the art (e.g., Clin. Chem. 2001;47:1956-61). In general, the primer lengths will not be the same when the Tms are matched as closely as possible. For example, the primer lengths used in the Factor V SNP assay (FIG. 1) are 17 and 24 bases long both with a calculated matched Tm near 62° C.

Thermal cycling parameters for amplification can be very short because little primer extension is required for such short amplicons. After an initial denaturation of genomic DNA before thermal cycling, denaturation and annealing temperatures do not need to be held, and the extension time can be 10 s or less. It is even possible to reduce the programmed extension time to zero, allowing each cycle to be performed in less than 20 s. Alternately, an extension time of 1 s can be used. Because the amplicon is so short, large amounts of polymerase are not required (<0.6 ts per 10 μl may be used).

Thus, the following illustrative steps may be followed for SNP genotyping according to the present invention:

1. Choose a target Tm and start with the 3'-end of each primer right next to the SNP position. Optionally, one primer may be shifted slightly away from the SNP position to avoid 3' complementarity between primers to decrease the risk of primer dimer formation.

2. Design each primer outward until the calculated Tm is as close as possible to the target Tm.

3. Rapidly thermal cycle the sample in the presence of PCR reagents and a dsDNA dye that allows heteroduplex detection.

4. Form heteroduplexes by rapid cooling at a rate of at least −0.1° C./s, preferably at least −2° C./s, and most preferably at least −5° C./s after denaturation.

5. Heat at 0.1 to 0.5° C./s and acquire a melting curve.

6. If the amplification fails, move the 3'-end of one of the primers out 1 base and repeat all steps until successful.

Figure 4:
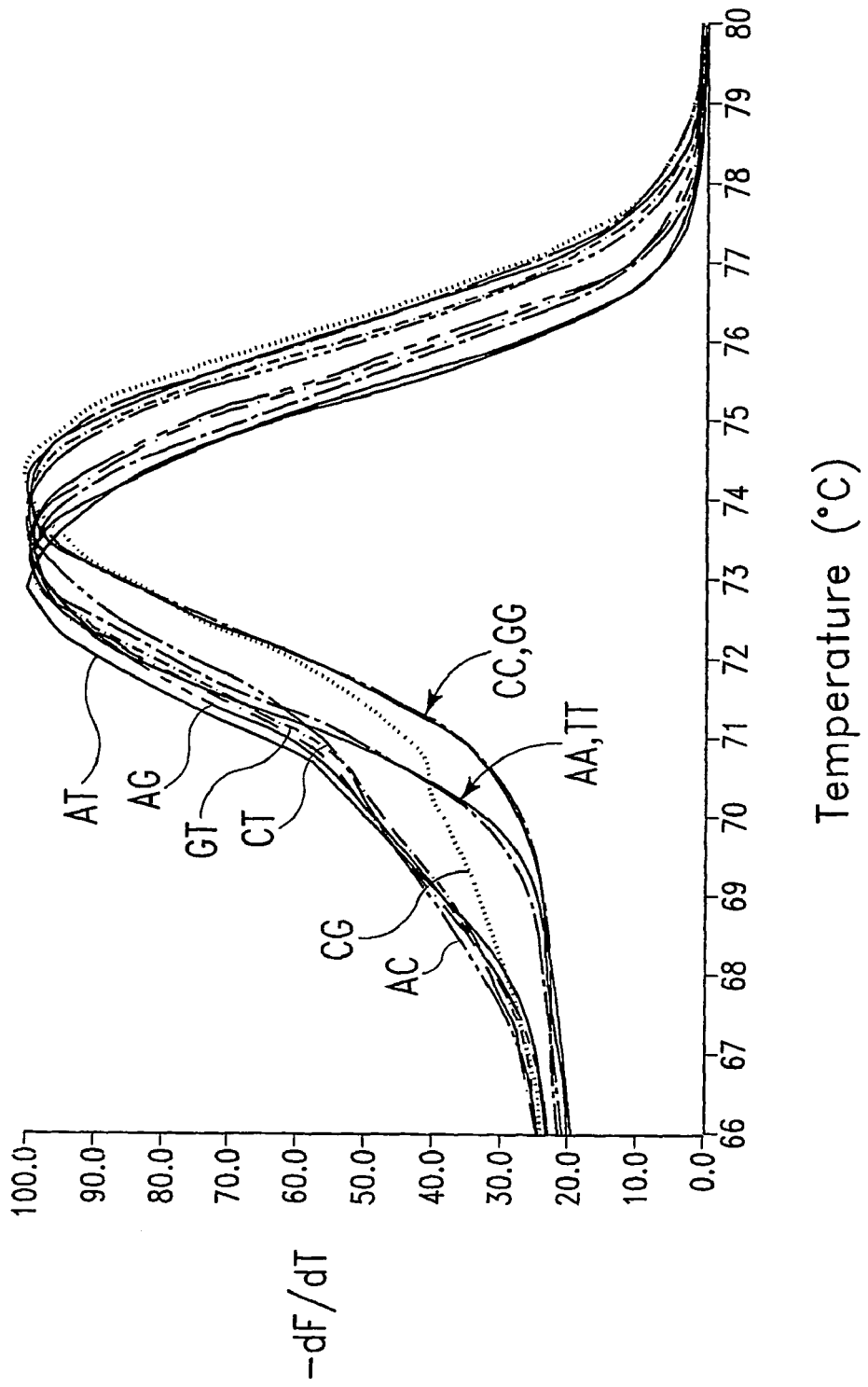
FIG. 4 shows a model system for detecting six combinations of heteroduplexes.

In an illustrated example, all heterozygotes can be detected by the effect of the heteroduplexes on the melting curve (FIG. 4). In addition, 4 out of 6 homozygous differences (A vs C, A vs G, C vs T, and G vs T) are very easily distinguished by Tm shifts (FIG. 4, arrows). However, to distinguish A vs T homozygotes, high resolution melting may be necessary, and in some cases, C vs G homozygotes cannot be differentiated even with high resolution melting. In the cases where differentiation of homozygotes is difficult, a sample of a known homozygous genotype may be mixed in roughly equal amounts with the unknown genotype either before or after amplification. The mixture is amplified (if not previously amplified), denatured, and melted. If the genotypes are the same, the melting curve of the mixture will be the same as the melting curve of the known homozygous genotype. If the genotypes are different, heteroduplexes will be produced and identified by an altered shape of the melting curve. Illustratively, small amplicons may be used when genotyping for known sequence variants. Large amplicons may be preferred when scanning for unknown variants.

Unsymmetrical cyanine dyes can be prepared by a general method that attaches the benzazolium portion of the molecule to the pyridinium (or quinolinium, pyrimidinium, purinium) portion through one or more "—C(R)=" groups. As described in U.S. Pat. No. 5,436,134 and references cited therein, the number of "—CR)=" groups is determined by the specific synthetic reagents used in the synthesis. In the synthesis of monomethine dyes (R=H, n=0) such as LC Green, a combination of reagents is used in which the methine carbon atom results from either A on the benzazolium salt or B on the pyridinium salt being methyl and the other of A or B being a reactive leaving group that is typically methylthio, methylsulfonyl, or chloro, but which can be any leaving group that provides sufficient reactivity to complete the reaction. One possible way to prepare LC Green and other similar dyes is as follows:

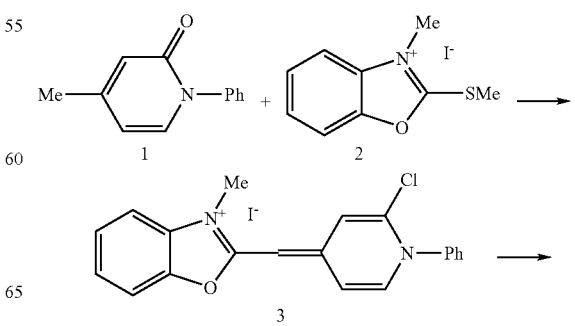

-continued

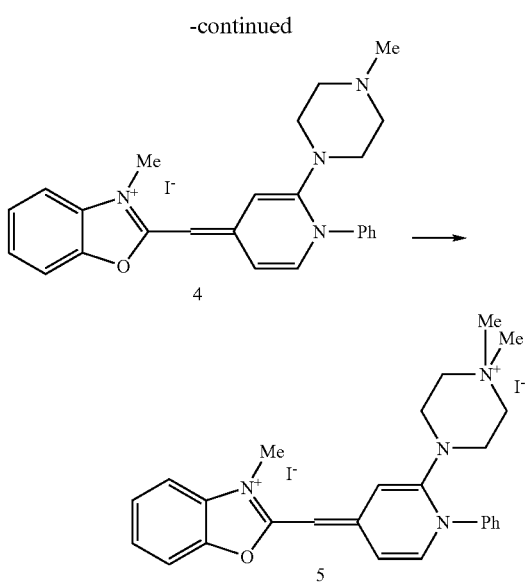

The starting material, Compound 1 is prepared by heating 4-methyl-2-pyridinone (Aldrich) to reflux with copper powder, potassium carbonate and iodobenzene for 48 hours. The reaction is cooled to room temperature, partitioned between water and ethyl acetate, filtered, and the organic layer is dried over magnesium sulfate. The crude product is purified on a silica gel column, eluting with 1:1 ethyl acetate/hexanes to yield Compound 1.

Another starting material, Compound 2, is prepared by adding 2-(methylthio)benzoxazole to methyl iodide in DMF and heating in a sealed tube at 150° C. for one hour to obtain Compound 2, as the iodide salt.

A mixture of Compound 1, phosphorous oxychloride, and a catalytic amount of DMF in methylene chloride is heated to reflux for 24 hours. The mixture is cooled to room temperature and another volume of methylene chloride is added, followed by Compound 2 and one equivalent of triethylamine. The mixture is stirred at room temperature for 6 hours. A solid is separated by filtration and purified using a silica gel column eluting with a mixture of ethyl acetate/chloroform/methanol. The purified compound is then redissolved in methanol and added to an excess of sodium iodide in water. Compound 3 is isolated by filtration as the iodide salt and dried in vacuo.

Compound 3 is then mixed with 1-methylpiperazine in 1,2-dichloroethane and heated at 55° C. for 2 hours. The resulting product (Compound 4) is then quaternized by adding an excess of methyl iodide and Proton Sponge (Aldrich), and is expected to yield LightCycler Green (Compound 5) as the diiodide salt.

EXAMPLE 1

PCR Protocol

Labeled and unlabeled oligonucleotides were obtained from IT Biochem (Salt Lake City, Utah), Qiagen Operon (Alameda, Calif.), or Synthegen (Houston, Tex.). PCR was performed in 10 μl volumes in a LightCycler® (Roche Applied Systems, Indianapolis, Ind.) with programmed transitions of 20° C./s unless otherwise indicated. The amplification mixture included 50 ng of genomic DNA as template, 200 μM of each dNTP, 3 mM $MgCl_2$, 100 mM 2-amino-2-methyl-1,3-propanediol, pH 8.8, 0.04 U/μl Taq polymerase (Roche), 500 μg/ml bovine serum albumin, and 0.5 μM of each primer unless indicated otherwise. Genotyped human genomic DNA was obtained from prior studies (Gundry C N, et al., Genetic Testing, 1999;3:365-70; Herrmann M, et al., Clin Chem 2000;46:425-8) or from Coriell Cell Repositories (Camden, N.J.). LightCycler Green was included in the PCR reaction at 10 μM unless otherwise indicated. When SYBR® Green I was used as the indicator, a 1:10,000 final dilution from the Molecular Probes stock was used. The dye is added before PCR, amplification performed, and the melting transition of the amplicon is monitored on the LightCycler® or by high resolution melting analysis. Different homozygotes are distinguished by amplicon melting temperature (Tm). Heterozygotes are identified by low temperature melting of heteroduplexes that broaden the overall melting transition. Melting analysis requires about 1 min and no sample processing is needed after PCR.

To study the sensitivity of LC Green, SYBR® Green I, and other dsDNA binding dyes, polymorphisms in Factor V Leiden, cystic fibrosis (F508del, F508C, I507del, I506V), and HTR2A (T102C) genes were analyzed. In addition, engineered plasmids were used to systematically study all possible single base changes. Heteroduplexes produced by amplification of heterozygous DNA were best detected by rapid cooling (at least −2° C./s) of denatured products, followed by rapid heating during melting analysis (0.2 to 0.4° C./s). All heterozygotes were distinguished from homozygotes by a broader melting transition. Different homozygotes could often be distinguished by their Tm. Homozygotes with an A to T base change could only be distinguished by high resolution melting analysis or by mixing homozygotes. Homozygous G to C base changes could not reproducibly be distinguished, even with high resolution analysis, without mixing homozygotes. The amplicons varied in length from 44 to 331 bp.

While LC Green is used in the Examples provided herein, it is understood that other dyes according to this invention may be used.

EXAMPLE 2

Melting Curve Analysis

Melting analysis was performed either on the LightCycler® immediately after cycling, or subsequently on a high-resolution melting instrument (HR-1, Idaho Technology, Salt Lake City, Utah). However, it is understood that melting curve analysis may be performed in the absence of amplification. When the LightCycler® was used, the samples were first heated to 94° C., cooled to 60° C. at a program setting of −20° C./s, then melted at 0.2° C./s with continuous acquisition of fluorescence. For high-resolution melting, the samples were first amplified in the LightCycler®, then heated momentarily in the LightCycler® to 94° C. and rapidly cooled (program setting of −20° C./s) to 40° C. unless stated otherwise. The LightCycler® capillaries were then transferred one at a time to the high-resolution instrument and heated at 0.3° C./s unless otherwise stated. The HR-1 is a single sample instrument that surrounds one LightCycler® capillary with an aluminum cylinder. The system is heated by Joule heating through a coil wound around the outside of the cylinder. Sample temperature is monitored with a thermocouple also placed within the cylinder and converted to a 16-bit digital signal. Fluorescence is monitored by epi-illumination of the capillary tip (Wittwer C T, et al., BioTechniques 1997;22:

176-81) that is positioned at the bottom of the cylinder and also converted to a 16-bit signal. Approximately 50 data points are acquired for every ° C.

In some cases it is advantageous not to denature the product after PCR before melting curve acquisition. For example, when the goal is to type the number of repeat sequences (e.g., STRs, VNIRs), amplification may be stopped at the extension step during the exponential phase of the reaction before plateau, and then melting analysis is performed. This way, homoduplex extension products can be analyzed. In repeat typing, homoduplex products can be more informative than heteroduplex products, especially since many different heteroduplex products may form from different alignment of the repeats. In some cases, it may be helpful to obtain both a homoduplex melting curve (without prior denaturation) and a heteroduplex melting curve (with denaturation and the formation of all possible duplex combinations). The difference between these two melting curves gives a measure of the extent of heteroduplexes that can be formed, using the same sample as the "homoduplex control".

LightCycler® and high-resolution melting data were analyzed with custom software written in LabView. Fluorescence vs temperature plots were normalized between 0 and 100 percent by first defining linear baselines before and after the melting transition of each sample. Within each sample, the fluorescence of each acquisition was calculated as the percent fluorescence between the top and bottom baselines at the acquisition temperature. In some cases, derivative melting curve plots were calculated from the Savitsky-Golay polynomials at each point (Press W H, et al., eds. Numerical recipes in C, $2^{nd}$ ed. New York: Cambridge University Press, 1992: 650-5). Savitsky-Golay analysis used a second-degree polynomial and a data window including all points within a 1° C. interval. Peak areas and melting temperatures were obtained by using non-linear least squares regression to fit multiple Gaussians. In some cases, the X-axis for each normalized melting curve was translated so that the tracings overlapped within a certain fluorescence range. This "temperature shifting" corrects for any minor inter-run temperature variation and increases the ability to distinguish heterozygotes from homozygotes. The difference between genotypes can also be magnified by plotting the fluorescence difference between genotypes at each temperature.

EXAMPLE 3

Single Nucleotide Polymorphism Genotyping with LightCycler Green: Genotyping the Factor V Leiden Mutation A 43 bp amplicon was formed from primers 18 and 24 bases in length, immediately flanking the location of the factor V Leiden mutation. Both primers had an estimated Tm of 62° C. The samples were cycled 35 times with the following protocol: 94° C. with no hold, 60° C. with no hold, and 72° C. with a 10 s hold. After amplification, the samples were heated momentarily in the LightCycler® to 94° C., cooled rapidly (program setting of −20° C./s) to 60° C., and PCR products melted at 0.2° C./s with continuous fluorescence acquisition.

Figure 1:
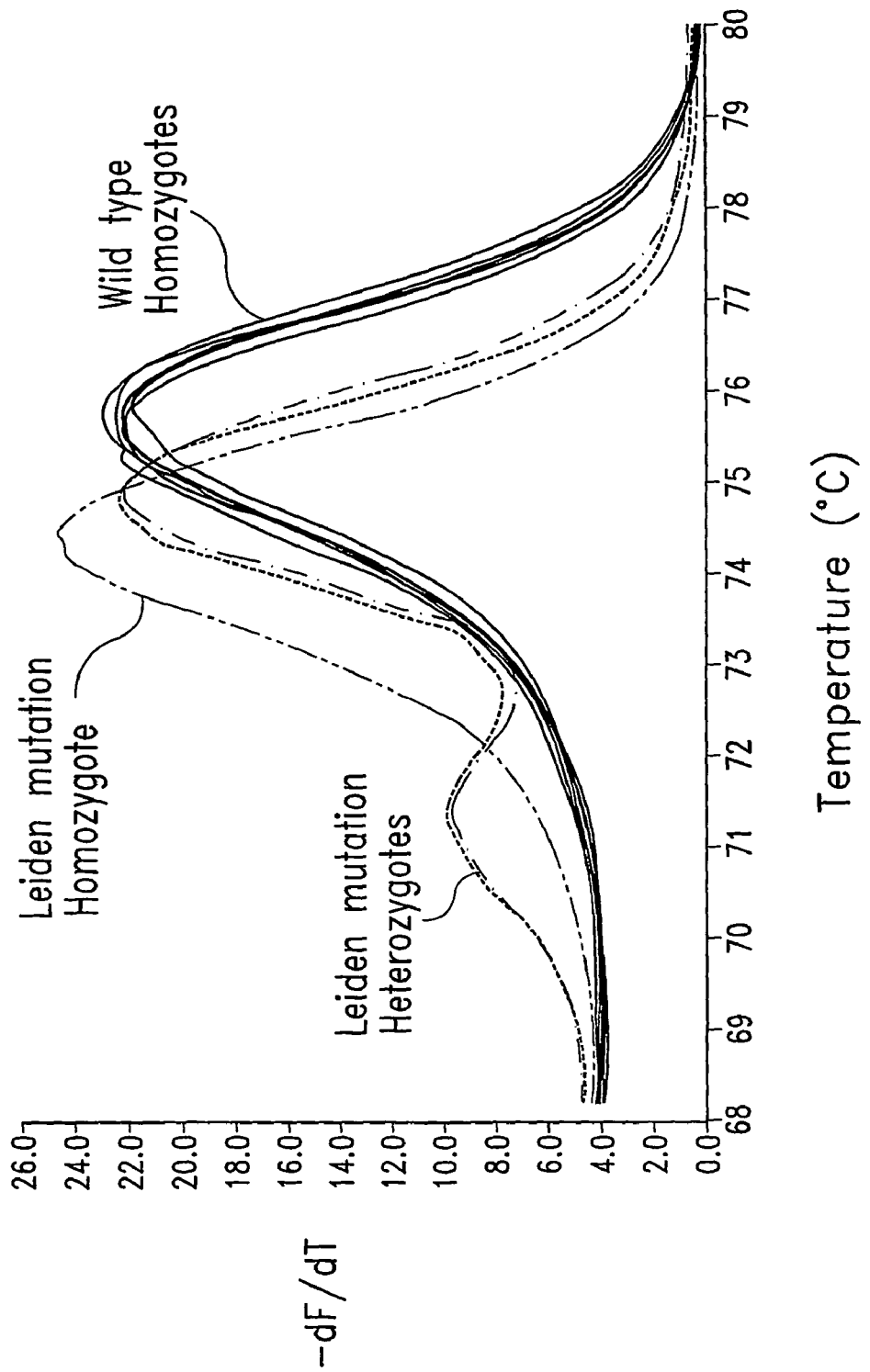
FIG. 1 shows genotyping of the Factor V Leiden using LightCycler Green. The negative first derivative (-dF/dT) of the melting curve is shown.

Derivative melting curves of PCR products amplified from different senotypes at the Leiden locus of the factor V gene are shown in FIG. 1. LightCycler Green was used for fluorescent monitoring of the melting transition between double- and single-stranded products. The Leiden mutation is located 19 bases from one end of the amplicon. Results from ten homozygous wild type, two heterozygous, and one homozygous Leiden genotypes are shown. The amplicon melting temperature of the homozygous mutant is about 1° C. less than the homozygous wild type melting temperature. Heterozygous samples show a secondary, low temperature melting transition attributable to heteroduplex formation. A similar experiment using SYBR® Green I failed to detect this secondary melting transition in heterozygotes (data not shown).

The effects of cooling rate and heating rate were studied using heterozygous factor V Leiden DNA on the LightCycler®. To study the effect of cooling rate, the samples were amplified as above, heated to 85° C., and then cooled from 85° C. to 60° C. at rate of −20, −2, −1, −0.5, or −0.1° C./s, followed by a constant heating rate of 0.2° C./s for melting curve acquisition. Rapid cooling was necessary for significant heteroduplex formation (FIG. 2). Heteroduplexes were not observed when the cooling rate was −0.1° C./s or slower. The greatest heteroduplex formation occurred when capillary samples were rapidly transferred from boiling water to ice water (data not shown). With cooling on the LightCycler®, heteroduplex formation appeared to plateau at programmed rates faster than −5° C./s (FIG. 2). However, measurement of actual sample temperatures showed that the cooling rate increased slightly with programmed rates faster than −5° C./s: when the instrument was programmed to cool at −20° C./s, the actual rate was about −6° C./s.

Figure 3:
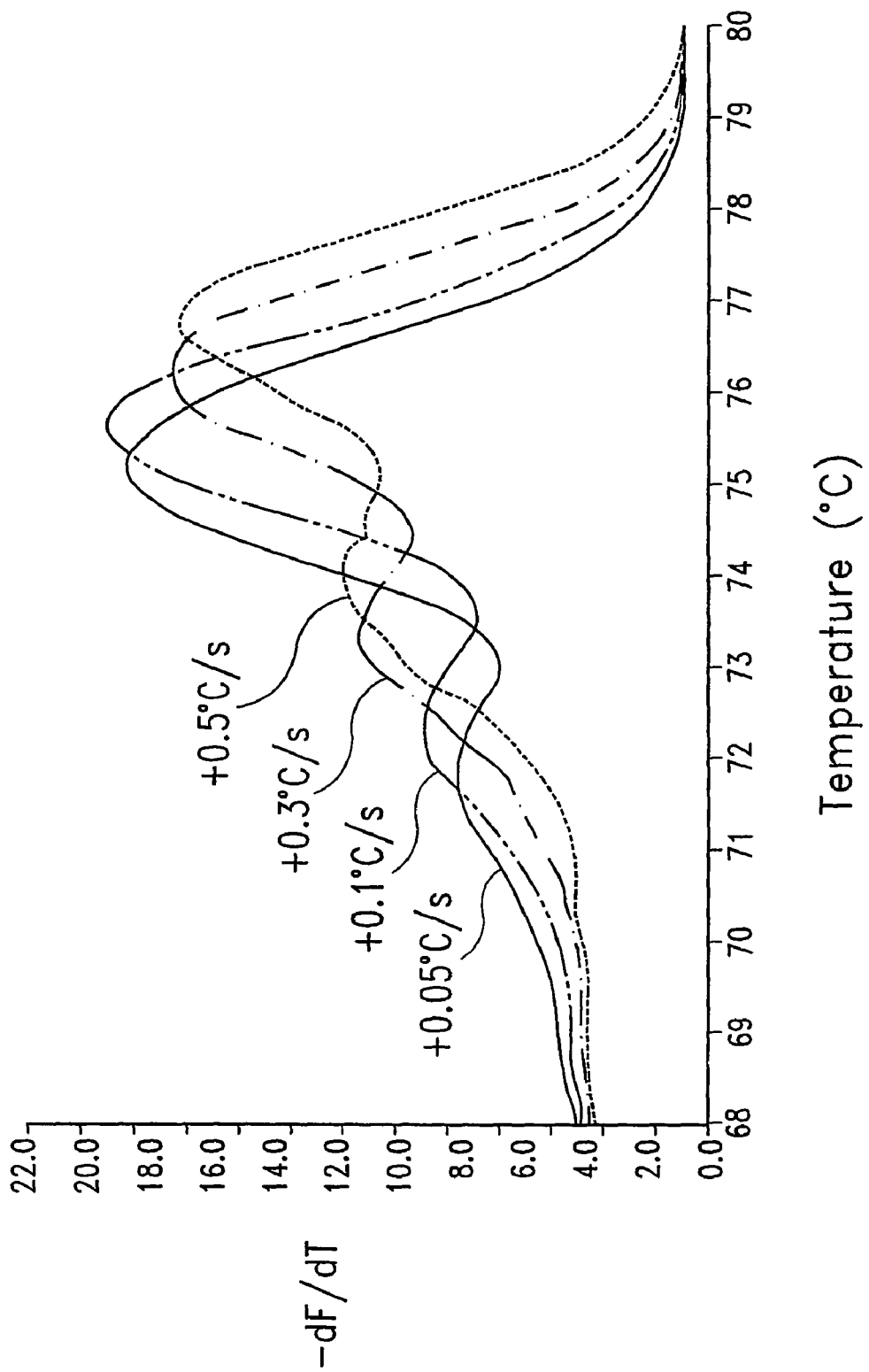
FIG. 3 shows the effect of heating rates during melting analysis on the detection of heteroduplexes.

The effect of heating rate was studied by cooling at a programmed rate of −20° C./s, followed by melting at 0.05, 0.1, 0.3, or 0.5° C./s. The relative percentage observed heteroduplexes was greater with higher heating rates (FIG. 3). The apparent Tm also shifts to higher temperatures as the rate increases and the melting process deviates more from equilibrium (Gundry C N, et al., Genetic Testing, 1999;3:365-70).

EXAMPLE 4

Systematic Study of SNP Genotyping with Plasmids

Engineered plasmids were used for systematic study of melting curve genotyping of all possible single base changes. The plasmids (DNA Toolbox, Cambrex Bio Science Rockland Inc.) contained either A, C, G, or T at a defined position amid 40% GC content (Highsmith W E, et al., Electrophoresis 1999;20:1186-94). Primers with a Tm of 62±1° C. were immediately adjacent to the polymorphic position. The DNA templates were used at $10^5$ copies and PCR was performed with 35 cycles of 94° C. with no hold, 60° C. with no hold, and 75° C. for 5 s. The LightCycler® was used for melting analysis.

FIG. 4 demonstrates that all possible heteroduplexes formed from single base polymorphisms can be distinguished from the homoduplex samples. In each case, the presence of heteroduplexes results in a low temperature shoulder on derivative melting curve plots. When the sample includes only homoduplexes formed from the amplification of homozygotes, no low temperature shoulders are present. Furthermore, AA or TT homozygotes are clearly distinguished from CC or GG homozygotes by their melting temperature. It is not clear from these "low-resolution" plots (obtained on the LightCycler®) whether all heterozygotes can be distinguished from each other, or whether AA can be differentiated from TT, and CC can be differentiated from GG. However, high-resolution data (not shown) demonstrates that AA can be distinguished from TT, and most (if not all) heterozygotes can be distinguished. The stability of CC and GG homozygotes appears to be very similar and any difference is difficult to resolve on current instrumentation, without mixing homozygotes.

EXAMPLE 5

Genotyping of the Cystic Fibrosis Gene With Labeled Primers: LightCycler Green or SYBR® Green I KlenTaq1 polymerase (0.04 U/µl, AB Peptides, St. Louis, Mo.), 88 ng of TaqStart antibody (ClonTech, Palo Alto, Calif.), and 50 mM Tris, pH 8.3 were used in PCR instead of Taq polymerase and 2-amino-2-methyl-1,3-propanediol. A 44 bp fragment was amplified with the primers GGCACCAT-TAAAGAAAATAT (SEQ ID NO 1) and TCATCATAG-GAAACACCA (SEQ ID NO 2). The first primer was either 5'-labeled with Oregon Green, or the reaction was performed in the presence of SYBR® Green I or LightCycler Green. The primers flank the mutational hot spot containing the F508del, I507del, and F508C variants. PCR was performed through 40 cycles of 85° C. and 58° C. (0 s holds). Six samples were monitored during melting curve acquisition on the LightCycler®.

Figure 5B:
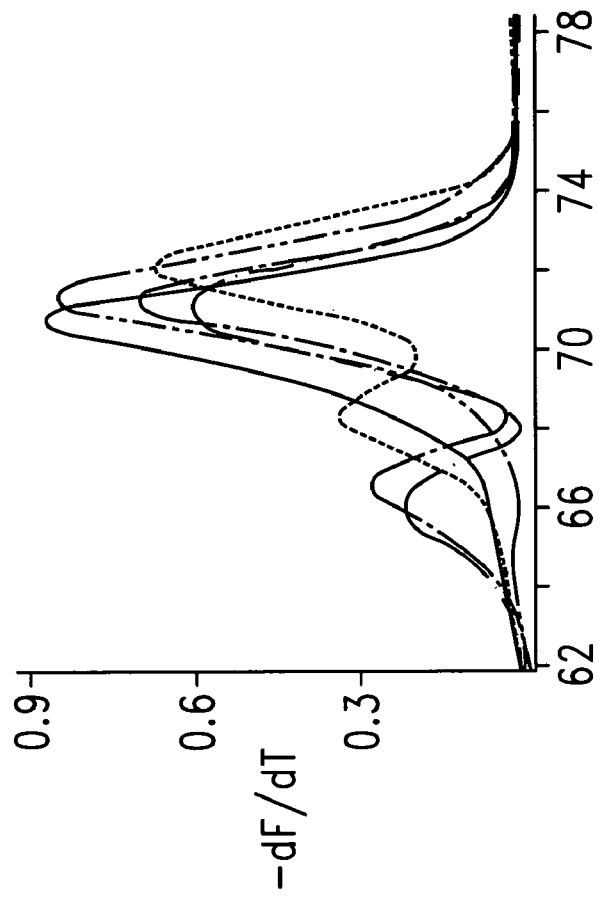
Figure 5A:
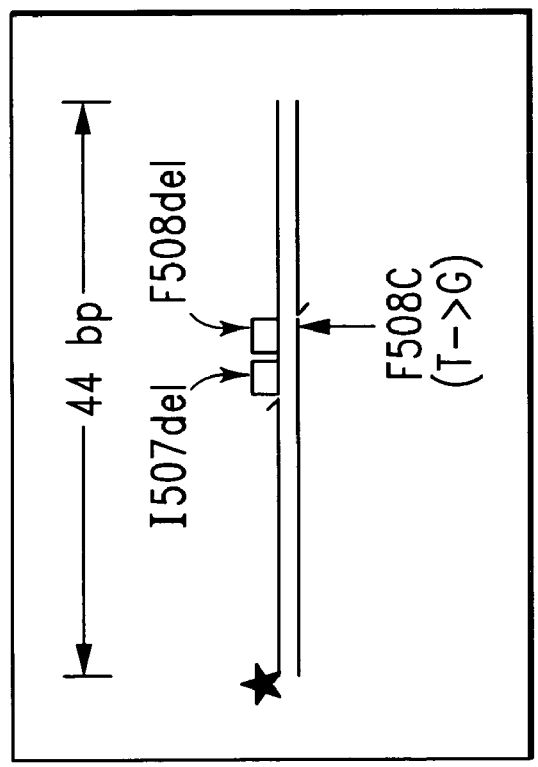

Derivative melting curves of PCR products amplified from different genotypes at the I507/F508 region of the cystic fibrosis gene are shown in FIGS. 5B-D. The PCR products were 41 or 44 bases long (FIG. 5A). Either a 5'-labeled primer (FIG. 5B), LightCycler Green (FIG. 5C), or SYBR® Green I (FIG. 5D) was used for fluorescent monitoring of the melting transition between double and single stranded products. Results from two homozygous and three heterozygous genotypes are shown.

The duplex stability of the different genotypes follows theoretical calculations (von Ahsen N, et al., Clin Chem 2001; 47:1956-61), with F508del~I507del<Wild type<F508C. Except for F508del and I507del, the genotypes are distinguishable by the Tms of their major transitions. The standard deviation of the Tm of 10 replicate wild type samples was 0.12° C. when melted on the LightCycler®. When melted on the high-resolution instrument, the standard deviation of the Tm of the same 10 samples was 0.04° C.

When a heterozygous sample is amplified by PCR, two homoduplex and two heteroduplex products are expected (Nataraj A J, et al., Electrophoresis 1999;20: 1177-85). However, when SYBR® Green I was used as the fluorescent indicator, only a single melting peak was apparent for each genotype (FIG. 5D). In contrast, when labeled primers or LightCycler Green are used under the same conditions, two clearly defined peaks appeared (FIGS. 5B and 5C). The lower temperature peak is always smaller than the higher temperature peak, and presumably indicates the melting transition of one or both heteroduplex products. As might be expected, the heterozygotes with 3 bp deleted (F508del and I507del) resulted in heteroduplex peaks that were more destabilized than heteroduplex peaks from a single base change (F508C). The primary peak from the F508C heterozygote was at a higher temperature than wild type, reflecting the greater stability of the T to G transversion (Gundry C N, et al., Genetic Testing, 1999;3:365-70).

EXAMPLE 6

Mutation Scanning With LC Green

The HTR2A single nucleotide polymorphism was studied. The PCR was performed with KlenTaq, TaqStart, and Tris as described for the cystic fibrosis locus. A 331 bp fragment of the hydroxytryptamine receptor 2A (HTR2A) gene included the common polymorphism (T102C) within exon 1 (Lipsky R H, et al., Clin Chem 2001;47:635-44). The reaction was cycled 40 times between 95° C. with no hold, 62° C. with a 2 s hold, and 74° C. with a 20 s hold. A high-resolution melting curve was obtained.

Figure 6:
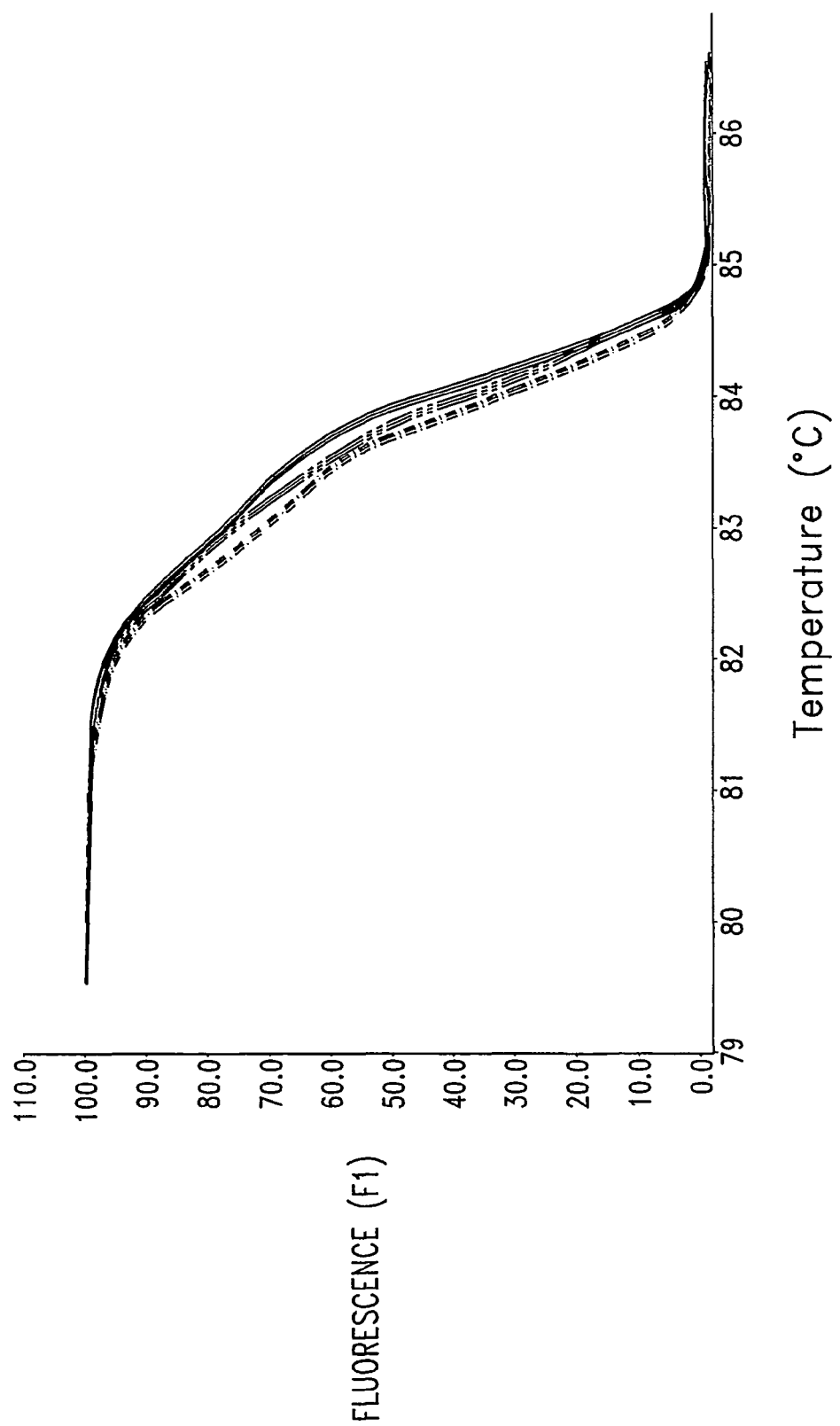
FIG. 6 shows genotyping using LightCycler Green on longer amplicons (--- homozygote (TT), — homozygote (CC), --- heterozygote (TC). The melting curves for three individuals (not the derivatives) are shown.

FIG. 6 demonstrates that LightCycler Green can be used to scan for sequence variants. That is, the location of the sequence variant need not be known. The presence of any variant can be detected within a large amplicon. As seen in FIG. 6, all three genotypes of the single nucleotide polymorphism in the HTR2A gene (homozygous T, homozygous C and heterozygous T/C) can be differentiated within a 331 bp amplicon. Melting curve precision and the ability to distinguish different genotypes depends on the temperature and fluorescence resolution of the instrument.

EXAMPLE 7

Melting Curve Analysis of a DNA Size Ladder: Comparison of SYBR® Green I to LightCycler Green One hundred ng of a DNA size ladder (Low Mass DNA Ladder, Gibco BRL) having six distinct dsDNA species was mixed with either SYBR® Green I (1:10,000) or LightCycler Green (10 µM) in 3 mM MgCl$_2$, 100 mM 2-amino-2-methyl-1,3-propanediol, pH 8.7 buffer. A melting curve was obtained on the high-resolution instrument at 0.1° C./s.

As discussed above, LightCycler Green, unlike SYBR® Green I, can identify heteroduplexes in melting curve transitions at concentrations compatible with PCR. One reason why SYBR® Green I cannot easily identify low melting transitions is illustrated in FIG. 7. When several DNA fragments of increasing stability are present, the low temperature peaks are very small with SYBR® Green I as compared to LightCycler Green. One explanation is that during melting, SYBR® E Green I may be released from low temperature duplexes, only to attach to duplexes that melt at higher temperatures. This causes each successive peak to be higher than the last, with the lowest temperature peaks being very small, if observable at all. LightCycler Green, which is present at a much higher saturation level, has visible peaks for even low temperature duplexes. While LC Green was present at near saturation levels in this example, surprisingly, LC Green can detect the low temperature peaks when diluted to saturation levels of 5-20%. For example, the data illustrated in FIG. 13 were obtained using an LC Green concentration of 1 µM. Thus, while the mechanism is not understood, LC Green and various other saturating dyes of this invention do not appear to redistribute during melting.

Figure 8:
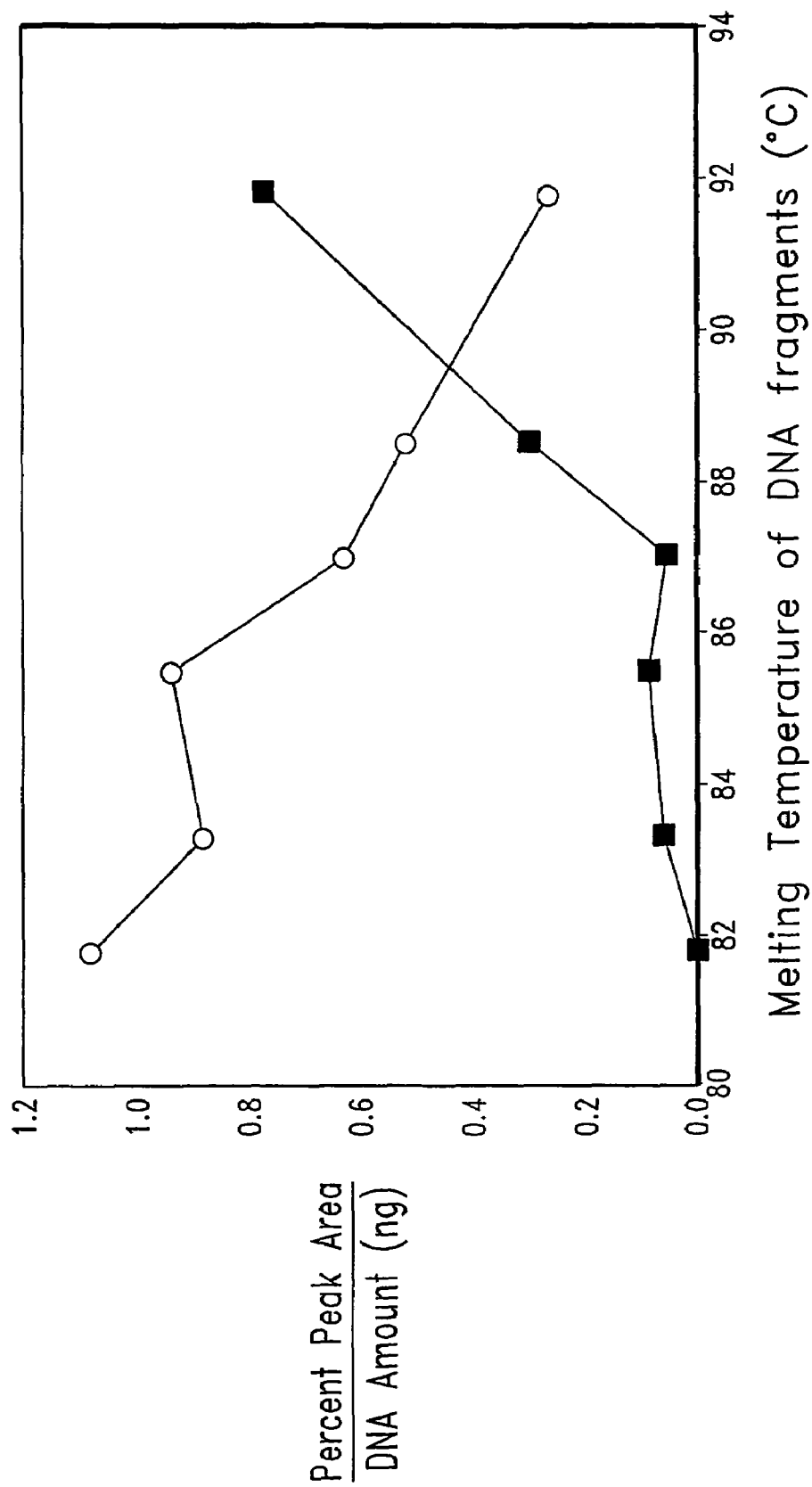
FIG. 8 demonstrates the non-linearity of fluorescence change when multiple DNA species are present. LightCycler Green (open circles) and SYBR® Green I (closed squares) are shown.

If the areas of each peak in FIG. 7 are determined and divided by the known amount of each of the DNA species, the relative sensitivity for each DNA species can be assessed (FIG. 8). As shown in FIG. 8, with LightCycler Green, low temperature melting peaks are favored, whereas with SYBR® Green I, a large enhancement of signal is observed at high temperature.

EXAMPLE 8

Titration Curves of Common dsDNA Dyes And Determination of Useful Concentration Range of LightCycler Green in PCR One hundred ng of the low mass DNA ladder was mixed with different concentrations of common dsDNA dyes in the presence of 3 mM $MgCl_2$, 50 mM Tris, pH 8.3, 250 µg/ml BSA and 200 µM each DNTP in a final volume of 10 µl. The samples were transferred to LightCycler® tubes and the fluorescence measured at 40° C. on the real-time fluorimeter. The fluorescence was normalized to the maximum fluorescence obtained with each particular dye.

Dilution studies were done using a 152 bp HTR2A amplicon in 10 µl volumes with 3 mM $Mg^{2+}$, 50 mM Tris-HCl, pH=8.3, 500 µg/ml BSA, 200 µM each dNTP, 0.5 µM of each primer, 50 ng genomic DNA, 0.4 U of Taq Polymerase, and 88 ng of TaqStart antibody, with LC Green dilutions ranging from 2 µM to 100 µM. After an initial denaturation for 10 s at 95° C., 40 cycles of 95 ° C. for 0 sec, 62° C. for 2 sec, and 72° C. for 20 sec were performed. After additional temperature conditioning on the LightCycler® (95 ° C. for 0 s, 55° C. for 0 s) the samples were melted on the high-resolution instrument with a slope of 0.3° C./sec.

Figure 9A:
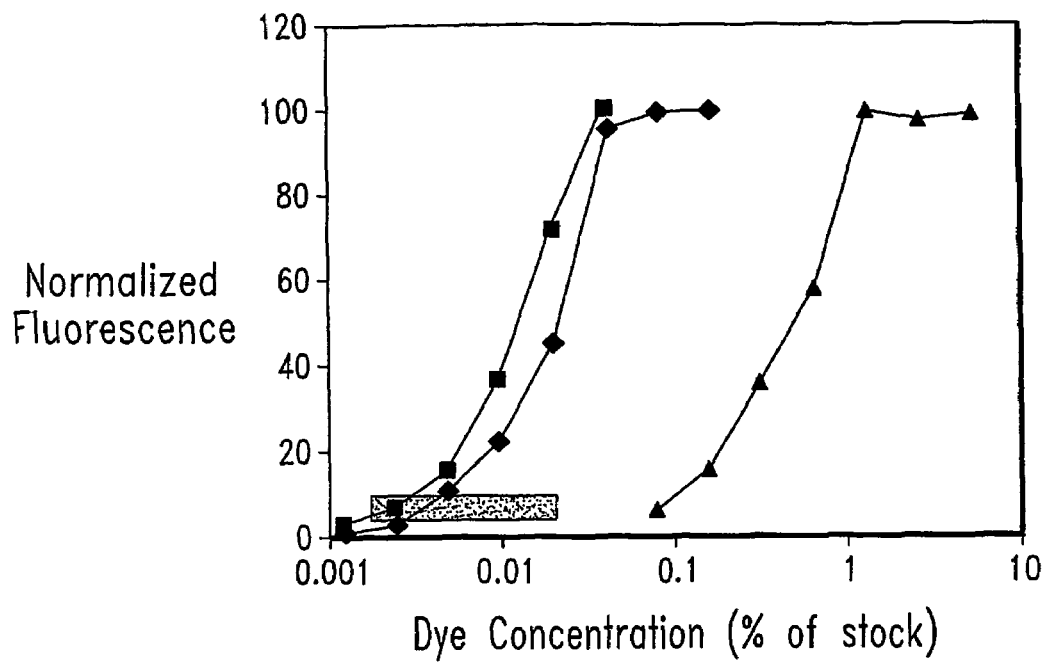
FIGS. 9A-B show dye titrations to determine saturation percentages, in FIG. 9A, ♦— SYBR® Green, ■— SYBR® Gold, ▲— Pico Green, in FIG. 9B, ○ LightCycler Green, ■ SYTX® Green. Illustrative PCR ranges for SYBR® Green I and LightCycler Green are indicated by the shaded box.
Figure 9B:
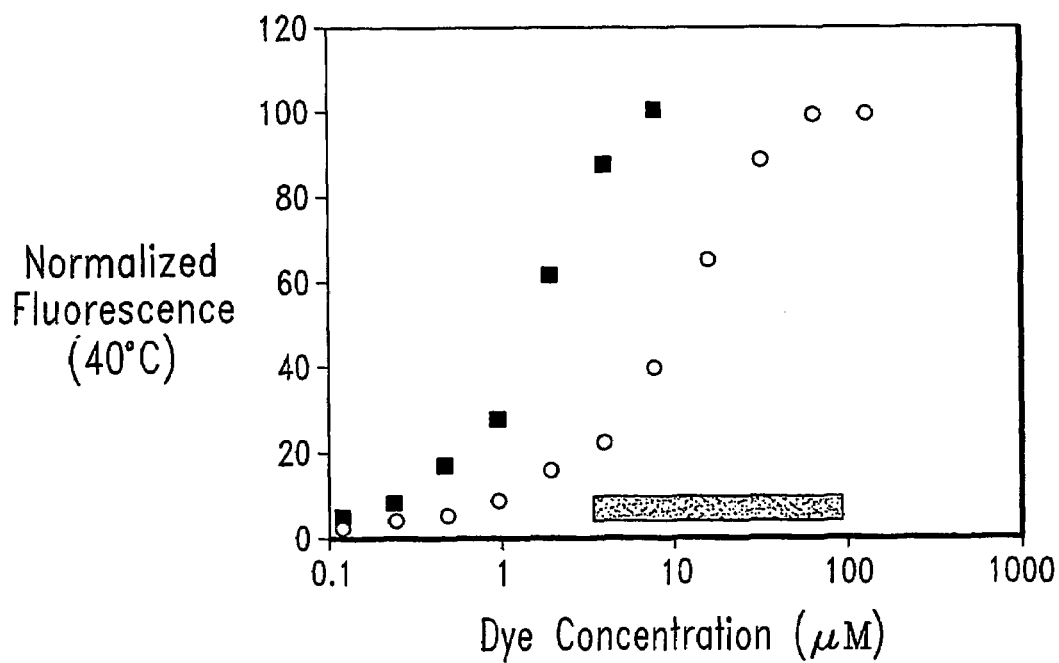
Figure 10:
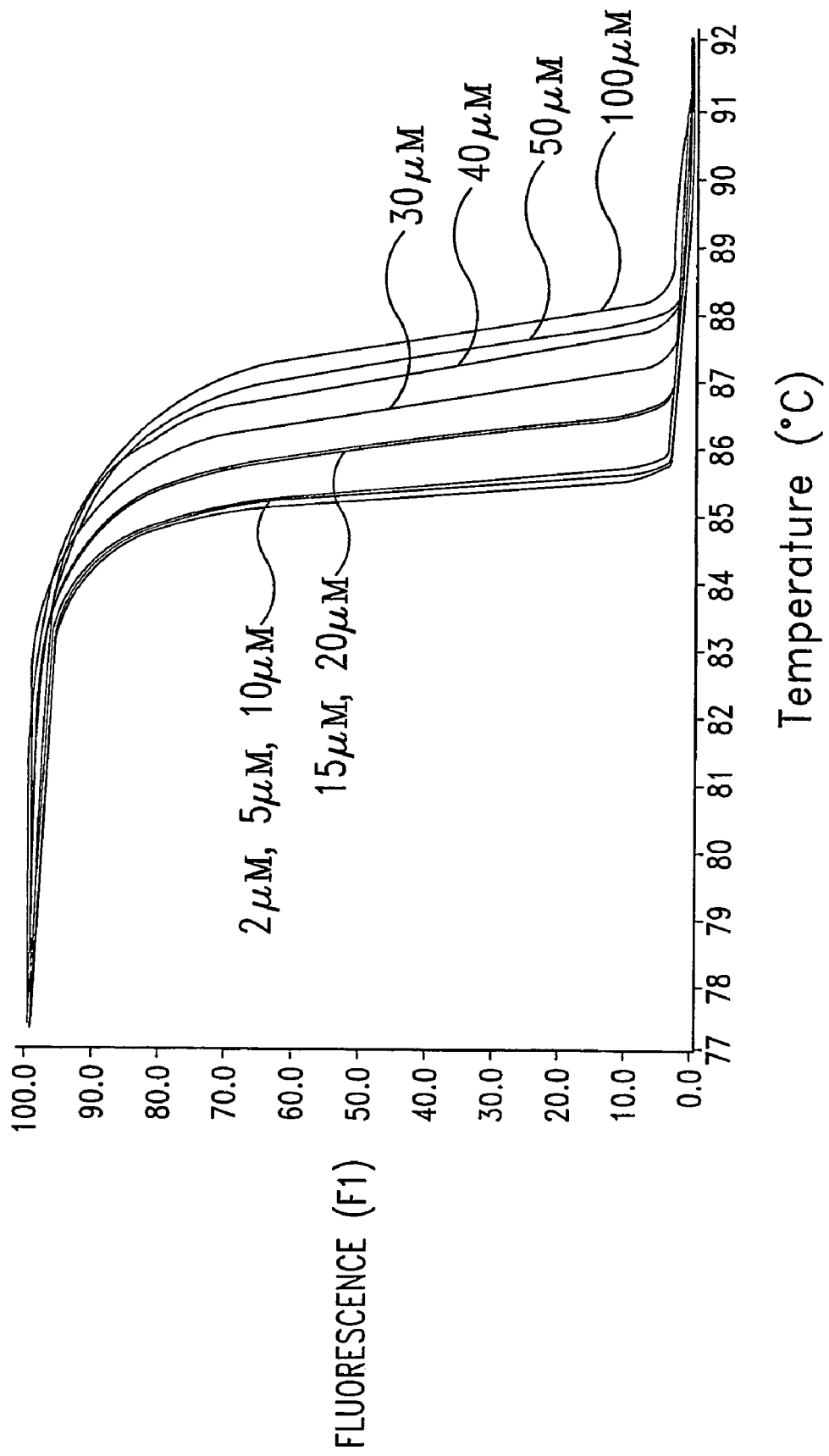
FIG. 10 illustrates the effect of dye concentrations on melting temperature.

FIGS. 9A-B show the concentrations of SYBR® Green I and LC Green that are compatible with PCR. At concentrations compatible with PCR, SYBR® Green I is far from saturating the amount of DNA typically present at the end of PCR. LightCycler Green, in contrast, can be used over a wide range of concentrations, including those that are saturating. Typical melting curves over a 50-fold range of LightCycler Green concentration are shown in FIG. 10.

EXAMPLE 9

Fluorescence Spectra of SYBR® Green I and LightCycler Green

The excitation and emission spectra of SYBR® Green I and LightCycler Green bound to DNA were measured on a Photon Technology fluorimeter (FL-1). LightCycler Green (10 µM) or SYBR® Green I (1:10,000) was added to 100 ng DNA (Low Mass DNA Ladder) in the presence of 3 mM $MgCl_2$, 50 mM Tris, pH 8.3, 250 µg/ml BSA and 200 µM each dNTP in a final volume of 60 µl.

Figure 11A:
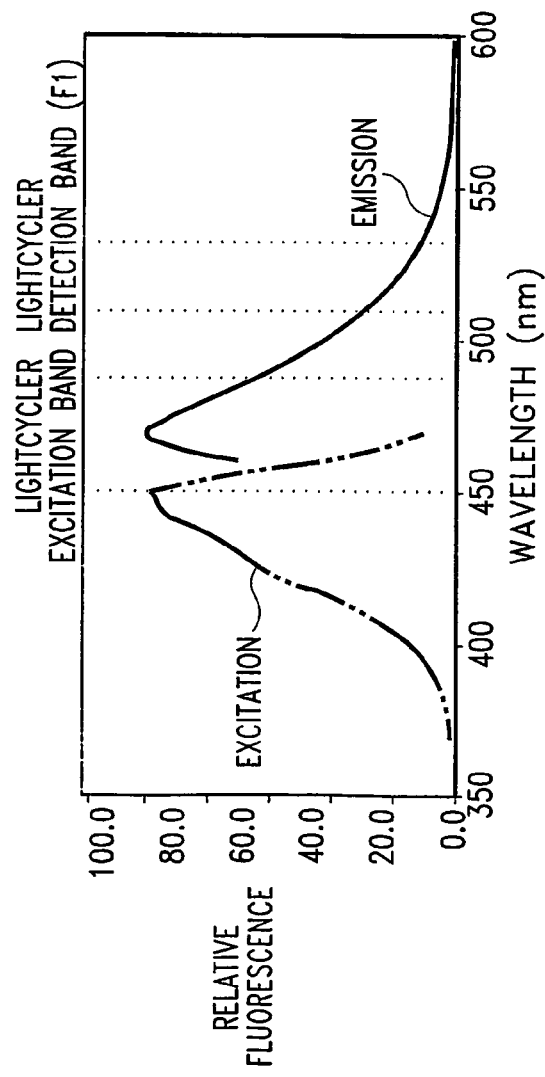
FIGS. 11A-B show the excitation and emission spectra for LightCycler Green (FIG. 11A) and SYBR® Green I (FIG. 11B).
Figure 11B:
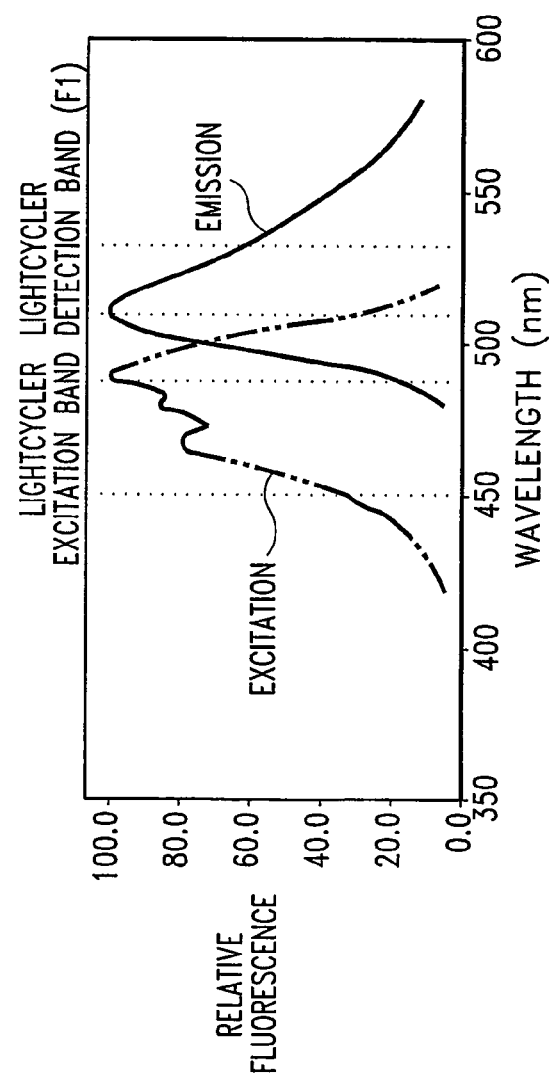

LightCycler® optics are well matched to SYBR® Green I excitation and emission (FIG. 11). Even though LightCycler Green is poorly matched to LightCycler® optics, the fluorescence signal observed on the LightCycler® with LightCycler Green at some PCR-compatible concentrations is greater than that usually observed from SYBR® Green I (data not shown).

EXAMPLE 10

Genotyping of Beta-Globin Gene Using X-Axis Adjustment and Fluorescence Difference Analysis A 110 bp fragment was amplified from the human beta globin region on chromosome 11 (accession# NG_000007). The 110 bp product included the sites of the common beta-globin mutations HbS and HbC. DNA was extracted from dried blood spots of 4 different individuals of each common genotype. The genotypes included 3 homozygous (AA, SS, and CC) and 3 heterozygous (AS, AC, and SC) types. The forward and reverse primers were ACACAACTGTGT-TCACTAGC (SEQ ID NO 3 ) and CAACTTCATCCACGT-TCACC (SEQ ID NO 4), respectively. Each 10 µl reaction contained 50 µg of genomic DNA, 0.50 µM each primer, 10 µM LC Green, 3 mM $MgCl_2$, 50 mM Tris, pH 8.3, 500 µg/ml bovine serum albumin, 0.2 mM each dNTPs, 0.04U/µl Klentaq™ (AB Peptides, St. Louis, Mo.), 88 ng TaqStart™ antibody (CloneTech, Palo Alto, Calif.). PCR reaction conditions were as follows: one pre-cycling denaturation at 95° C. for 5 sec; 35 cycles of 94° C. for 0 sec, 50° C. for 2 sec, 72° C. for 2 sec with a slope of 2° C. per second. Single fluorescence acquisitions were taken for each sample after the 2 sec extension. After PCR amplification, the samples were cooled at a programmed rate of −20° C./sec. Immediately following the rapid cooling, melting was performed on a custom 16-bit high resolution melting instrument from 70° C. to 93° C. at a rate of 0.30° C./sec while continuously acquiring fluorescence.

Figure 12A:
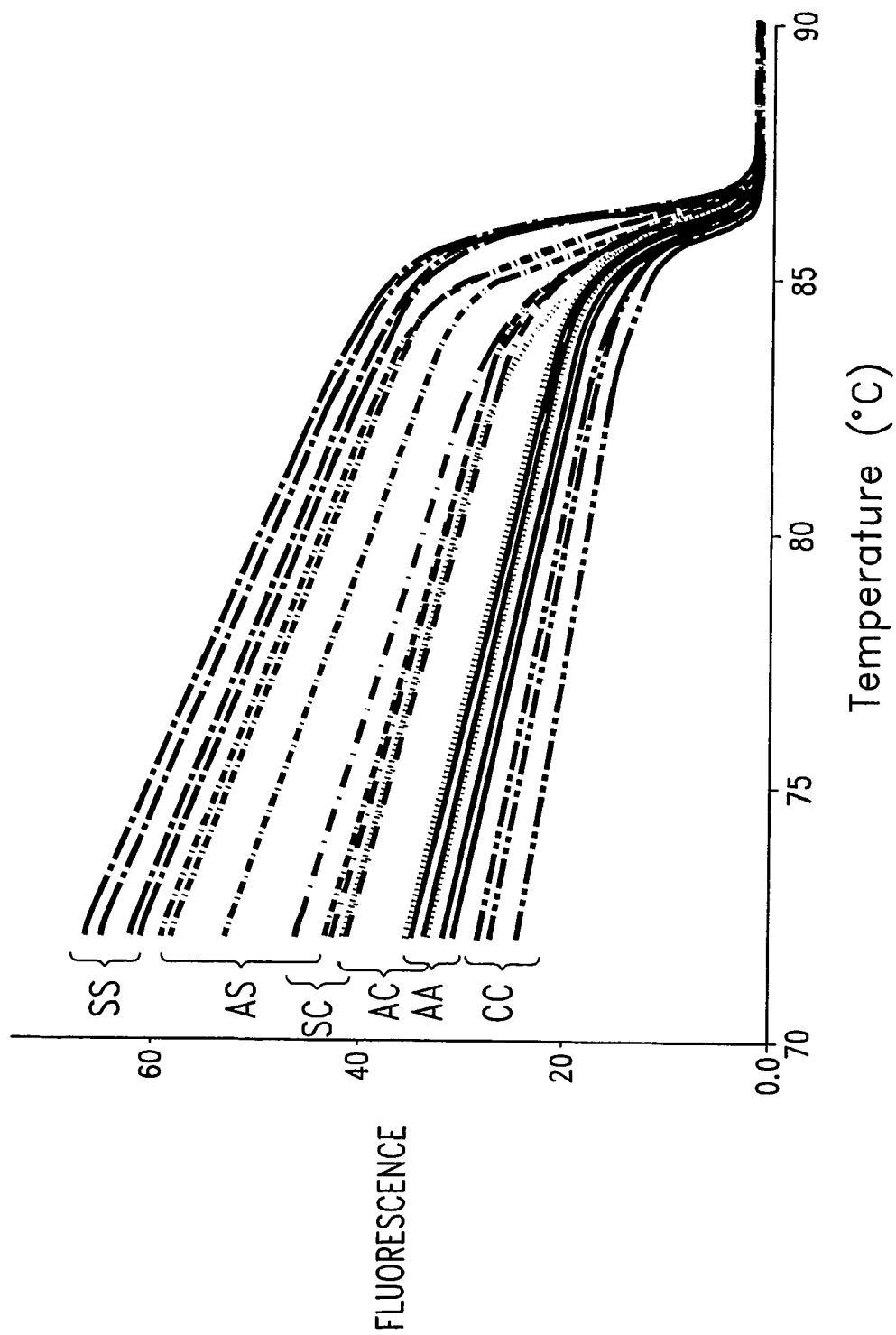
FIGS. 12A-D show high resolution melting curve analysis of quadruplicate samples of six different genotypes within a 110 bp fragment of beta-globin (--- SS, — AA, --- CC, --- SC, ......... AC, ..... AS)

High resolution melting curve data are obtained by measuring fluorescence as the temperature of the sample is increased. The original data from quadruplicate samples of 6 genotypes of beta-globin are shown in FIG. 12A. Note that the magnitude of the fluorescence is variable between different samples because of sample volume differences and variable capillary optics.

Figure 12B:
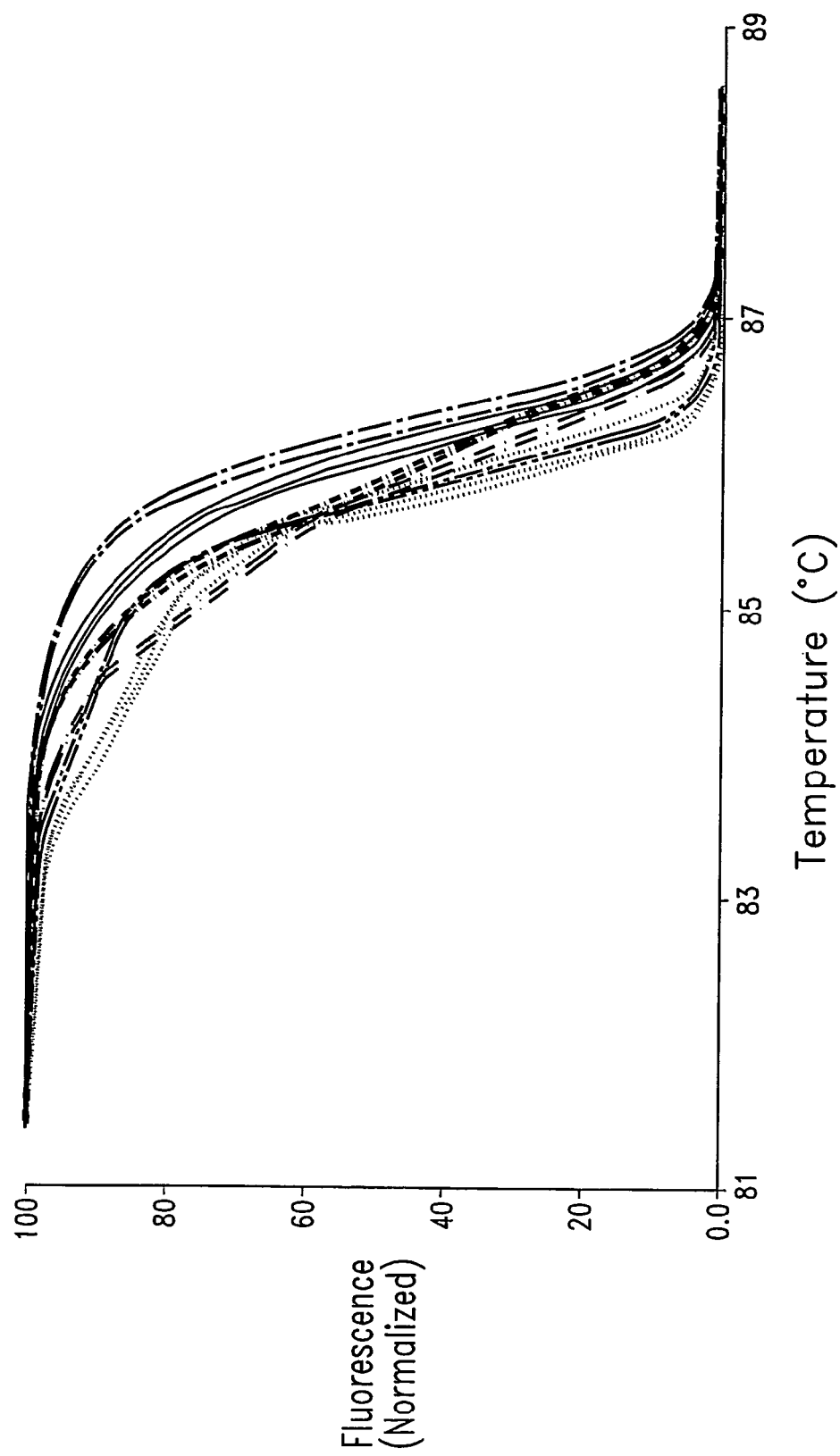

Magnitude differences between samples can be normalized by using linear baselines of each curve before and after the major transition. Specifically, two linear regions are selected, one before and one after the major transition. These regions define two lines for each curve, an upper 100% fluorescence line and a lower, 0% fluorescence line. The percent fluorescence within the transition (between the two regions) is calculated at each temperature as the percent distance between the extrapolated upper and lower lines. The normalized result for the beta globin data is shown in FIG. 12B. The quadruplicate samples of each genotype clearly group together, most clearly seen in this case around 84-85° C. There is still some variation within each genotype, secondary to temperature offsets between runs (note that there is about a 0.2° C. spread of quadruplicates within genotypes around 10-20% fluorescence). This sample variation can occur between two different samples or even between two different runs of the same sample. Different preparations, including preparations with different salt concentrations, can also provide a temperature offset. However, to at least a first approximation, these differences do not affect the shape of the curve.

Figure 12C:
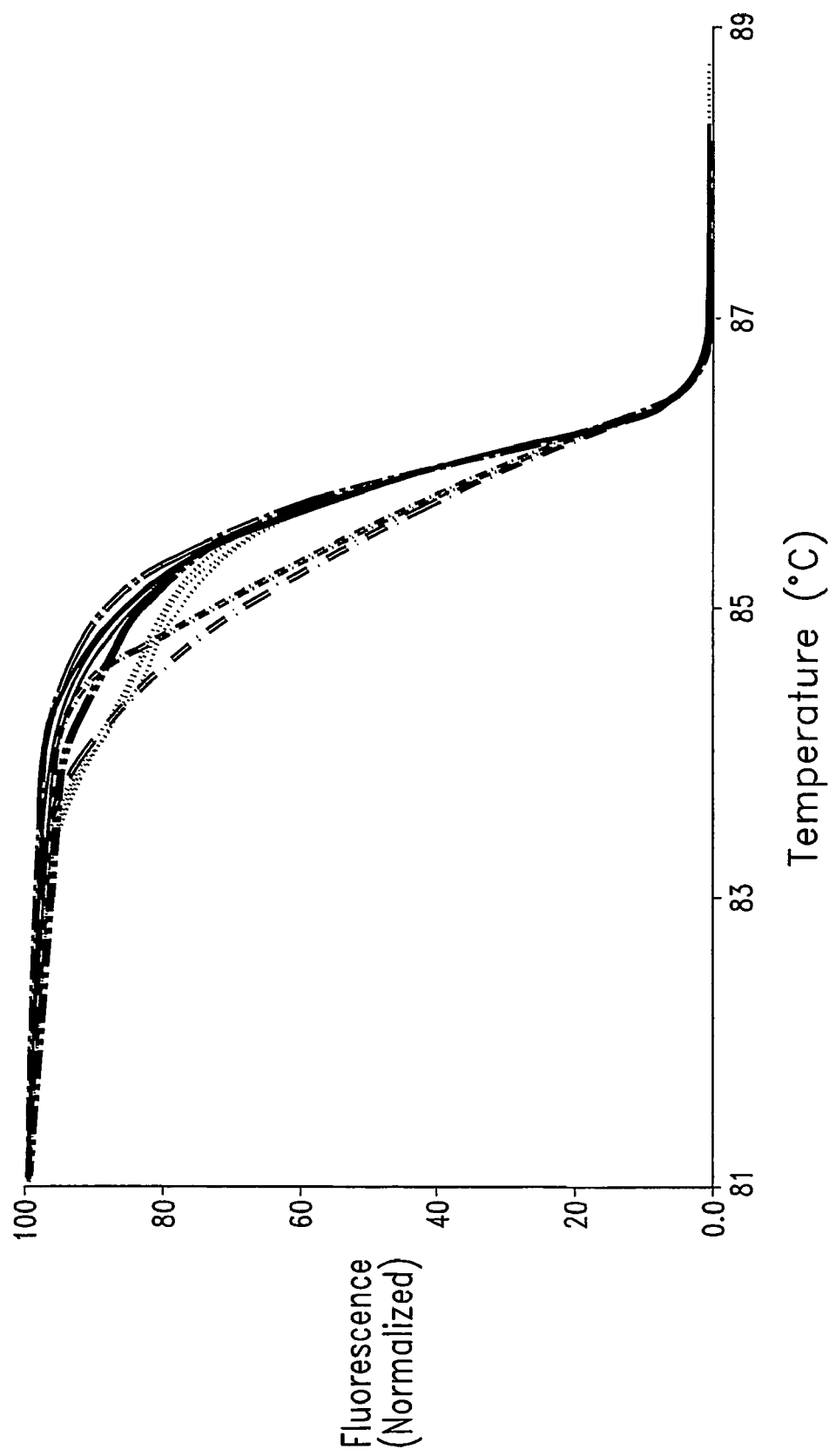

Temperature offsets between runs can be corrected by shifting the temperature axis of each curve so that they are superimposed over a given fluorescence interval. Illustratively, one sample is chosen as a standard, and the points within the florescence interval are fit to a quadratic. For each remaining curve, the required temperature shift for translation of each point within the fluorescence interval onto the quadratic is calculated. Each curve is then translated by the average shift to allow superimposition of the curves within the selected fluorescence interval. Amplification of a heterozygote produces low-temperature melting transitions of eroduplexes as well as higher melting transitions of homoduplexes. If the curves are shifted to superimpose their high temperature, homoduplex region (low percent fluorescence), heteroduplexes may be identified by their early drop in fluorescence at lower temperatures, as seen in FIG. 12C. However, since the shape of different homoduplexes does not vary much, temperature shifting different homoduplexes may obscure any difference between them.

Figure 12D:
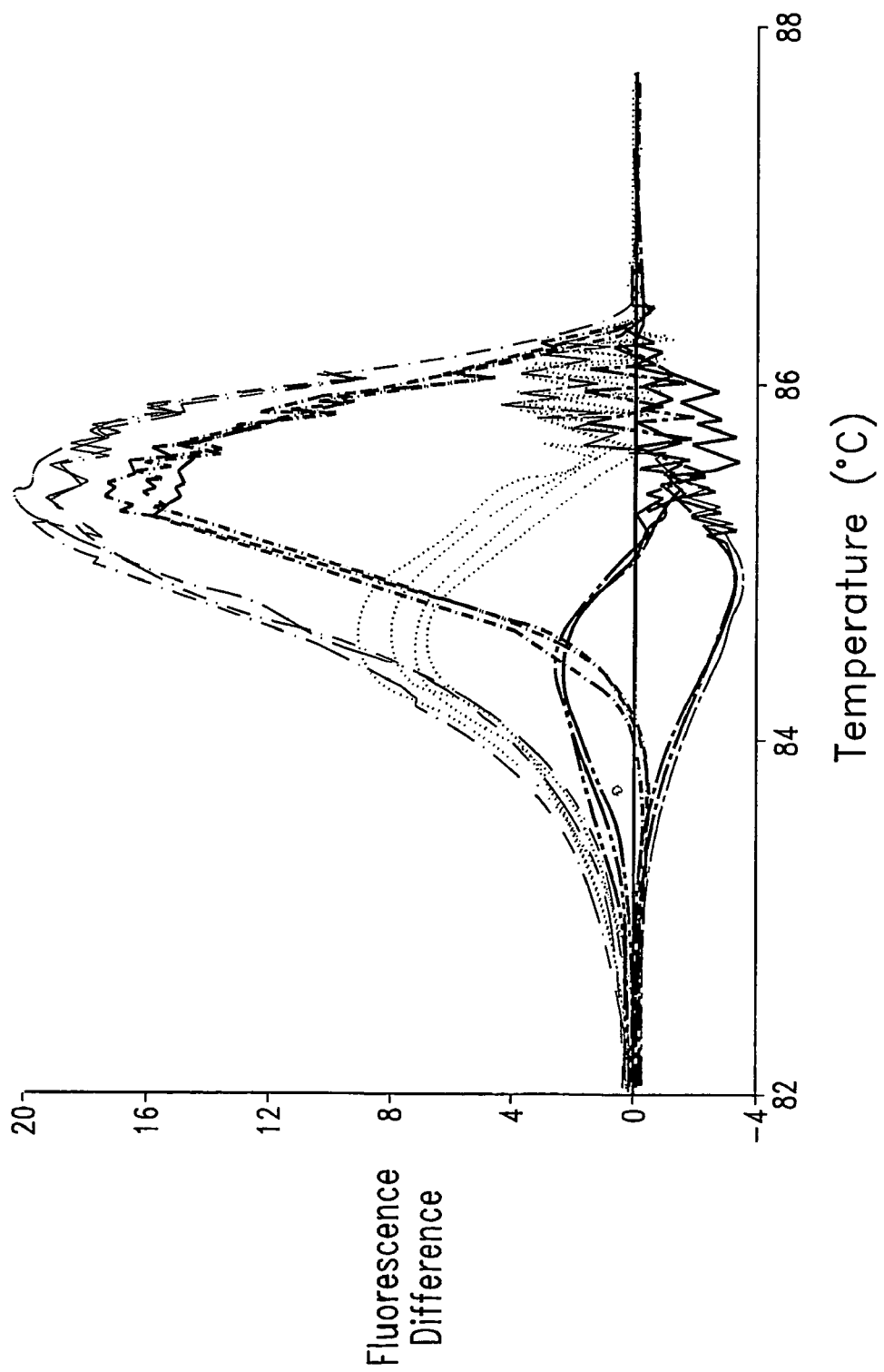

Finally, different genotypes are most easily observed by plotting the fluorescence difference between normalized (and optionally temperature shifted) melting curves. A standard genotype is first selected (illustratively, the beta-globin wild type AA is used). Then, the difference between each curve and the standard is plotted against temperature, as shown in FIG. 12D. The standard (subtracted from itself) is zero across all temperatures. Other genotypes trace unique paths and can be identified by visual pattern matching. Automated methods of feature extraction may also be used to assign genotypes. Additionally, while illustrative examples use saturating dyes and heteroduplex detection, it is understood that temperature shifting and temperature difference plots can be used for genotyping when heteroduplexes are not present, illustratively for use in viral genotyping wherein the genome is haploid. Examples of such high resolution genotyping include hepatitis C genotyping, human papilloma virus genotyping, HIV genotyping, and bacterial identification by ribosomal DNA amplification.

Single parameters that correlate with genotype can be devised. For example, normalized curves can be used to determine the temperature at which different genotypes are, say 10% melted (90% fluorescence). This clearly distinguishes some genotypes, but not others (FIG. 12B). Alternately, the maximum slope of the curve could be used to distinguish homozygotes from heterozygotes, but different homozygotes are often similar in maximum slope. Finally, the area under the difference curves (FIG. 12D) could be used to define genotype, but such curves can have similar area yet trace different paths. While a combination of parameters may prove to be effective for automated genotyping determination, this technique is well suited for visual pattern matching.

It is understood that other normalization techniques are available and are within the scope of the present invention. For example, the HR-1 (Idaho Technology, Salt Lake City, Utah) has a setting that will automatically adjust the fluorescence value at a predetermined temperature (illustratively a fluorescence value of 100 at 40° C.), and melting curves from all samples will be aligned from the same fluorescence value. The difference between the normalization described above and this machine-controlled normalization is that with the machine-controlled normalization, the slopes of the curve before and after the transition are not flattened.

EXAMPLE 11

Analysis of Larger Amplicons

While short amplicons often result in greater genotyping differences, LightCycler Green also may be used to genotype larger amplicons. DNA melting domains are usually about 50 to 500 bp in length, and larger amplicons, for example 500-800 bp, have multiple melting domains. A sequence alteration in one domain may not affect melting of the other domains, and the variation observed within a domain may be independent of amplicon length. Thus, while examples are provided in the 400-650 bp range, there may be no upper limit to the size of PCR product that can be scanned for the presence of sequence alterations.

Moreover, because the melting of one domain appears to be independent of the melting of other domains, an invariant domain may be used as an internal control to adjust the X-axis (temperature axis), due to instrument and/or sample run variation. Heterozygotes are distinguishable from each other and from homozygotes because the shapes of the melting curves are different. The shapes of the melting curves are defined by the stability and/or kinetic melting rates of the heteroduplexes and homoduplexes present. Because multiple melting domains are present in larger amplicons, the variation in shape may occur in any portion of the curve. By adjusting the X-axis positioning of multiple curves to overlap the invariant portion of the curve, the variable portion of the curve is much easier to discern. Alternatively, by overlapping the variable portion of the curves, if various genotypes are present, the rest of the curves will vary. X-axis adjustment alternatively could be performed by adding (1) an external control nucleic acid, or (2) a dye with a second emission wavelength that does not interact with nucleic acid but whose fluorescence is dependent on temperature (a dye with a good temperature coefficient such as Cy5) to each sample prior to PCR or to melting. Temperature-axis shifting should then be performed according to the position of the melting transition of the control nucleic acid or to the intensity profile of the control dye.

Figure 13A:
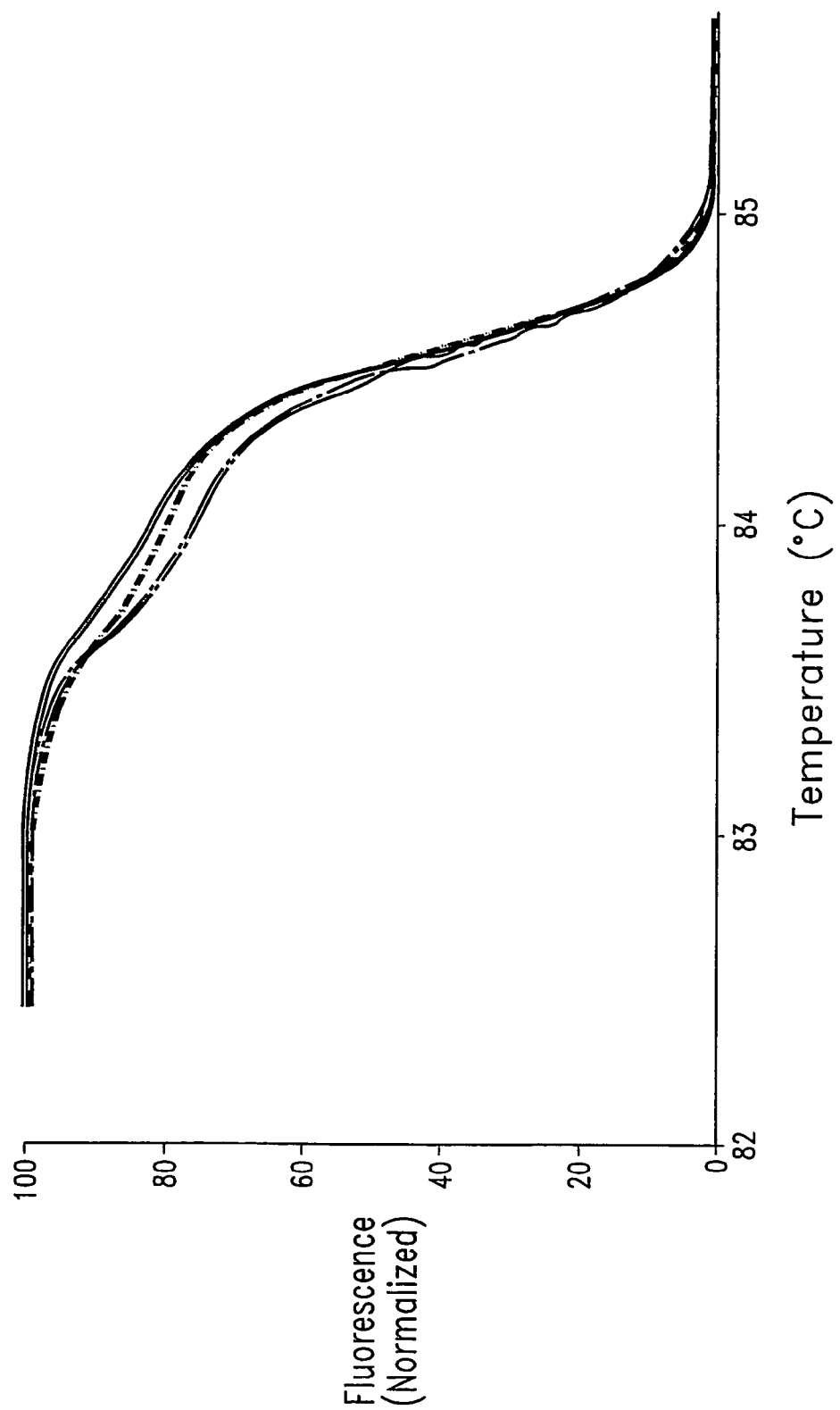
FIG. 13A shows melting curve analysis of duplicate samples of three genotypes of a 544 bp fragment of the human 5-Hydroxytryptamine receptor 2A (HTR2A) gene (--- TC, — CC, --- TT). The data have been normalized and temperature shifted using the portion between 10 and 20% fluorescence. A theoretical melting map of the homoduplex is shown as FIG. 13B. The position of the single nucleotide polymorphism is marked (X).
Figure 14:
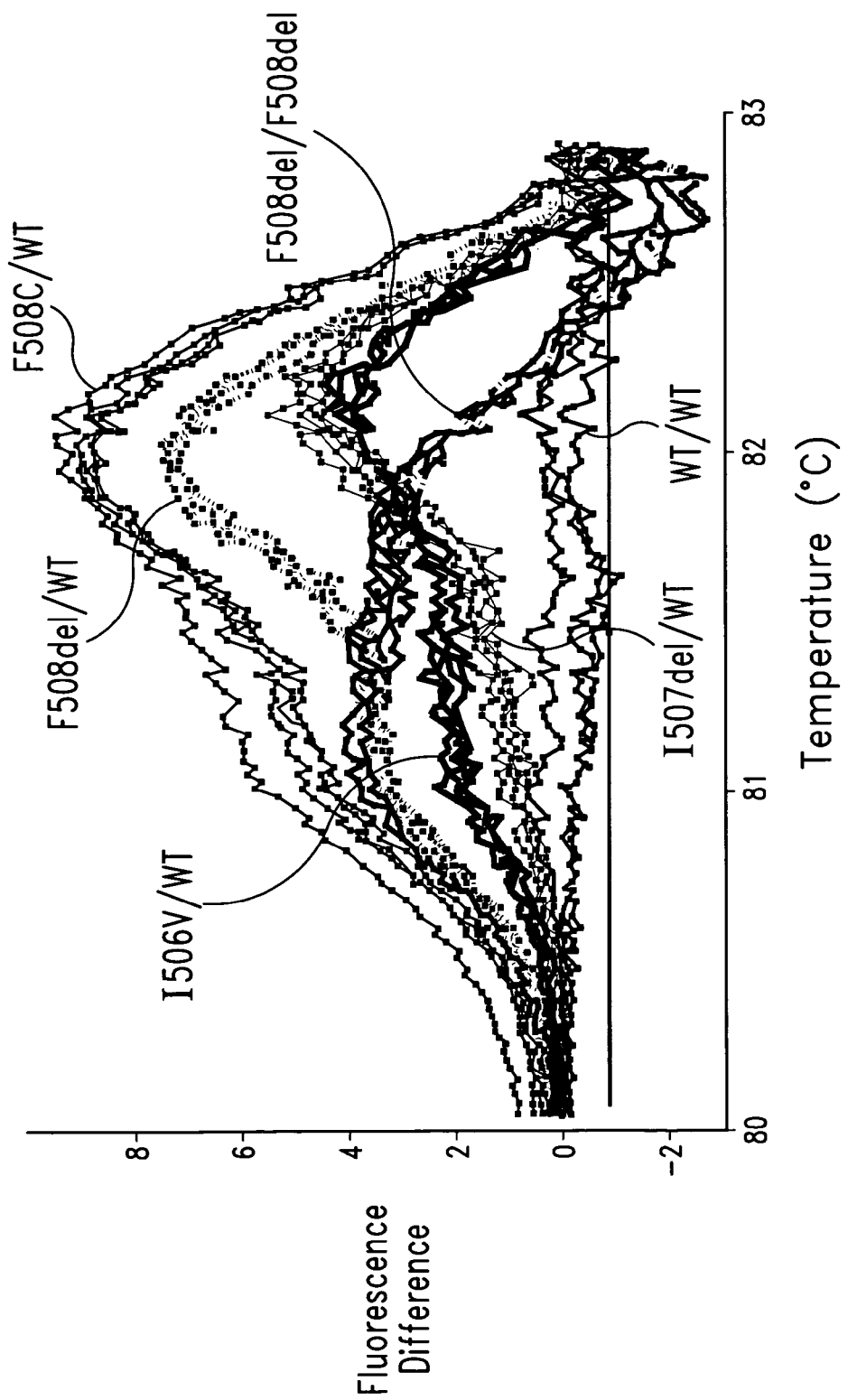
FIG. 14 shows a difference curve of six genotypes of a 612 bp fragment of the cystic fibrosis transmembrane conductance regulator (CFTR) gene. The plots have been normalized, temperature shifted by superimposing the portion between 30 and 40% fluorescence, and subtracted from one of the wild type plots.

FIGS. 13A and 14 illustrate two examples of analysis of larger amplicons. FIG. 13A shows amplification of a 544 bp fragment from the human 5-Hydroxytryptamine receptor 2A (HTR2A) gene, exon 2 (accession# NM_000621.1). The forward and reverse primers were CCAGCTCCGGGAGA (SEQ ID NO 5) and CATACAGGATGGTTAACATGG (SEQ ID NO 6), respectively. Each 10 µl reaction contained 50 ng of genomic DNA, 0.50 µM each primer, 1 µM LC Green, 2 mM $MgCl_2$, 50 mM Tris, pH 8.3, 500 µg/ml bovine serum albumin, 0.2 mM each dNTPs, 0.4U Klentaq™ (AB Peptides, St. Louis, Mo.), and 88 ng TaqStart™ antibody (CloneTech, Palo Alto, Calif.).

PCR reaction conditions were as follows: 40 cycles of 92° C. for 0 sec, 60° C. for 2 sec, 74° C. for 25 sec. After PCR amplification, the samples were cooled at a programmed rate of −20° C./sec. Immediately following the rapid cooling, melting was performed on a custom 16-bit high resolution melting instrument from 70° C. to 93° C. at a rate of 0.30° C./sec while continuously acquiring fluorescence.

Figure 13B:
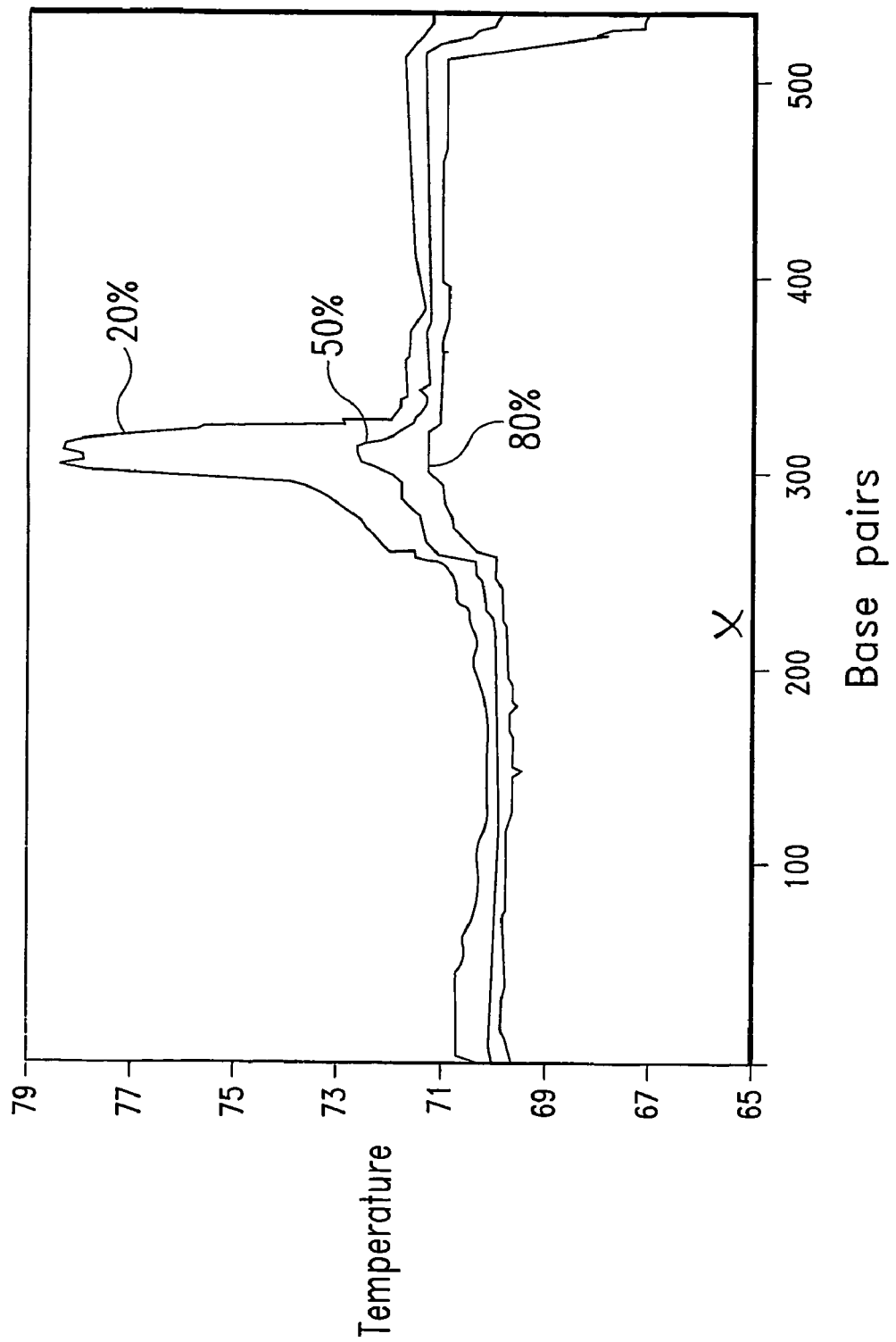

Duplicate samples of each genotype (CC, TC, and TT) were amplified and analyzed, as shown in FIG. 13A. The data was normalized and temperature shifted as described in Example 10, except that curves were superimposed between 10 and 20% fluorescence. FIG. 13B shows a predicted melting map of the homoduplex and the position of the polymorphism in the lower melting domain. The experimental data show two apparent melting domains. All genotypes are similar in the higher melting domain. Genotypes differ in the lower melting domain, where the heterozygote shows typical behavior of low melting heteroduplexes with the heterozygote curve crossing the lower melting homozygote curve and approximation to the higher temperature homozygote with increasing temperature.

FIG. 14 shows difference curves for amplification of a 612 bp fragment from the cystic fibrosis transmembrane conductance regulator (CFTR) gene, exon 10 (accession# M55115). The forward and reverse primers were AGAATATACACT-TCTGCTTAG (SEQ ID NO 7) and TATCACTATATG-CATGC (SEQ ID NO 8), respectively. Each 10 µl reaction contained 50 ng of genomic DNA, 0.50 µM each primer, 10 µM LC Green, 3 mM $MgCl_2$, 50 mM Tris, pH 8.3, 500 µg/ml bovine serum albumin, 0.2 mM each dNTPs, 0.4U Klentaq™ (AB Peptides, St. Louis, Mo.), and 88 ng TaqStart™ antibody (CloneTech, Palo Alto, Calif.). PCR reaction conditions were as follows; 35 cycles of 89° C. for 0 sec, 58° C. for 8 sec, 74° C. for 35 sec. Single fluorescence acquisitions were taken for each sample after the 35 sec extension. After PCR amplification, the samples were cooled at a programmed rate of −20° C./sec. Immediately following the rapid cooling, melting was performed on a custom 16-bit high resolution melting instrument from 60° C. to 87° C. at a rate of 0.30° C./sec while continuously acquiring fluorescence. In this example, heterozygote differentiation was best when the middle part of the curve (30-40% fluorescence) is used for X-axis adjustment. Finally, the fluorescence of each plot was subtracted from one of the wild type plots to give the difference plots shown in FIG. 14. Each sequence alteration is clearly different from the wild type and all genotypes can be differentiated.

EXAMPLE 12

Targeted Detection and Multiplexing With LightCycler Green

LightCycler Green may be used as a donor to excite an acceptor dye attached to an oligonucleotide probe. Because LightCycler Green may be used at or near saturating concentrations to bind to the hybridized probe at a high density (approximately two dye molecules every three base pairs), the dye is available throughout the length of double-stranded DNA for fluorescence resonance energy transfer. A probe with an acceptor dye is added to the reaction before PCR, amplified and is detected when hybridized to the product. The binding of LightCycler Green at high density to the duplex provides favorable excitation to the acceptor dye on the probe, producing a high degree of acceptor fluorescence. Previously, dyes with a high bp/dye ratio were used and only produced low levels of acceptor fluorescence.

Multicolor experiments can be performed with multiple probes. For example, total amplicon melting can be monitored at 470 nm, the emission of a fluorescein-labeled probe could be monitored at 515, a HEX-labeled probe (that hybridizes to a different segment of DNA internal to the primers) monitored at a third wavelength, and a TET-labeled probe (that hybridizes to yet a different segment internal to the primers) monitored at a 4th wavelength. Color compensation, as is well known in the art, is used to deconvolute the overlapping four signals. The result is that the first signal can be used to scan for mutations over the whole amplicon, while the 2nd, 3rd, and 4th signals allow genotyping of smaller regions within the amplicon.

EXAMPLE 13

Other dsDNA Binding Dyes

Table 1 summarizes the properties and characteristics of 37 different dyes. Twelve of the dyes tested did not produce a heteroduplex peak when a heterozygous delta F508 genotype was amplified (non-operative). A heteroduplex peak was detected with 25 of 37 different dyes (operative). The strongest heteroduplex signal occurred when LightCycler Green was used, with several other dyes also showing good heteroduplex signals. Most of the dyes that revealed heteroduplexes were compatible with PCR at saturating or near saturating concentrations. This correlation allows reasonable prediction of the dyes that can detect heteroduplexes by melting curve analysis. A 50% saturation provides reasonable prediction of heteroduplex detection. While missing some operative dyes, a percent saturation of about 80%, 90%, or even 99% may be used to identify dyes capable of detecting heteroduplexes.

Also, many of the operative asymmetrical cyanine dyes have a low bp/dye ratio at 50% saturation, particularly below 4.0 bp/dye and more particularly below 2.0 bp/dye. It was initially thought that because of this low bp/dye ratio, redistribution was prevented or minimized during the early stages of melting, and, thus, heteroduplexes were more easily detected. However, as seen in Table 1, it has been found that some dyes are able to detect heteroduplexes even with a substantially higher bp/dye ratio. Furthermore, dyes with a low bp/dye ratio can detect heteroduplexes even when present in concentrations substantially below saturation levels. Thus, a low bp/dye ratio is just one factor in identifying suitable dyes for heteroduplex formation.

The fluorescence is preferably stronger when the molar extinction coefficient is high (>30,000). The top two dyes (in terms of heteroduplex detection), show maximal excitation at 430-455 nm, and maximal emission at 450-480 nm. These are, in general, shorter wavelengths than usually employed in the fluorescein channel of typical real-time instruments. Even so, the fluorescence signal from LightCycler Green is greater than that obtained from SYBR® Green I, a surprising finding considering that SYBR® Green I has a much better wavelength match with the filters employed (FIG. 11).

TABLE 1

| | Dye Characteristics | | | Maximum PCR Compatible | | 50% saturation[5] | | |
|---|---|---|---|---|---|---|---|---|
| | Trade name | e[1] | Ex/Em[2] | dye (μM)[3] | % Sat[4] | bp/dye ratio | dye (μM) | % Het[6] |
| Non-operative | Ethidium Bromide | 5.2K | 518/605 | 16 | 12 | 0.15 | 97 | None |
| Non-operative | SYBR ® Green I | — | 489/510[a] | 1:5000[b] | 46 | — | — | None |
| Non-operative | SYBR ® Gold | — | 482/529[a] | 1:40960[b] | 7 | — | — | None |
| Non-operative | Pico Green | — | 472/503[a] | 1:640[b] | 17 | — | — | None |
| Non-operative | SYTOX ® Green | 67K | 484/516[a] | 0.5 | 17 | 8.8 | 1.7 | None |
| Non-operative | SYTOX ® Orange | 79K | 514/539[a] | 3.9 | 36 | 4.6 | 3.3 | None |
| Non-operative | TOTO ™-1 | 117K | 514/533 | 0.4 | 11 | 17 | 0.9 | None |
| Non-operative | YOYO ®-1 | 99K | 491/509 | 0.8 | 67 | 30 | 0.5 | None |
| Non-operative | SYTO ® 14 | 60K | 517/549 | 3.9 | 76 | 6.8 | 2.2 | None |
| Non-operative | SYTO ® 21 | 43K | 494/517 | 0.5 | 28 | 15 | 1.0 | None |
| Non-operative | SYTO ® 24 | 58K | 490/515 | 1.0 | 68 | 21 | 0.7 | None |
| Non-operative | SYTO ® 25 | 57K | 521/556 | 1.0 | 35 | 8.3 | 1.8 | None |
| Operative | LC Green | — | 450/469[a] | 63 | 99 | 1.5 | 10 | 13.6 |
| Operative | PO-PRO ™-1 | 50K | 435/455 | 50 | 100 | 2.3 | 6.5 | 11.2 |

TABLE 1-continued

|  | Dye Characteristics | | | Maximum PCR Compatible | | 50% saturation[5] | | %  |
|---|---|---|---|---|---|---|---|---|
|  | Trade name | e[1] | Ex/Em[2] | dye (μM)[3] | % Sat[4] | bp/dye ratio | dye (μM) | Het[6] |
| Operative | JO-PRO ™-1 | 94K | 530/546 | 12.5 | 100 | 7.1 | 2.1 | 10.5 |
| Operative | BO-PRO ™-1 | 58K | 462/481 | 3.1 | 75 | 4.8 | 3.1 | 10.2 |
| Operative | GelStar ® | — | 493/527 | 1:1280[b] | 99 | — | — | 8.9 |
| Operative | SYTO ® 45 | 43K | 455/484 | 125 | 100 | 1.5 | 10.2 | 8.9 |
| Operative | SYTO ® 44 | 56K | 446/471 | 31 | 86 | 1.4 | 10.5 | 8.3 |
| Operative | YO-PRO ®-1 | 52K | 491/509 | 6.3 | 87 | 8.3 | 1.8 | 7.9 |
| Operative | POPO ™-3 | 146K | 534/570 | 6.3 | 100 | 11 | 1.4 | 7.7 |
| Operative | SYTO ® 12 | 54K | 499/522 | 63 | 100 | 1.7 | 8.7 | 7.5 |
| Operative | TOTO ™-3 | 154K | 642/660 | 3.1 | 100 | 17 | 0.9 | 7.0 |
| Operative | SYTO ® 16 | 42K | 488/514 | 12.5 | 99 | 6.0 | 2.5 | 6.6 |
| Operative | Thiazole Orange | 63K | 510/525 | 16 | 27 | 0.34 | 44 | 6.0 |
| Operative | YOYO ®-3 | 167K | 612/631 | 3.1 | 100 | 15 | 1.0 | 6.0 |
| Operative | SYTO ® 43 | 48K | 436/471 | 125 | 100 | 0.83 | 18.0 | 5.3 |
| Operative | SYTO ® 11 | 75K | 508/527 | 16 | 100 | 4.7 | 3.2 | 4.6 |
| Operative | SYTO ® 13 | 74K | 488/509 | 1.0 | 50 | 8.8 | 1.7 | 4.6 |
| Operative | SYTO ® 15 | 55K | 516/546 | 7.8 | 77 | 4.2 | 3.6 | 4.6 |
| Operative | BOBO ™-3 | 148K | 570/602 | 3.1 | 85 | 8.3 | 1.8 | 4.6 |
| Operative | LO-PRO ™-1 | 102K | 567/580 | 6.3 | 83 | 6.0 | 2.5 | 4.4 |
| Operative | SYTO ® 23 | 46K | 499/520 | 3.9 | 70 | 5.4 | 2.8 | 4.3 |
| Operative | TO-PRO ®-1 | 63K | 515/531 | 1.6 | 67 | 17 | 0.9 | 3.6 |
| Operative | SYTO ® 20 | 64K | 512/530 | 1.5 | 23 | 4.3 | 3.5 | 2.5 |
| Operative | BOBO ™-1 | 114K | 470/535 | 1.6 | 42 | 8.8 | 1.7 | 0.9 |
| Operative | POPO ™-1 | 93K | 434/456 | 1.6 | 48 | 8.8 | 1.7 | 0.3 |

[1]Molar extinction coefficient, according to manufacturer's data.
[2]Fluorescence spectra either provided by the manufacturer, or (superscript a) obtained in a fluorimeter using 2.5 μM bp (100 ng/60 μl) of dsDNA and dye at maximum PCR compatible concentration in PCR buffer (3 mM $MgCl_2$, 50 mM Tris, pH 8.3, 200 μM each dNTP, 500 μg/ml BSA). Ex = excitation maxima; Em = emission maxima.
[3]Maximum concentration of dye that can be present in a PCR mixture that allows amplification without significant inhibition. Some dye concentrations are expressed as dilution factors from material supplied by the manufacturer (superscript b).
[4]Percent fluorescence at maximal PCR compatible dye concentration compared to fluorescence of the same dye at saturating concentration, i.e., the concentration that provides the highest fluorescence intensity possible, all in the presence of 15 μM bp DNA (100 ng dsDNA/10 μl) and PCR buffer.
[5]Concentration of dye, or bp/dye ratio required to produce 50% of the maximum fluorescence intensity that is obtainable, i.e., the intensity at saturation, in the presence of 15 μM bp DNA.
[6]Percentage peak area of the heteroduplex signature peak as measured with 450-490 nm excitation and 510-530 nm detection optics on the HR-1 high resolution instrument, using a melting curve of the 44 bp amplicon of the del F508 heterozygote of Example 5, obtained at a heating ramp of 0.3° C./s.

EXAMPLE 14

Preparation and Use of Pyrimidinium-Based DNA Binding Dyes

Certain embodiments of dyes having the following pyrimidinium core structure have been prepared:

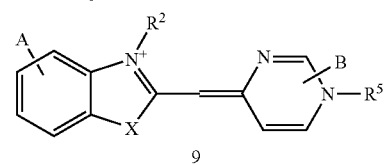

wherein ☒, X, $R^2$, $R^3$, and $R^5$ are as defined herein for Formula I, and B is as defined in Formulae V.

While there are many ways of preparing dyes having this formula, one method is as follows:

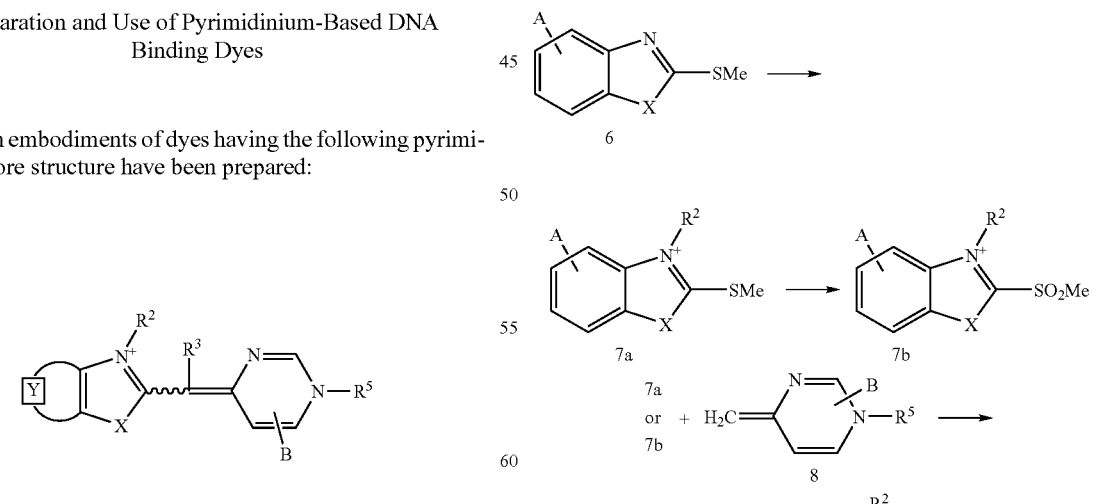

where compounds 6 are commercially available, or may be prepared by conventional methods. Compounds 7a are prepared by alkylation of 6 at N(3) using alkylating agents such as alkyl halides, alkylsulfates, and the like, under neutral or basic conditions, including alkyllithiums, aromatic and aliphatic amines, $K_2CO_3$, and the like. Similarly, compounds 7a are prepared by arylation of 6 at N(3) by aromatic coupling reactions of aromatic halides, boronates, and the like, which are catalyzed by metal compounds, such as copper, palladium, platinum, and like catalysts. Compounds 7b are prepared from compounds 7a by conventional oxidation, such as reactions using hydrogen peroxide, peroxy acids, including m-CPBA, and the like. In some cases, compounds 7a or compounds 7b are commercially available. Compounds 8 are commercially available or are prepared by conventional methods, such as alkylation or arylation at N(1), as described herein. Alternatively, compounds 8 are prepared by condensation of appropriately substituted 1,3-diones and ureas or thioureas. Further, compounds 8 having leaving groups, as defined herein and including halides, alkylsulfonyls, arylsulfonyls, and the like, at C(2) may be modified by introducing nucleophiles, such as nitrogen, oxygen, and sulfur-based nucleophiles, at C(2) under neutral or basic conditions. Further, compounds 8 having oxygen or sulfur nucleophilic groups at C(2) may be modified by introducing alkylating or acylating agents at the C(2) hydroxy or thiol under neutral or basic conditions. Compounds 9 are prepared by reacting compounds 7 and compounds 8 under neutral or basic conditions, as described herein.

Exemplary compounds having this formula were prepared as herein described, purified by BPLC using triethylamine-ammonium acetate as the mobile phase, and isolated as their corresponding acetate salts. These exemplary compounds are illustrated in Table 2.

TABLE 2

| Dye | Y | X | $R^2$ | $R^5$ | B |
|-----|---|---|-------|-------|---|
| G5 | phenyl | S | Ph | $H_2C$-CH$_2$-$N^+$(Me)$_2$-Me | H |
| H5 | $F_2CH-S(O)_2$-phenyl | S | Me | $H_2C$-CH$_2$-$N^+$(Me)$_2$-Me | H |
| D6 | phenyl | S | Me | $H_2C$-CH$_2$-$N^+$(Me)$_2$-Me | H |
| E6 | phenyl | O | Me | $H_2C$-CH$_2$-$N^+$(Me)$_2$-Me | H |
| P6 | Cl-phenyl | S | $H_2C$-CH$_2$-CH$_2$-$SO_3^-$ | $H_2C$-CH$_2$-$N^+$(Me)$_2$-Me | H |
| R6 | $H_2N$-phenyl | S | Me | $H_2C$-CH$_2$-$N^+$(Me)$_2$-Me | H |
| Y6 | naphthyl | O | Me | $H_2C$-CH$_2$-$N^+$(Me)$_2$-Me | H |

TABLE 2-continued

| Dye | Y | X | R² | R⁵ | B |
|---|---|---|---|---|---|
| Z6 | naphthyl | S | Me | H₂C-CH₂-N⁺(Me)₃ | H |
| D8 | phenyl | S | Me | Ph | 2-SH 6-Me |
| I5 | 4-Me-phenyl | S | H₂C-CH₂-CH₂-SO₃⁻ | H₂C-CH₂-N⁺(Me)₃ | H |
| K5 | 4-Cl-phenyl | S | Me | H₂C-CH₂-N⁺(Me)₃ | H |
| L5 | 4-NO₂-phenyl | S | Me | H₂C-CH₂-N⁺(Me)₃ | H |
| G8 | phenyl | S | Me | Ph | 2-SCH₃ 6-Me |
| K8 | 4-Cl-phenyl | S | H₂C-CH₂-CH₂-SO₃⁻ | Ph | 2-SH 6-Me |
| L8 | N-methylpyridinium | S | None | Ph | 2-SH 6-Me |
| I8 | naphthyl | S | Me | Ph | 2-SH 6-Me |
| M8 | phenyl | S | Me | Ph | 2-S-pyrimidine 6-Me |
| N8 | phenyl | S | Me | Ph | 2-SH 6-Ph |

TABLE 2-continued

| Dye | Y | X | R² | R⁵ | B |
|-----|---|---|-----|-----|---|
| C8 | (benzo ring) | S | Me | Ph | 2-NH₂ 6-Me |
| E8 | (benzo ring) | S | Me | Ph | 2-OH 6-Me |
| F7 | (benzo ring) | S | Me | Ph | 2-(4,4-dimethyl piperazine) 6-Me |
| O8 | (benzo ring) | S | Me R³=C(O)Ph | Ph | 2-SH 6-Me |

Compound D6 was prepared by first reacting 4-methylpyrimidine with (3-bromopropyl)trimethylammonium bromide in acetonitrile at reflux The resulting product (compound A6) in acetonitrile was reacted with 3-methyl-2-methylsulfonyl-benzothiazolium iodide (available from Aldrich) in the presence of anhydrous pyridine and triethylamine at reflux under argon.

Compound E6 was prepared according to the general procedure used to prepare compound D6 from 3-methyl-2-methylsulfonylbenzoxazolium iodide (prepared by reacting 2-methylsulfonylbenzoxazole with dimethylsulfate) and compound A6.

Compound G5 was prepared according to the general procedure used to prepare compound D6 from 2-methylthio-3-phenylbenzothiazolium (Aldrich) and compound A6.

Compound H5 was prepared according to the general procedure used to prepare compound D6 from 5-difluoromethylsulfonyl-3-methyl-2-methylthiobenzothiazolium methylsulfate (prepared by reacting 5-difluoromethylsulfonyl-2-methylthiobenzothiazole, available from Aldrich, with dimethylsulfate) and compound A6.

Compound P6 was prepared according to the general procedure used to prepare compound D6 from 5-chloro-2-(methylthio)-3-(3-sulfopropyl)-benzothiazolium hydroxide (Aldrich) and compound A6.

Compound R6 was prepared according to the general procedure used to prepare compound D6 from 6-amino-3-methyl-2-methylthiobenzothiazolium methylsulfate (prepared by reacting 6-amino-2-methylthiobenzothiazole, available from Aldrich, with dimethylsulfate) and compound A6.

Compound Y6 was prepared according to the general procedure used to prepare compound D6 from 3-methyl-2-methylsulfonylnaphtho[1,2-d]oxazolium methylsulfate (prepared by reacting 2-methylsulfonylnaphtho[1,2-d]oxazole, available from Chem Bridge Product List, San Diego, Calif., with dimethylsulfate) and compound A6.

Compound Z6 was prepared according to the general procedure used to prepare compound D6 from 3-methyl-2-methylsulfonylnaphtho[1,2-d]thiazolium methylsulfate (prepared by reacting 2-methylsulfonylnaphtho[1,2-d]thiazole, available from Specs, Rijswijk, The Netherlands, with dimethylsulfate) and compound A6.

Compound D8 was prepared by heating a solution of N-phenylthiourea and 2,4-pentanedione in HCl/EtOH at reflux. The resulting pyrimidinthione was reacted with 3-methyl-2-methylsulfonylbenzothiazolium iodide in the presence of triethylamine in chloroform/methanol (10:1) at reflux overnight to give compound D8.

Compounds I5, K5, L5, G8, K8, L8, I8, M8, N8, C8, E8, F7, and O8 may be prepared by similar methods described above. It is expected that these dyes would be useful for detection of heteroduplexes.

The pyrimidinium-based cyanine dyes described herein, illustratively G5, H5, D6, E6, P6, R6, Y6, Z6, and D8, are novel and can be used for the detection of heteroduplexes, mutation scanning and genotyping. The results of using these dyes in the detection of heteroduplexes are summarized in Table 3. It is noted that the percent heteroduplex for LC Green is greater in Table 3 than in Table 1. This difference is likely due to the larger amplicon used in obtaining the data shown in Table 3.

TABLE 3

| Dye | Ex/Em[1] | Maximum PCR compatible % Sat[2] | % Het[3] |
|-----|----------|----------------------------------|----------|
| LC Green | 450/469 | >99% | 20.5% |
| PO-PRO ™-1 | 438/457 | 100% | 19.6% |
| BO-PRO ™-1 | 438/457 | 100% | 17.1% |
| D6 | 457/471 | 92% | 23.3% |
| E6 | 425/454 | >99% | 15.0% |
| P6 | 464/490 | 100% | 21.0% |
| R6 | 453/470 | >90% | 15.0% |
| G5 | 442-458/475 | 100% | 20.0% |
| H5 | 444/459 | 100% | 22.5% |
| Y6 | 439/477-515 | 100% | 21.0% |

TABLE 3-continued

| Dye | Ex/Em[1] | Maximum PCR compatible % Sat[2] | % Het[3] |
|---|---|---|---|
| Z6 | 469/494-526 | 100% | 13.4% |
| D8 | 453-457/471 | 100% | 19.8% |

[1]Excitation maxima (Ex) and emission maxima (Em) obtained in a fluorimeter using 2.5 µM bp (100 ng/60 µl)of dsDNA and dye at maximum PCR compatible concentration in PCR buffer (3 mM $MgCl_2$, 50 mM Tris, pH 8.3, 200 µM each dNTP, 500 µg/ml BSA). Some dyes have a range due to the broad emission or excitation peak.
[2]Maximum amount of dye that can be present in a PCR mixture that allows amplification without significant inhibition, expressed as percentage of fluorescence compared to fluorescence of the same dye at saturating concentration, i.e., the concentration that provides the highest fluorescence intensity possible, all in the presence of 15 µM bp DNA (100 ng dsDNA/10 µl) and PCR buffer.
[3]Percentage peak area of the heteroduplex signature peak as measured with 420-490 nm excitation and 450-530 nm detection optics, using the del F508 heterozygote melting curve obtained at a heating ramp of 0.3° C./s. The amplicon used in this set of experiments were 57 bp long generated by primers GGCACCATTAAAGAAAATAT (SEQ ID NO: 23) and TCTGTATC-TATATTCATCATAGG (SEQ ID NO: 24) Maximum % obtained was recorded.

EXAMPLE 15

High Resolution Melting Curve Analysis for Genotype Comparison

Dyes of the invention can be used to determine whether any two individuals share the same alleles on a gene fragment. In the previous examples, the genotype (including the exact allele, heterozygosity, and haplotype) of a reference sample was known. In some applications, the exact genotype of a reference sample need not be known, as long as high-resolution melting curve analysis makes it possible to determine whether a sample of another individual (or of unknown origin) is the same as the reference. An illustrative example is the identification of HLA alleles shared among family members.

Human Leukocyte Antigens (HLA) are cell surface proteins of white blood cells and other tissues of the body which play a key role in immune recognition, and thus in transplant tolerance or rejection. Matching of HLA alleles between donor and recipient is important for organ transplant. HLA proteins form two major groups: class I, and class II. Each group is encoded by multiple genes. The currently accepted techniques for determining the HLA allelotype of a tissue include serotyping with specific antibody reagents, hybridization with nucleic acid probes, and direct sequencing of the HLA genes. Because a large number of genes and loci need to be tested, the cost to determine the HLA allelotype is over $1,000 per person. Complete genotyping of HLA is necessary when donor and recipient are unrelated. However there is about a 25% chance of a perfect HLA match between siblings and for this reason organ transplant between siblings is preferred when HLA matches indicate that it is possible. In this case it is only necessary to demonstrate that the donor and recipient relatives share the same HLA alleles. Determining the exact identity of the shared alleles is not necessary.

Figure 15:
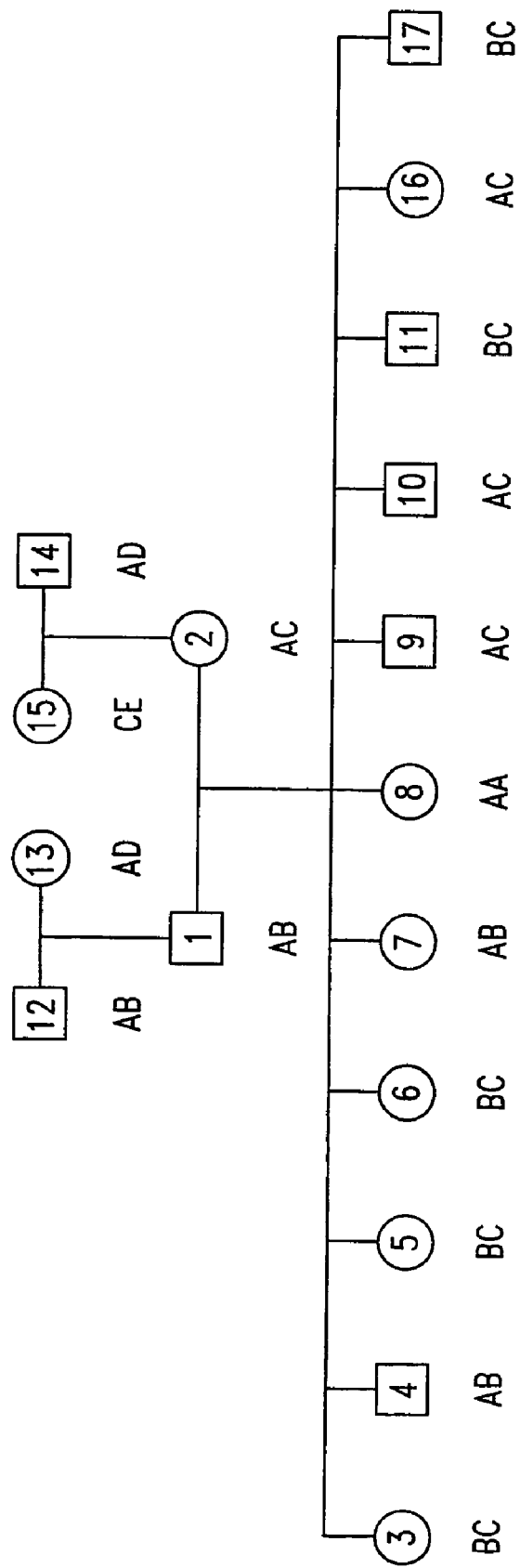
FIG. 15 shows the pedigree of CEPH referenced Utah family 1331.

Genomic DNA samples of CEPH/Pedigree Utah family 1331 were obtained from the Coriell Institute. There are 17 people across three generations in this family including four internal grandparents, two parents, and eleven children (pedigree of family 1331 is shown in FIG. 15). Two other samples with well known homozygous genotypes of HLA-A BM15 (0101) and BM16(0202) were also obtained from Coriell.

Amplification of two exons of the HLA-A gene were performed as follows: HLA class I genes are so similar over of the length of their coding exons that it is difficult to design PCR primers that amplify only the HLA-A gene and not the related class I genes. A nested PCR strategy was adopted in which an initial round of PCR specifically amplified a large (948 bp) fragment of the HLA-A gene followed by secondary amplification of that product using internal primers. The primers used in the first PCR hybridized to HLA-A intron 1 (forward primer 5'-GAAAC(C/G)GCCTCTG(C/T)GGG-GAGAAGCAA (SEQ ID NO 9, SEQ ID NO 10, SEQ ID NO 11, SEQ ID NO 12)) and intron 4 (reverse primer 5'-TGTTG-GTCCCAATTGTCTCCCCTC (SEQ ID NO 13)). In the secondary PCRs the forward primers 5'AGCCGCGCC(G/T) GGAAGAGGGTCG (SEQ ID NO 14, SEQ ID NO 15) and reverse primer 5'GGCCGGGGTCACTCACCG (SEQ ID NO 16) were used to amplify a 335 bp segment of HLA-A exon 2. The forward 5'CCC(G/A)GGTTGGTCGGGGC (SEQ ID NO 17, SEQ ID NO 18) and reverse primer 5'ATCAG(G/T) GAGGCGCCCCGTG (SEQ ID NO 19, SEQ ID NO 20) were used to amplify a 366 bp fragment of HLA-A exon 3. In the primer sequences of this example, (N/N') represents that the primer is a mixture of nucleotide sequences having equal percentages of N and N' at that position. For example, the forward primer for the 335 bp segment of HLA-A exon 2 contains an equal mixture of two nucleotides, with either a G or an A at the fourth position, as represented by SEQ ID NO 17 and SEQ ID NO 18. The forward primer for the HLA-A intron 1 has two such sites, and thus is an equal mixture of four nucleotides, as represented by SEQ ID NO 9,SEQ ID NO 10, SEQID NO 11 and SEQID NO 12.

All PCRs were performed in glass capillaries using the Roche LightCycler®. The initial PCR contained 0.5 µM forward and reverse primers, 50 ng genornic DNA in a buffer of 3 mM $Mg^{++}$, 50 mM Tris-HCl pH 8.3, 500 µg/ml BSA and 20 µM of dye D6 in 10 µl. Cycling conditions were 94° C. for 20 s followed by 40 cycles of 94° C. 1 s, 62° C. for 0 s, 72° C. for 1 min. The secondary, nested PCRs contained 0.25 µM forward and reverse primer, 1/10000 of first PCR product in the same buffer containing 2 mM $Mg^{++}$. Cycling conditions were 94° C. for 5 s followed by 25 cycles with 94° C. 1 s, 65° C. for 0 s, 72° C. for 8 s.

After the secondary amplification the glass capillaries were transferred to the high resolution melting instrument HR-1, and a melt was performed. The sample was heated from 60° C. to 95° C. at a rate of 0.3° C./s and fluorescence (450 excitation/470 emission) and temperature measurements were acquired every 40 s (FIGS. 16A-B). The nested sequencing products were sequenced by the ABI 3700. Sequencher version 4.0 was used for the sequence analysis.

Concordance of melting curve analysis and sequencing results were determined as follows: Melting curve analysis of the exon 2 and exon 3 PCR products amplified from the 17 members of the CEPH/Pedigree Utah family 1331 clustered in six different groups (FIGS. 16A-B). This suggested that there are six different HLA-A genotypes in this family. The exon 2 and exon 3 PCR products were sequenced, and the results confirmed the melting curve analysis, identifying the six genotypes as: HLA-A 02011/3101 (herein referred to as genotype AB) for family members 1, 4, 7,12; HLA-A 3101/2402101 (genotype BC) for family members 3,5,6,11,17; HLA-A 02011/2402101 (genotype AC) for family members 2, 9, 10, 16, HLA-A 02011/03011 (genotype AD) for family members 13, 14; HLA-A 02011/02011 (genotype AA) for family member 8 and HLA-A 2402101/01011 (genotype CE) for family member 15 (Results for exon 2 is shown in FIGS. 16A-B).

In some cases, the amplification products from siblings may show identical or nearly identical melting curves despite having different genotypes. In such cases mixing the genomic DNA from the two siblings before the initial PCR followed by the two amplification steps and melting curve analysis can differentiate identical from non-identical genotypes. In particular if the siblings have identical genotypes, the mixed melting curve will be identical to those performed separately. If siblings have different genotypes then the mixed melting curve will be different from that of the individual melting curves. Mixing experiments within each group confirmed that the members of each group shared identical genotypes.

Another example of the mixing analysis technique was demonstrated by two homozygous samples BM15 (0101) and BM16 (0201). In this case, the two alleles have a total of 15 nucleotide differences spread over the length HLA-A exon 2, but they show similar melting curves. The melting curve of the mixed samples was significantly shifted to the left (lower melting temperature) due to the 15 mismatches present in the heterohybrids generated in the mixed sample PCR from HLA-A exon 2 (see FIG. 17).

EXAMPLE 16

Monitoring Amplification in Real-Time With Saturating Dyes

A 60 bp fragment of the HTR2A gene was amplified with forward and reverse primers ACCAGGCTCTACAGTAA (SEQ ID NO 21) and GTTAAATGCATCAGAAG (SEQ ID NO 22), respectively. Amplification was performed using the reagents described in Example 11 but with modifications to the cycling parameters, which were 95° C., 0 s; 62° C., 2 s; 74° C., 20 s using the LightCycler®. Various concentrations of SYBR® Green I, GelStar®, and SYTO® 16 were independently present in the reaction mixture. Fluorescence data were acquired once each amplification cycle, up to 40 cycles. Fluorescence crossing points (Cp), calculated as the second derivative maximum of the amplification plot (cycle number plotted on the x-axis against fluorescence intensity on the y-axis), were obtained as follows:

TABLE 4

| Dye present in reaction | Dilution/Concentration | Cp |
|---|---|---|
| SYBR ® Green I | 1:2,500 | No amplification |
|  | 1:5,000 | 26 |
|  | 1:10,000 | 26 |
|  | 1:20,000 | Signal too weak |
| GelStar ® | 1:640 | No amplification |
|  | 1:1,280 | 29 |
|  | 1:2,560 | 28 |
|  | 1:5,120 | 31 |
|  | 1:10,240 | 31 |
|  | 1:20,480 | Signal too weak |
| SYTO ® 16 | 25 µM | No amplification |
|  | 12.5 µM | 30 |
|  | 6.25 µM | 29 |
|  | 3.1 µM | 31 |
|  | 1.5 µM | 33 |
|  | 0.8 µM | Signal too weak |

The Cp value, which represents the cycle number at which signal rises above background, is expected to increase when inhibitors present in the reaction affect the efficiency of amplification. Under the conditions of these experiments, however, inhibition by increasing amounts of dye resulted not as a gradual increase in Cp, but as a sudden and complete elimination of amplification. Due to the small size of the amplicon (which results in a lower signal compared to larger amplicons), SYBR® Green I dye could only be used in the range of two-fold concentrations for real-time monitoring. In contrast, GelStar® and SYTO® 16 could be used within a range of eight-fold concentration. It is contemplated that many saturating dyes have a wide range of concentration that can be used in real-time monitoring of amplification.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference as if fully set forth.

The invention claimed is:

1. A method of PCR analysis comprising the steps of:
    mixing a dsDNA binding dye having a percent saturation of at least 90% with a sample comprising a selected target nucleic acid and primers configured for amplifying the selected target nucleic acid,
    amplifying the target nucleic acid in the presence of the dsDNA binding dye, and
    monitoring fluorescence of the dsDNA binding dye, wherein the monitoring step comprises
    melting the amplified target nucleic acid to generate a melting curve,
    repeating the mixing, amplifying, and generating a melting curve steps with at least one additional target nucleic acid, and comparing the melting curves,
    wherein the melting curve for the selected target nucleic acid is selected as the standard and is plotted as stranded across melting temperatures and the melting curve for each additional target nucleic acid is plotted as a difference from the stranded across the melting curves.

2. The method of claim 1 wherein the target nucleic acid comprises a single nucleotide polymorphism, and the identifying step comprises identifying resultant heteroduplexes and homoduplexes.

3. The method of claim 1 wherein the method comprises mutation scanning by comparing the melting curves.

4. The method of claim 1 further comprising the step of temperature shifting the melting curves by superimposing a portion of each curve.

5. The method of claim 4 further comprising the step of plotting the fluorescence difference between the temperature shifted curves, wherein the melting curve for the target nucleic acid is selected as the standard and is plotted as standard across melting temperatures and the melting curve for each additional target nucleic acid is plotted as a difference from the standard across the melting temperatures.

6. The method of claim 1 wherein the dye is selected from the group consisting of PO-PRO™–1, JO-PRO™–1, SYTO®45, POPO™–3, SYTO®12, TOTO™–3, SYTOX™ Blue, YOYO®–3, SYTO®43, SYTO®11, G5, H5, D6, E6, P6, R6, Y6, Z6, and D8.

7. A method of PCR analysis comprising the steps of:
    mixing a dsDNA binding dye having a percent saturation of at least 50% with a sample comprising a target nucleic acid and primers configured for amplifying the target nucleic acid,
    amplifying the target nucleic acid in the presence of the dsDNA binding dye, and
    monitoring fluorescence of the dsDNA binding dye, wherein the monitoring step comprises melting the amplified target nucleic acid to generate a melting curve, and
    identifying the genotype using a shape of the melting curve, and wherein the dsDNA binding dye is a compound having the formula:

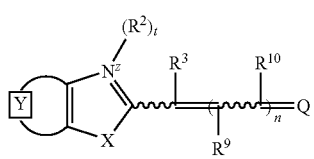

wherein
    the moiety ⊞ represents an optionally-substituted fused monocyclic or polycyclic aromatic ring or an optionally-substituted fused monocyclic or polycyclic nitrogen-containing heteroaromatic ring;
    X is oxygen, sulfur, selenium, tellurium or a moiety selected from $C(CH_3)_2$ and $NR^1$, where $R^1$ is hydrogen or $C_{1-6}$ alkyl;
    $R^2$ is selected from the group consisting of $C_{1-6}$ alkyl, $C_{3-8}$ cycloalkyl, aryl, aryl($C_{1-2}$ alkyl), hydroxyalkyl, alkoxyalkyl, aminoalkyl, mono and dialkylaminoalkyl, trialkylammoniumalkyl, alkylenecarboxylate, alkylenecarboxamide, alkylenesulfonate, alkylsulfonate, optionally substituted cyclic heteroatom-containing moieties, and optionally substituted acyclic heteroatom-containing moieties;
    t=0 or 1;
    Z is a charge selected from 0 or 1;
    $R^3$ is selected from the group consisting of hydrogen, $C_{1-6}$ alkyl, and —C(O)Ph;
    $R^9$ and $R^{10}$ are each independently selected from the group consisting of hydrogen and $C_{1-6}$ alkyl;
    n=0, 1, or 2;
    ⁓ indicates a single bond that is in a tautomeric relationship with an adjacent double bond, and
    Q is an heterocycle selected from the group of structures consisting of:

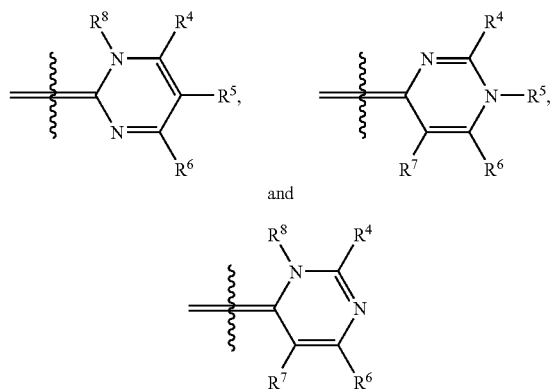

and wherein $R^4$, $R^5$, $R^6$, $R^7$, and $R^8$ are independently selected from the group consisting of hydrogen, halogen, alkyl, cycloalkyl, heteroalkyl, heterocycloalkyl, alkenyl, polyalkenyl, alkynyl, polyalkynyl, alkenylalkynyl, aryl, heteroaryl, alkoxy, alkylthio, and dialkylamino, each of which may be optionally substituted; an acyclic heteroatom-containing moiety or a cyclic heteroatom-containing moiety; a BRIDGE-DYE; and a reactive group; each of which optionally includes a quaternary ammonium moiety.

8. The method of claim 7 wherein the moiety ⊞ represents an optionally-substituted fused monocyclic or polycyclic aromatic ring selected from the group consisting of optionally substituted benzo, optionally substituted pyridino, and optionally substituted naphtho; and X is oxygen or sulfur.

9. The method of claim 7 wherein the moiety ⊞ represents a benzo or a naphtho having a substituent selected from the group consisting of halo, alkyl, amino, monoalkylamino, dialkylamino, alkylsulfonyl, haloalkylsulfonyl, and optionally substituted phenylsulfonyl.

10. The method of claim 7 wherein $R^2$ is selected from the group consisting of $C_{1-6}$ alkyl, $C_{3-8}$ cycloalkyl, aryl, aryl($C_{1-2}$ alkyl), aminoalkyl, monoalkylaminoalkyl, dialkylaminoalkyl, trialkylammoniumalkyl, alkylsulfonate, alkylenesulfonate, optionally substituted cyclic heteroatom-containing moieties, and optionally substituted acyclic heteroatom-containing moieties.

11. The method of claim 7 wherein Q is the heterocycle:

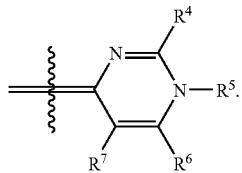

12. The method of claim 7 wherein $R^4$, $R^5$, $R^6$, $R^7$, and $R^8$ are independently selected from the group consisting of hydrogen, halogen, thiol, alkylthio, alkyl, aminoalkyl, monoalkylaminoalkyl, dialkylaminoalkyl, trialkylammmoniumalkyl, piperidino, piperazino, 4-methylpiperazinium-1-yl, and aryl.

13. The method of claim 7 wherein t is 1, n=0, and at least one of $R^4$, $R^5$, $R^6$, $R^7$, and $R^8$ is selected from the group consisting of halogen, thiol, alkylthio, $C_{2-6}$ alkyl, aminoalkyl, monoalkylaminoalkyl, dialkylaminoalkyl, trialkylammmoniumalkyl, piperidino, piperazino, 4-methylpiperazinium-1-yl, and aryl.

14. The method d of claim 13 wherein $R^5$ is selected from the group consisting of halogen, thiol, $C_{2-6}$ alkyl, aminoalkyl, monoalkylaminoalkyl, dialkylaminoalkyl, trialkylammmoniumalkyl, piperidino, piperazino, 4-methylpiperazinium-1-yl, and aryl.

15. The method of claim 13 wherein $R^3$, $R^9$, and $R^{10}$ are each hydrogen; and $R^2$ is selected from the group consisting of $C_{1-6}$ alkyl, aryl, aryl($C_{1-2}$alkyl), aminoalkyl, monoalkylaminoalkyl, dialkylaminoalkyl, trialkylammoniumalkyl, alkylsulfonate, and alkylenesulfonate.

16. A method of PCR analysis comprising the steps of:
providing a mixture of a dsDNA binding dye having at least 90% saturation, a target nucleic acid, and primers configured for amplifying the target nucleic acid,
amplifying the target nucleic acid in the presence of the dsDNA binding dye,
monitoring fluorescence of the dsDNA binding dye,
generating a melting curve for the target nucleic acid,
normalizing magnitude differences of the melting curve,
repeating the providing, amplifying, generating and normalizing steps with at least one additional target nucleic acid,
comparing the magnitude difference normalized melting curves, and plotting the fluorescence difference between the magnitude difference normalized curves, wherein the melting curve of one selected target nucleic acid is selected as the standard and is plotted as standard across melting temperatures and the melting curve for each additional target nucleic acid is plotted as a difference from the standard across the melting temperatures.

17. A method of PCR analysis comprising the steps of:
providing a mixture of a dsDNA binding dye having at least 90% saturation, a target nucleic acid, and primers configured for amplifying the target nucleic acid,
amplifying the target nucleic acid in the presence of the dsDNA binding dye,
monitoring fluorescence of the dsDNA binding dye,
generating a melting curve for the target nucleic acid,
normalizing magnitude differences of the melting curve,
repeating the providing, amplifying, generating and normalizing steps with at least one additional target nucleic acid,
comparing the magnitude difference normalized melting curves, and plotting the fluorescence difference between the magnitude difference normalized curves, wherein the melting curve of one selected target nucleic acid is selected as the standard and is plotted as standard across melting temperatures and the melting curve for each additional target nucleic acid is plotted as a difference from the standard across the melting temperatures wherein the standard is plotted as zero across all melting temperatures.

18. The method of claim 16 further comprising the step of temperature shifting melting curves by superimposing a portion of each curve and plotting the fluorescence difference between the temperature shifted curves, wherein the melting curve for the target nucleic acid is selected as the standard and is plotted as standard across melting temperatures and the melting curve for each additional target nucleic acid is plotted as a difference from the standard across the melting temperatures.

* * * * *

UNITED STATES PATENT AND TRADEMARK OFFICE
CERTIFICATE OF CORRECTION

PATENT NO. : 7,582,429 B2
APPLICATION NO. : 10/531966
DATED : September 1, 2009
INVENTOR(S) : Wittwer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 778 days.

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,582,429 B2 | Page 1 of 1 |
| APPLICATION NO. | : 10/531966 | |
| DATED | : September 1, 2009 | |
| INVENTOR(S) | : Carl T. Wittwer et al. | |

It is certified that error appears in the above-identified patent and that said Letters Patent is hereby corrected as shown below:

Claim 1, Column 53, line 17: replace "stranded" with --standard--

Claim 1, Column 53, line 21: replace "stranded" with --standard--

Signed and Sealed this
Fifteenth Day of November, 2011

David J. Kappos
*Director of the United States Patent and Trademark Office*

SEQUENCE LISTING

<160> NUMBER OF SEQ ID NOS: 24

<210> SEQ ID NO 1
<211> LENGTH: 20
<212> TYPE: DNA
<213> ORGANISM: Homo sapiens

<400> SEQUENCE: 1
ggcaccatta aagaaaatat                                              20

<210> SEQ ID NO 2
<211> LENGTH: 18
<212> TYPE: DNA
<213> ORGANISM: Homo sapiens

<400> SEQUENCE: 2

```
tcatcatagg aaacacca                                              18

<210> SEQ ID NO 3
<211> LENGTH: 20
<212> TYPE: DNA
<213> ORGANISM: Homo sapiens

<400> SEQUENCE: 3
acacaactgt gttcactagc                                            20

<210> SEQ ID NO 4
<211> LENGTH: 20
<212> TYPE: DNA
<213> ORGANISM: Homo sapiens

<400> SEQUENCE: 4
caacttcatc cacgttcacc                                            20

<210> SEQ ID NO 5
<211> LENGTH: 14
<212> TYPE: DNA
<213> ORGANISM: Homo sapiens

<400> SEQUENCE: 5
ccagctccgg gaga                                                  14

<210> SEQ ID NO 6
<211> LENGTH: 21
<212> TYPE: DNA
<213> ORGANISM: Homo sapiens

<400> SEQUENCE: 6
catacaggat ggttaacatg g                                          21

<210> SEQ ID NO 7
<211> LENGTH: 21
<212> TYPE: DNA
<213> ORGANISM: Homo sapiens

<400> SEQUENCE: 7
agaatataca cttctgctta g                                          21

<210> SEQ ID NO 8
<211> LENGTH: 17
<212> TYPE: DNA
<213> ORGANISM: Homo sapiens

<400> SEQUENCE: 8
tatcactata tgcatgc                                               17

<210> SEQ ID NO 9
<211> LENGTH: 26
<212> TYPE: DNA
<213> ORGANISM: Homo sapiens

<400> SEQUENCE: 9
gaaaccgcct ctgcggggag aagcaa                                     26

<210> SEQ ID NO 10
<211> LENGTH: 26
<212> TYPE: DNA
<213> ORGANISM: Homo sapiens
```

```
<400> SEQUENCE: 10
gaaacggcct ctgcggggag aagcaa                                              26

<210> SEQ ID NO 11
<211> LENGTH: 26
<212> TYPE: DNA
<213> ORGANISM: Homo sapiens

<400> SEQUENCE: 11
gaaaccgcct ctgtggggag aagcaa                                              26

<210> SEQ ID NO 12
<211> LENGTH: 26
<212> TYPE: DNA
<213> ORGANISM: Homo sapiens

<400> SEQUENCE: 12
gaaacggcct ctgtggggag aagcaa                                              26

<210> SEQ ID NO 13
<211> LENGTH: 24
<212> TYPE: DNA
<213> ORGANISM: Homo sapiens

<400> SEQUENCE: 13
tgttggtccc aattgtctcc cctc                                                24

<210> SEQ ID NO 14
<211> LENGTH: 22
<212> TYPE: DNA
<213> ORGANISM: Homo sapiens

<400> SEQUENCE: 14
agccgcgccg ggaagagggt cg                                                  22

<210> SEQ ID NO 15
<211> LENGTH: 22
<212> TYPE: DNA
<213> ORGANISM: Homo sapiens

<400> SEQUENCE: 15
agccgcgcct ggaagagggt cg                                                  22

<210> SEQ ID NO 16
<211> LENGTH: 18
<212> TYPE: DNA
<213> ORGANISM: Homo sapiens

<400> SEQUENCE: 16 ggccgggtc actcaccg                                                        18

<210> SEQ ID NO 17
<211> LENGTH: 17
<212> TYPE: DNA
<213> ORGANISM: Homo sapiens

<400> SEQUENCE: 17 cccggggttgg tcgggc                                                        17

<210> SEQ ID NO 18
<211> LENGTH: 17
<212> TYPE: DNA
<213> ORGANISM: Homo sapiens
```

-continued

<400> SEQUENCE: 18
cccaggttgg tcggggc                                                        17

<210> SEQ ID NO 19
<211> LENGTH: 19
<212> TYPE: DNA
<213> ORGANISM: Homo sapiens

<400> SEQUENCE: 19
atcagggagg cgccccgtg                                                      19

<210> SEQ ID NO 20
<211> LENGTH: 19
<212> TYPE: DNA
<213> ORGANISM: Homo sapiens

<400> SEQUENCE: 20
atcagtgagg cgccccgtg                                                      19

<210> SEQ ID NO 21
<211> LENGTH: 17
<212> TYPE: DNA
<213> ORGANISM: Homo sapiens

<400> SEQUENCE: 21
accaggctct acagtaa                                                        17

<210> SEQ ID NO 22
<211> LENGTH: 17
<212> TYPE: DNA
<213> ORGANISM: Homo sapiens

<400> SEQUENCE: 22
gttaaatgca tcagaag                                                        17

<210> SEQ ID NO 23
<211> LENGTH: 20
<212> TYPE: DNA
<213> ORGANISM: Homo sapiens

<400> SEQUENCE: 23
ggcaccatta aagaaaatat                                                     20

<210> SEQ ID NO 24
<211> LENGTH: 23
<212> TYPE: DNA
<213> ORGANISM: Homo sapiens

<400> SEQUENCE: 24
tctgtatcta tattcatcat agg                                                 23